(12) United States Patent
Wada

(10) Patent No.: US 7,695,891 B2
(45) Date of Patent: Apr. 13, 2010

(54) PHOTOSENSITIVE COMPOSITION, PATTERN FORMING METHOD USING THE PHOTOSENSITIVE COMPOSITION AND COMPOUND FOR USE IN THE PHOTOSENSITIVE COMPOSITION

(75) Inventor: Kenji Wada, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 27 days.

(21) Appl. No.: 11/471,713

(22) Filed: Jun. 21, 2006

(65) Prior Publication Data

US 2007/0082289 A1    Apr. 12, 2007

(30) Foreign Application Priority Data

Jun. 21, 2005    (JP) .................... P.2005-180980

(51) Int. Cl.
*G03F 7/004*    (2006.01)
*C07C 309/00*    (2006.01)

(52) U.S. Cl. .................... 430/270.1; 430/326; 430/921; 430/923; 430/925; 562/30; 562/400

(58) Field of Classification Search .............. 430/270.1, 430/914, 919, 921, 923, 925, 326; 522/25, 522/31; 562/30, 400
See application file for complete search history.

(56) References Cited

U.S. PATENT DOCUMENTS

| 4,348,310 | A | * | 9/1982 | Silva et al. ................... 524/167 |
| 5,011,983 | A | * | 4/1991 | Behr ........................... 562/113 |
| 6,358,665 | B1 | * | 3/2002 | Pawlowski et al. ........ 430/270.1 |
| 2001/0014428 | A1 | * | 8/2001 | Uetani et al. .............. 430/270.1 |
| 2002/0077493 | A1 | * | 6/2002 | Ohsawa et al. ................. 558/46 |
| 2003/0039916 | A1 | * | 2/2003 | Adegawa et al. .......... 430/270.1 |
| 2004/0087690 | A1 | | 5/2004 | Lamanna et al. |
| 2006/0014098 | A1 | * | 1/2006 | Hada et al. ................ 430/270.1 |
| 2007/0054214 | A1 | * | 3/2007 | Ebata et al. ............... 430/270.1 |

FOREIGN PATENT DOCUMENTS

| JP | 06-242606 A | | 9/1994 |
| JP | 09-073173 A | | 3/1997 |
| JP | 11-501909 A | | 2/1999 |
| JP | 11-160861 A | | 6/1999 |
| JP | 2002-131897 A | | 5/2002 |
| JP | 2002-268223 A | | 9/2002 |
| JP | 2003-149812 A | | 5/2003 |
| JP | 2003-246786 A | | 9/2003 |
| WO | WO 2004/057422 | * | 7/2004 |
| WO | WO 2004078703 | * | 9/2004 |

* cited by examiner

*Primary Examiner*—Cynthia H Kelly
*Assistant Examiner*—Anca Eoff
(74) *Attorney, Agent, or Firm*—Sughrue Mion, PLLC

(57) ABSTRACT

A photosensitive composition comprising a compound capable of generating a compound having a specific structure upon irradiation with actinic rays or radiation; a pattern forming method using the photosensitive composition; a compound having a specific structure; and a compound capable of generating a compound having a specific structure upon irradiation with actinic rays or radiation.

28 Claims, 1 Drawing Sheet

PHOTOSENSITIVE COMPOSITION, PATTERN FORMING METHOD USING THE PHOTOSENSITIVE COMPOSITION AND COMPOUND FOR USE IN THE PHOTOSENSITIVE COMPOSITION

BACKGROUND OF THE INVENTION

1. Field of the Invention

The present invention relates to a photosensitive composition capable of changing in its properties by undergoing a reaction upon irradiation with actinic rays or radiation, a pattern forming method using the photosensitive composition, and a compound for use in the photosensitive composition. More specifically, the present invention relates to a photosensitive composition for use in the production process of a semiconductor such as IC, in the production of a circuit substrate of liquid crystal, thermal head or the like, in other photofabrication processes or in the lithographic printing plate or acid-curable composition, and also relates to a pattern forming method using the photosensitive composition and a compound for use in the photosensitive composition.

2. Description of the Related Art

The chemical amplification resist composition is a pattern forming material capable of forming a pattern on a substrate by producing an acid in the exposed area upon irradiation with actinic rays or radiation such as far ultraviolet light and through a reaction using this acid as the catalyst, changing the solubility in a developer between the area irradiated with actinic rays or radiation and the non-irradiated area.

In the case of using a KrF excimer laser as the exposure light source, a resin having small absorption in the region of 248 nm and having a basic skeleton of poly(hydroxystyrene) is predominantly used as the main component, and this is an excellent system capable of forming a good pattern with high sensitivity and high resolution as compared with the conventional naphthoquinonediazide/novolak resin system.

In the case of using a light source of emitting light at a shorter wavelength, for example, in using an ArF excimer laser (193 nm) as the light source, a satisfactory pattern cannot be formed even by the above-described chemical amplification system because the compound having an aromatic group substantially has large absorption in the region of 193 nm.

In order to solve this problem, a resist containing a resin having an alicyclic hydrocarbon structure with high transparency has been developed for use with an ArF excimer laser. As for the alicyclic hydrocarbon structure, a norbornene or adamantane skeleton showing high transparency and high dry etching resistance is used as described in JP-A-2002-131897 (the term "JP-A" as used herein means an "unexamined published Japanese patent application")), JP-A-2003-149812, JP-T-11-501909 (the term (the term "JP-T" as used herein means a "published Japanese translation of a PCT patent application"), JP-A-2002-268223, JP-A-2003-246786 and JP-A-9-73173. However, the alicyclic structure generally has low polarity, and the reactivity for deprotection in the resin is greatly decreased as compared with that in poly(hydroxystyrene). Therefore, an acid having high acidity is necessary for the image formation and, for example, a specific fluoro-organic sulfonic acid is used in JP-A-2002-131897 and JP-A-2003-149812. Also, a composition containing an acid generator comprising an imide anion capable of generating a high-acidity imide upon irradiation with actinic rays or radiation is described in JP-T-11-501909, JP-A-2002-268223 and JP-A-2003-246786. Furthermore, a specific organic sulfonic acid is used, for example, in JP-A-6-242606, JP-A-11-160861 and U.S. Patent Application 2004/0087690A1.

However, many points still remain unsatisfied, and improvement is demanded in terms of the PEB temperature dependency, exposure latitude, pattern profile and the like.

SUMMARY OF THE INVENTION

Accordingly, an object of the present invention is to provide a photosensitive composition improved in the PEB temperature dependency, exposure latitude and pattern profile and enhanced in the sensitivity and dissolution contrast at the exposure with EUV light, a pattern forming method using the photosensitive composition, and a compound for use in the photosensitive composition.

The present invention is as follows.

(1) A photosensitive composition comprising:

(A) a compound capable of generating a compound represented by formula (I) upon irradiation with actinic rays or radiation:

A-R—X—F     (I)

wherein X represents —CO— or —SO$_2$—;

R represents a divalent linking group; and

A represents an acidic group.

(2) The photosensitive composition as described in (1) above, wherein the acidic group of A in formula (I) is —SO$_3$H, —CO$_2$H or —X—NH—X—R$_1$, and wherein X represents —CO— or —SO$_2$—, and a plurality of X's may be the same or different; and R$_1$ represents a monovalent organic group.

(3) The photosensitive composition as described in (1) or (2) above, wherein the compound (A) capable of generating a compound represented by formula (I) upon irradiation with actinic rays or radiation is a sulfonium salt compound of the compound represented by formula (I) or an iodonium salt compound of the compound represented by formula (I).

(4) A pattern forming method comprising:

forming a photosensitive film from a photosensitive composition as described in any of (1) to (3) above; and exposing and developing the photosensitive film.

(5) A compound represented by formula (I) or a salt of the compound represented by formula (I):

A-R—X—F     (I)

wherein X represents —CO— or —SO$_2$—;

R represents a divalent linking group; and

A represents an acidic group.

(6) The compound or the salt of the compound as described in (5) above, wherein the acidic group of A in formula (I) is —SO$_3$H, —CO$_2$H or —X—NH—X—R$_1$, and wherein X represents —CO— or —SO$_2$—, and a plurality of X's may be the same or different; and R$_1$ represents a monovalent organic group.

(7) A compound (A) capable of generating a compound represented by formula (I) upon irradiation with actinic rays or radiation:

A-R—X—F     (I)

wherein X represents —CO— or —SO$_2$—;

R represents a divalent linking group; and

A represents an acidic group.

(8) The compound as described in (7) above,
wherein the acidic group of A in formula (I) is —$SO_3H$, —$CO_2H$ or —X—NH—X—$R_1$, and
wherein X represents —CO— or —$SO_2$—, and a plurality of X's may be the same or different; and
$R_1$ represents a monovalent organic group.

Furthermore, the preferred embodiment includes the following constitutions.

(9) The photosensitive composition as described in any of (1) to (3) above, which further comprises (B) a compound capable of generating an acid upon irradiation with actinic rays or radiation.

(10) The photosensitive composition as described in (9) above,
wherein the compound as the component (B) is a sulfonium salt of fluoro-substituted alkanesulfonic acid, fluorine-substituted benzenesulfonic acid or fluorine-substituted imide acid.

(11) The photosensitive composition as described in any of (1) to (3), (9) and (10) above, which is a positive photosensitive composition and further comprises (C) a resin capable of decomposing under an action of an acid to increase a solubility of the resin (C) in an alkali developer.

(12) The photosensitive composition as described in (11) above,
wherein the resin as the component (C) has a fluorine atom in a main or side chain.

(13) The photosensitive composition as described in (12) above,
wherein the resin as the component (C) has a hexafluoroisopropanol structure.

(14) The photosensitive composition as described in (11) above,
wherein the resin as the component (C) has a hydroxystyrene structural unit.

(15) The photosensitive composition as described in (11) above,
wherein the resin as the component (C) has at least one repeating unit selected from 2-alkyl-2-adamantyl (meth) acrylate and dialkyl(1-adamantyl)methyl (meth)acrylate.

(16) The photosensitive composition as described in (11) above,
wherein the resin as the component (C) has a monocyclic or polycyclic alicyclic hydrocarbon structure.

(17) The photosensitive composition as described in (16) above,
wherein the resin as the component (C) has at least one repeating unit selected from 2-alkyl-2-adamantyl (meth) acrylate and dialkyl(1-adamantyl)methyl (meth)acrylate, at least one repeating unit having a lactone structure and at least one repeating unit having a hydroxyl group.

(18) The photosensitive composition as described in (17) above,
wherein the resin as the component (C) further has a repeating unit having a carboxyl group.

(19) The photosensitive composition as described in (11) above,
wherein the resin as the component (C) has a silicon atom in a main or side chain.

(20) The photosensitive composition as described in (11) above,
wherein the resin as the component (C) has a repeating unit having a lactone structure.

(21) The photosensitive composition as described in any of (11) to (20) above, which further comprises (D) a dissolution inhibiting compound capable of decomposing under an action of an acid to increase a solubility of the compound (D) in an alkali developer and having a molecular weight of 3,000 or less.

(22) The photosensitive composition as described in any of (1) to (3), (9) and (10) above, which is a positive photosensitive composition and further comprises:
(E) a resin soluble in an alkali developer; and
(D) a dissolution inhibiting compound capable of decomposing under an action of an acid to increase a solubility of the compound (D) in an alkali developer and having a molecular weight of 3,000 or less.

(23) The photosensitive composition as described in any of (1) to (3), (9) and (10) above, which is a negative photosensitive composition and further comprises:
(E) a resin soluble in an alkali developer; and
(F) an acid crosslinking agent capable of crosslinking with the resin soluble in an alkali developer under an action of an acid.

(24) The photosensitive composition as described in any of (1) to (3) and (9) to (23) above, which further comprises at least one of (G) a basic compound and (H) at least one of a fluorine-containing surfactant and a silicon-containing surfactant.

(25) The photosensitive composition as described in (24) above,
wherein the basic compound (G) is a compound having a structure selected from an imidazole structure, a diazabicyclo structure, an onium hydroxide structure, an onium carboxylate structure, a trialkylamine structure, an aniline structure and a pyridine structure, an alkylamine derivative having at least one of a hydroxyl group and an ether bond or an aniline derivative having at least one of a hydroxyl group and an ether bond.

DETAILED DESCRIPTION OF THE INVENTION

Figure 1:
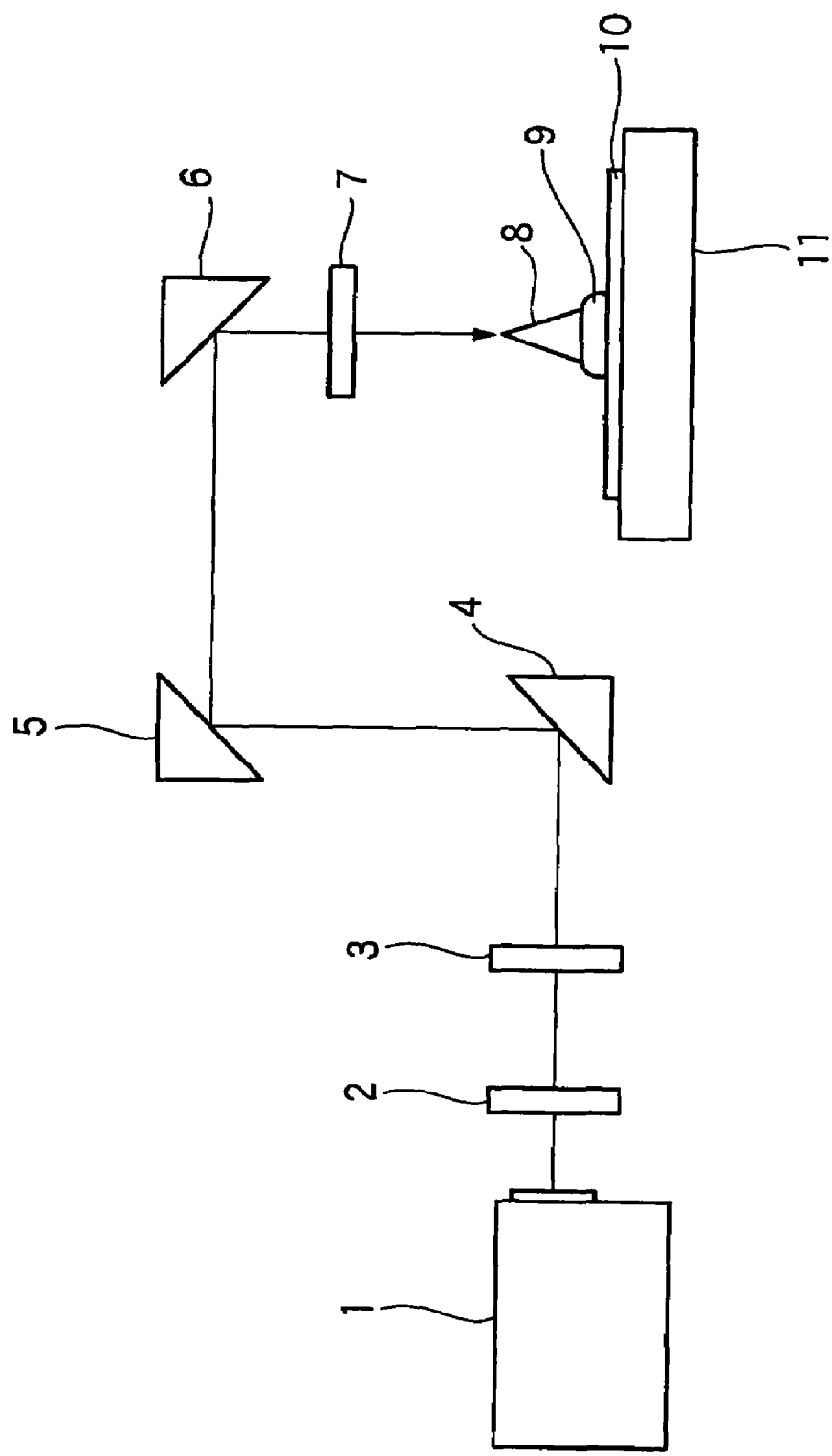
FIG. 1 is a schematic view of the two-beam interference exposure testing apparatus.

The present invention is described in detail below.

In the present invention, when a group (atomic group) is denoted without specifying whether substituted or unsubstituted, the group includes both a group having no substituent and a group having a substituent. For example, an "alkyl group" includes not only an alkyl group having no substituent (unsubstituted alkyl group) but also an alkyl group having a substituent (substituted alkyl group).

The positive photosensitive composition, preferably positive resist composition, of the present invention comprises (A) a compound capable of generating a compound represented by formula (I) upon irradiation with actinic rays or radiation and (C) a resin capable of decomposing under the action of an acid to increase the solubility in an alkali developer and, if desired, further comprises (B) a compound capable of generating an acid upon irradiation with actinic rays or radiation and (D) a dissolution inhibiting compound capable of decomposing under the action of an acid to increase the solubility in an alkali developer and having a molecular weight of 3,000 or less; or comprises (A) a compound capable of generating a compound represented by formula (I) upon irradiation with actinic rays or radiation, (E) a resin soluble in an alkali developer and (D) a dissolution inhibiting compound capable of decomposing under the action of an acid to increase the solubility in an alkali developer and having a molecular weight of 3,000 or less and, if desired, further comprises (B) a compound capable of generating an acid upon irradiation with actinic rays or radiation.

The negative photosensitive composition, preferably negative resist composition, of the present invention comprises (A) a compound capable of generating a compound represented by formula (I) upon irradiation with actinic rays or radiation, (E) a resin soluble in an alkali developer and (F) an acid crosslinking agent capable of crosslinking with the alkali developer-soluble resin under the action of an acid and, if desired, further comprises (B) a compound capable of generating an acid upon irradiation with actinic rays or radiation.

[1] (A) Compound Capable of Generating a Compound Represented by Formula (I) upon Irradiation with Actinic Rays or Radiation The photosensitive composition of the present invention comprises a compound (hereinafter referred to as a "compound (A)") capable of generating a compound represented by the following formula (I) upon irradiation with actinic rays or radiation.

    A—R—X—F    (I)

wherein
X represents —CO— or —SO$_2$—,
R represents a divalent linking group, and
A represents an acidic group.

The divalent linking group as R in formula (I) is preferably a fluorine atom-containing divalent linking group having a carbon number of 1 to 8, and examples thereof include a fluorine atom-containing alkylene group having a carbon number of 1 to 8, and a fluorine atom-containing phenylene group. The divalent linking group is more preferably a fluorine atom-containing alkylene group, and the carbon number thereof is preferably from 2 to 6, more preferably from 2 to 4. The alkylene group may contain a linking group such as oxygen atom and sulfur atom, in the alkylene chain. The alkylene group is preferably an alkylene group where from 30 to 100% by number of the hydrogen atom is replaced by a fluorine atom, and in this case, the thermal stability is enhanced. Specifically, a perfluoroakylene group is preferred, and a perfluoroethylene group, a perfluoropropylene group and a perfluorobutylene group are more preferred.

The acidic group of A in formula (I) is a group showing acidity, and examples thereof include —SO$_3$H, —CO$_2$H and —X—NH—X—R$_1$ (wherein X represents —CO— or —SO$_2$—, the plurality of X's may be the same or different, and R$_1$ represents a monovalent organic group).

The monovalent organic group as R$_1$ is preferably a monovalent organic group having a carbon number of 1 to 40, and examples thereof include an alkyl group, a cycloalkyl group, an aryl group, an aralkyl group and an alkenyl group.

The alkyl group as R$_1$, which may have a substituent, is preferably a linear or branched alkyl group having a carbon number of 1 to 30 and may contain an oxygen atom, a sulfur atom or a nitrogen atom in the alkyl chain. Specific examples thereof include a linear alkyl group such as methyl group, ethyl group, n-propyl group, n-butyl group, n-pentyl group, n-hexyl group, n-octyl group, n-dodecyl group, n-tetradecyl group and n-octadecyl group; and a branched alkyl group such as isopropyl group, isobutyl group, tert-butyl group, neopentyl group and 2-ethylhexyl group. The alkyl group is more preferably substituted by a fluorine atom, because the thermal stability is enhanced. Examples of the alkyl group substituted by a fluorine atom include a perfluoroalkyl group such as perfluoromethyl group, perfluoroethyl group, perfluoropropyl group and perfluorobutyl group.

The cycloalkyl group as R$_1$, which may have a substituent, is preferably a cycloalkyl group having a carbon number of 3 to 20 and may contain an oxygen atom in the ring. Specific examples thereof include a cyclopropyl group, a cyclopentyl group, a cyclohexyl group, a norbornyl group and an adamantyl group.

The aryl group as R$_1$, which may have a substituent, is preferably an aryl group having a carbon number of 6 to 14, and examples thereof include a phenyl group and a naphthyl group. The aryl group is preferably substituted by a fluorine atom. Examples of the aryl group substituted by a fluorine atom include a perfluorophenyl group.

The aralkyl group as R$_1$, which may have a substituent, is preferably an aralkyl group having a carbon number of 7 to 20, and examples thereof include a benzyl group, a phenethyl group, a naphthylmethyl group and a naphthylethyl group.

The alkenyl group as R$_1$ includes a group having a double bond at an arbitrary position of the alkyl group described above.

Examples of the substituent which the above-described groups each may have include a halogen atom, a hydroxyl group, a nitro group, a cyano group, a carboxy group, a carbonyl group, a cycloalkyl group (preferably having a carbon number of 3 to 10), an aryl group (preferably having a carbon number of 6 to 14), an alkoxy group (preferably having a carbon number of 1 to 10), an acyl group (preferably having a carbon number of 2 to 20), an acyloxy group (preferably having a carbon number of 2 to 10), an alkoxycarbonyl group (preferably having a carbon number of 2 to 20) and an aminoacyl group (preferably having a carbon number of 2 to 10). As for the cyclic structure in the aryl group, cycloalkyl group and the like, examples of the substituent further include an alkyl group (preferably having a carbon number of 1 to 10). As for the aminoacyl group, examples of the substituent further include one or two alkyl group (preferably having a carbon number of 1 to 10).

In formula (I), A is preferably —SO$_3$H and in this case, the pattern profile is enhanced.

The compound represented by formula (I) is a novel compound.

The compound represented by formula (I) can be easily synthesized, for example, by a method of selectively hydrolyzing only one sulfonyl halide moiety of a general bis-sulfonyl halide compound with a base (Scheme 1 shown below).

The compound represented by formula (I) where the acidic group of A is —X—NH—X—R$_1$ can be easily synthesized, for example, by a method of reacting only one sulfonyl halide moiety of a bis-sulfonyl halide compound with a sulfonamide (R$_1$—X—NH$_2$) or the like (Scheme 2 shown below).

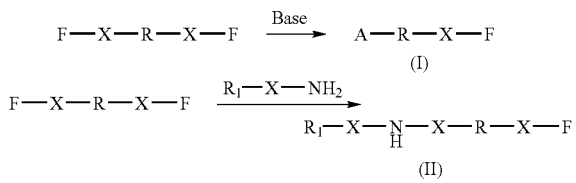

Specific examples of the compound represented by formula (I) are set forth below, but the present invention is not limited thereto.

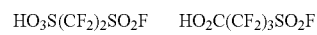
    HO$_3$S(CF$_2$)$_2$SO$_2$F    HO$_2$C(CF$_2$)$_3$SO$_2$F

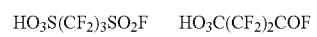
    HO$_3$S(CF$_2$)$_3$SO$_2$F    HO$_3$C(CF$_2$)$_2$COF

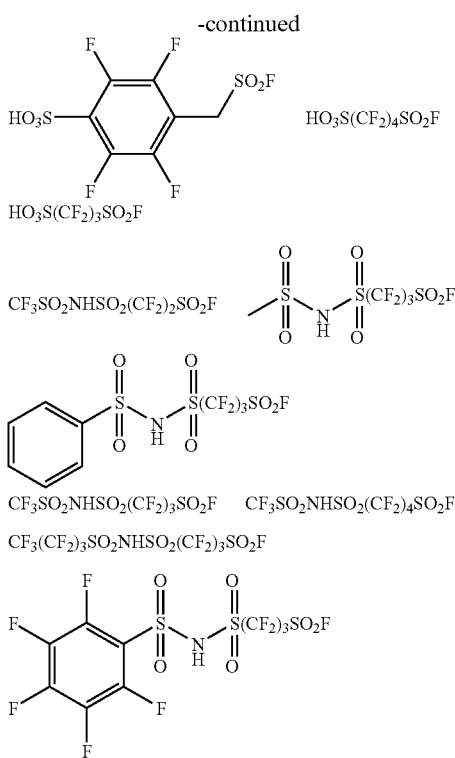

The compound capable of generating a compound represented by formula (I) upon irradiation with actinic rays or radiation is a novel compound.

The compound capable of generating a compound represented by formula (I) upon irradiation with actinic rays or radiation can be easily synthesized from a compound represented by formula (I) or a lithium, sodium, potassium or ammonium salt thereof and a hydroxide, bromide, chloride or the like of iodonium or sulfonium, by utilizing the salt-exchange method described in JP-T-11-501909 or JP-A-2003-246786.

The compound capable of generating a compound represented by formula (I) upon irradiation with actinic rays or radiation is preferably a sulfonium salt compound of the compound represented by formula (I) or an iodonium salt compound of the compound represented by formula (I).

The compound capable of generating a compound represented by formula (I) upon irradiation with actinic rays or radiation is more preferably a compound represented by the following formula (A1) or (A2):

In formula (A1), $R_{201}$, $R_{202}$ and $R_{203}$ each independently represents an organic group.

$X^-$ represents an anion of the compound represented by formula (I).

The carbon number of the organic group as $R_{201}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

Specific examples of the organic group as $R_{201}$, $R_{202}$ and $R_{203}$ include the corresponding groups in the compounds (A1a), (A1b) and (A1c) described later.

The compound may be a compound having a plurality of structures represented by formula (A1), for example, may be a compound having a structure that at least one of $R_{201}$ to $R_{203}$ in the compound represented by formula (A1) is bonded to at least one of $R_{201}$ to $R_{203}$ in another compound represented by formula (A1).

The component (A1) is more preferably a compound (A1a), (A1b) or (A1c) described below.

The compound (A1a) is an arylsulfonium compound where at least one of $R_{201}$ to $R_{203}$ in formula (A1) is an aryl group, that is, a compound having arylsulfonium as the cation.

In the arylsulfonium compound, $R_{201}$ to $R_{203}$ all may be an aryl group or a part of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, a diarylcycloalkylsulfonium compound, an aryldialkylsulfonium compound, an aryldicycloalkylsulfonium compound and an arylalkylcycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene). In the case where the arylsulfonium compound has two or more aryl groups, these two or more aryl groups may be the same of different.

The alkyl group which is present, if desired, in the arylsulfonium compound is preferably a linear or branched alkyl group having a carbon number of 1 to 15, and examples thereof include a methyl group, an ethyl group, a propyl group, an n-butyl group, a sec-butyl group and a tert-butyl group.

The cycloalkyl group which is present, if desired, in the arylsulfonium compound is preferably a cycloalkyl group having a carbon number of 3 to 15, and examples thereof include a cyclopropyl group, a cyclobutyl group and a cyclohexyl group.

The aryl group, alkyl group and cycloalkyl group of $R_{20}$, to $R_{203}$ each may have, as the substituent, an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 14), an alkoxy group (for example, an alkoxy group having a carbon number of 1 to 15), a halogen atom, a hydroxyl group or a phenylthio group.

The substituent is preferably a linear or branched alkyl group having a carbon number of 1 to 12, a cycloalkyl group having a carbon number of 3 to 12, or a linear, branched or cyclic alkoxy group having a carbon number of 1 to 12, and most preferably an alkyl group having a carbon number of 1 to 4, or an alkoxy group having a carbon number of 1 to 4. The substituent may be substituted to any one of three members $R_{201}$ to $R_{203}$ or may be substituted to all of these three members. In the case where $R_{20}$, to $R_{203}$ are an aryl group, the substituent is preferably substituted at the p-position of the aryl group.

The compound (A1b) is described below.

The compound (A1b) is a compound when $R_{201}$ to $R_{203}$ in formula (A1) each independently represents an organic group having no aromatic ring. The aromatic ring as used herein includes an aromatic ring having a heteroatom.

The organic group having no aromatic ring as $R_{201}$ to $R_{203}$ has a carbon number of generally from 1 to 30, preferably from 1 to 20.

$R_{201}$ to $R_{203}$ each independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group as $R_{201}$ to $R_{203}$ may be either linear or branched and is preferably a linear or branched alkyl group having a carbon number of 1 to 20 (e.g., methyl, ethyl, propyl, butyl, pentyl), more preferably a linear or branched 2-oxoalkyl group or an alkoxycarbonylmethyl group.

The cycloalkyl group as $R_{201}$ to $R_{203}$ is preferably a cycloalkyl group having a carbon number of 3 to 10 (e.g., cyclopentyl, cyclohexyl, norbornyl), more preferably a 2-oxocycloalkyl group.

The linear or branched 2-oxoalkyl group as $R_{201}$ to $R_{203}$ may have a double bond in the chain and is preferably a group having >C=O at the 2-position of the above-described alkyl group.

The 2-oxocycloalkyl group as $R_{201}$ to $R_{203}$ may have a double bond in the chain and is preferably a group having >C=O at the 2-position of the above-described cycloalkyl group.

The alkoxy group in the alkoxycarbonylmethyl group as $R_{201}$ to $R_{203}$ is preferably an alkoxy group having a carbon number of 1 to 5 (e.g., methoxy, ethoxy, propoxy, butoxy, pentoxy).

$R_{201}$ to $R_{203}$ each may be further substituted by a halogen atom, an alkoxy group (for example, an alkoxy group having a carbon number of 1 to 5), an alkoxycarbonyl group (for example, an alkoxycarbonyl group having a carbon number of 1 to 5), a hydroxyl group, a cyano group or a nitro group.

The compound (A1c) is a compound represented by the following formula (A1c), and this is a compound having an arylacylsulfonium salt structure.

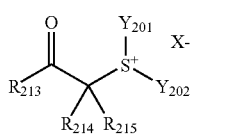

(A1c)

In formula (A1c), $R_{213}$ represents an aryl group which may have a substituent, and is preferably a phenyl group or a naphthyl group.

Preferred examples of the substituent on $R_{213}$ include an alkyl group, an alkoxy group, an acyl group, a nitro group, a hydroxyl group, an alkoxycarbonyl group and a carboxy group.

$R_{214}$ and $R_{215}$ each independently represents a hydrogen atom, an alkyl group or a cycloalkyl group.

$Y_{201}$ and $Y_{202}$ each independently represents an alkyl group, a cycloalkyl group, an aryl group or a vinyl group.

$X^-$ represents an anion of the compound represented by formula (I).

$R_{213}$ and $R_{214}$ may combine with each other to form a ring structure, $R_{214}$ and $R_{215}$ may combine with each other to form a ring structure, and $Y_{201}$ and $Y_{202}$ may combine with each other to form a ring structure. The ring structure formed may contain an oxygen atom, a sulfur atom, an ester bond or an amide bond. Examples of the group formed by combining the pair of $R_{213}$ and $R_{214}$, the pair of $R_{214}$ and $R_{215}$ or the pair of $Y_{201}$ and $Y_{202}$ include a butylene group and a pentylene group.

The alkyl group as $R_{214}$, $R_{215}$, $Y_{201}$ and $Y_{202}$ is preferably a linear or branched alkyl group having a carbon number of 1 to 20. The alkyl group as $Y_{201}$ and $Y_{202}$ is more preferably a 2-oxoalkyl group having >C=O at the 2-position of the alkyl group, an alkoxycarbonylalkyl group (preferably with the alkoxy group having a carbon number of 2 to 20), or a carboxyalkyl group.

The cycloalkyl group as $R_{214}$, $R_{215}$, $Y_{201}$ and $Y_{202}$ is preferably a cycloalkyl group having a carbon number of 3 to 20.

The aryl group as $Y_{201}$ and $Y_{202}$ is preferably a phenyl group or a naphthyl group.

$Y_{201}$ and $Y_{202}$ each is preferably an alkyl group having a carbon number of 4 or more, more preferably from 4 to 12, still more preferably from 4 to 6.

At least either one of $R_{214}$ and $R_{215}$ is preferably an alkyl group, and more preferably, $R_{214}$ and $R_{215}$ both are an alkyl group.

In formula (A2), $R_{204}$ and $R_{205}$ each independently represents an aryl group, an alkyl group or a cycloalkyl group.

$X^-$ represents an anion of the compound represented by formula (I).

The aryl group of $R_{204}$ and $R_{205}$ is preferably a phenyl group or a naphthyl group, more preferably a phenyl group. The aryl group of $R_{204}$ and $R_{205}$ may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene).

The alkyl group as $R_{204}$ and $R_{205}$ may be either linear or branched and is preferably a linear or branched alkyl group having a carbon number of 1 to 10 (e.g., methyl, ethyl, propyl, butyl, pentyl).

The cycloalkyl group as $R_{204}$ and $R_{205}$ is preferably a cycloalkyl group having a carbon number of 3 to 10 (e.g., cyclopentyl, cyclohexyl, norbornyl).

$R_{204}$ and $R_{205}$ each may have a substituent, and examples of the substituent which $R_{204}$ and $R_{205}$ each may have include an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 15), an alkoxy group (for example, an alkoxy group having a carbon number of 1 to 15), a halogen atom, a hydroxyl group and a phenylthio group.

The compound (A) is preferably a compound represented by formula (A1), more preferably a compound represented by any one of formulae (A1a) to (A1c).

Specific examples of the compound (A) are set forth below, but the present invention is not limited thereto.

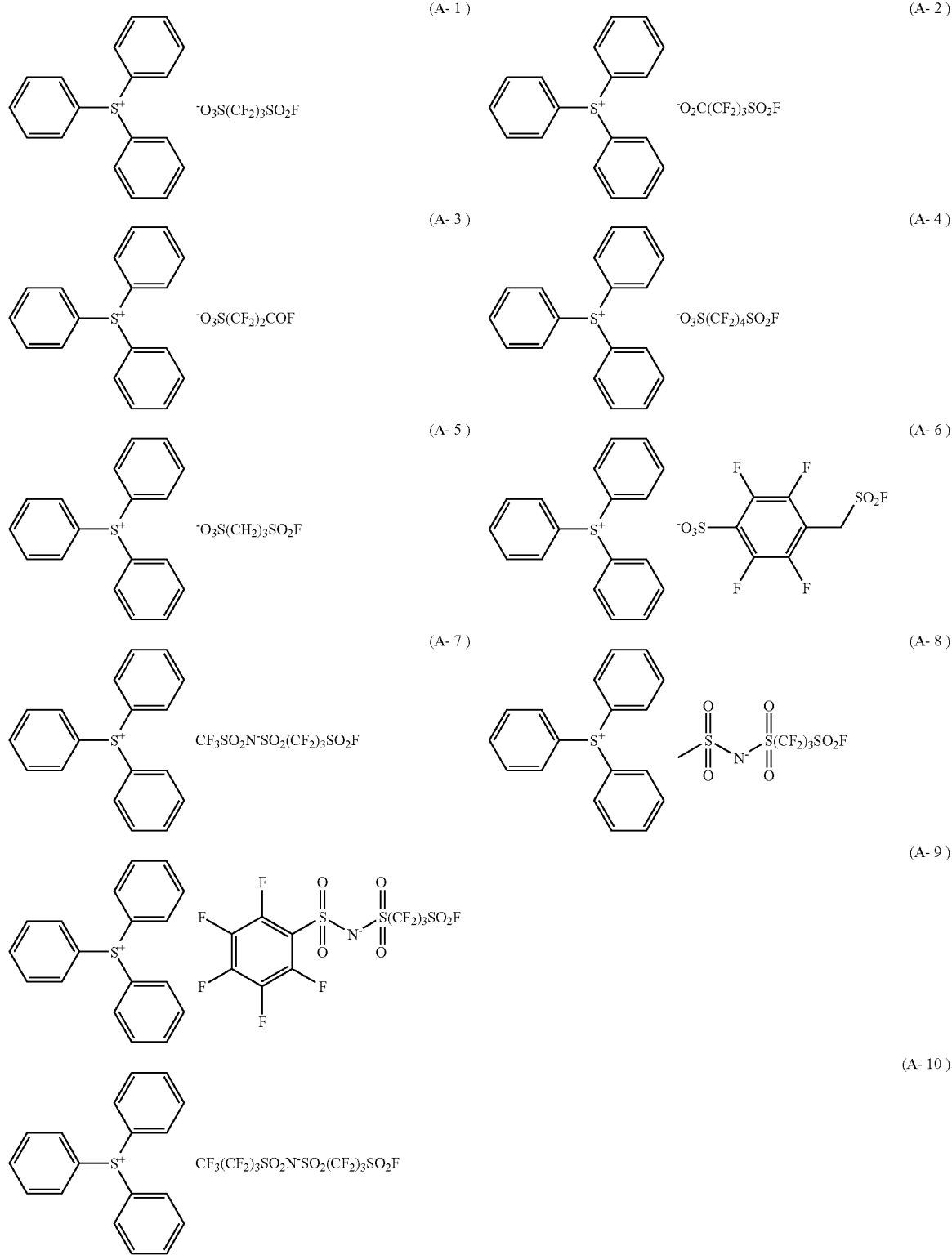

-continued
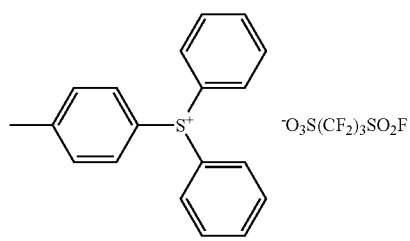 (A-11)
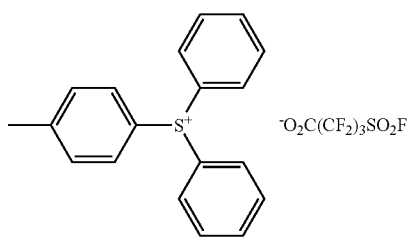 (A-12)
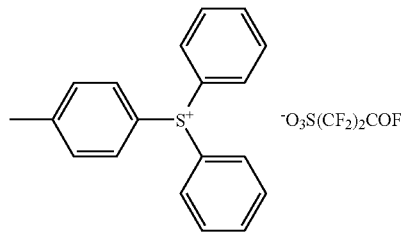 (A-13)
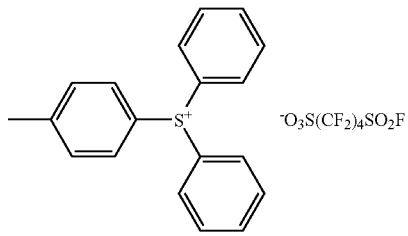 (A-14)
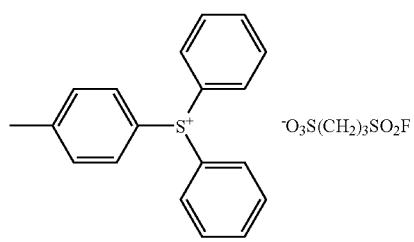 (A-15)
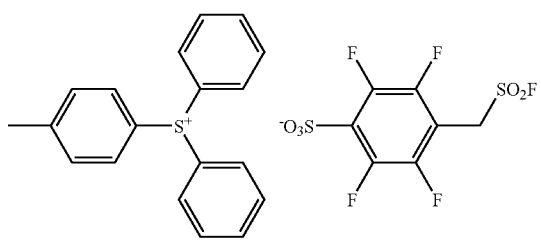 (A-16)
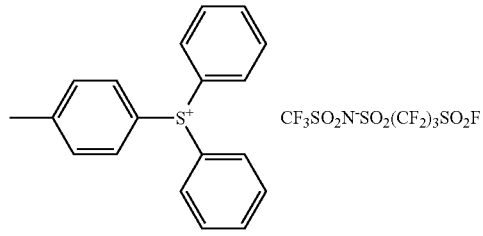 (A-17)
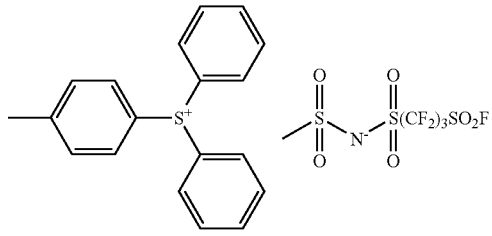 (A-18)
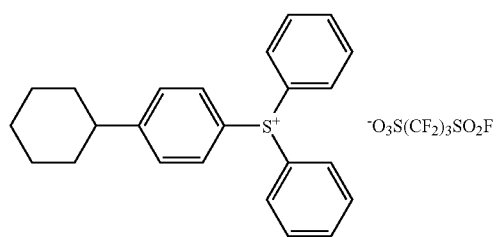 (A-19)
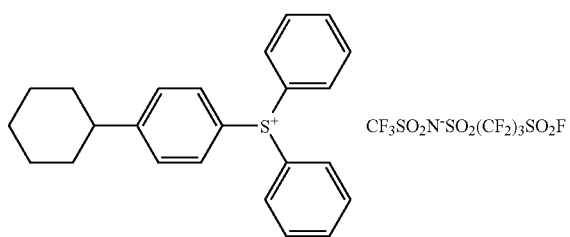 (A-20)
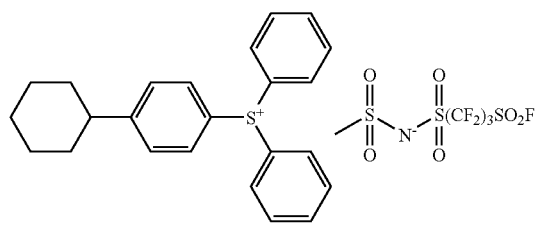 (A-21)
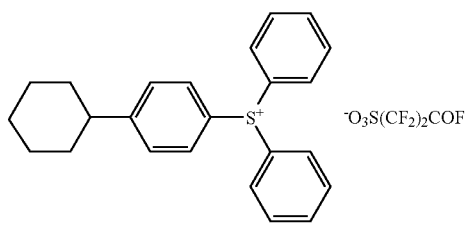 (A-22)

-continued
(A-23)
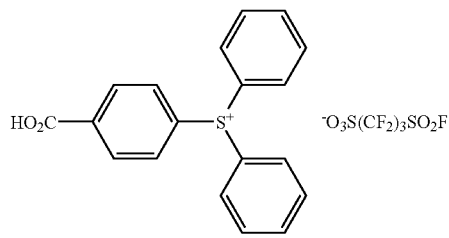
(A-24)
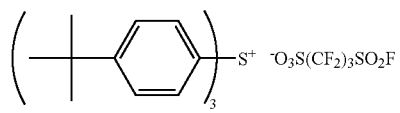
(A-25)
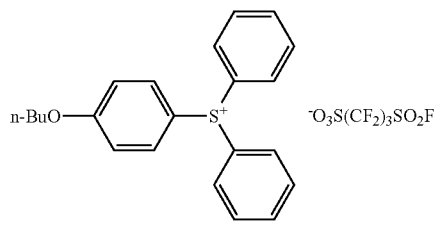
(A-26)
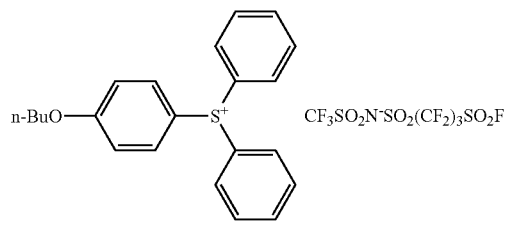
(A-27)
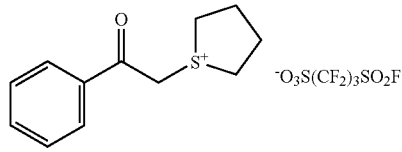
(A-28)
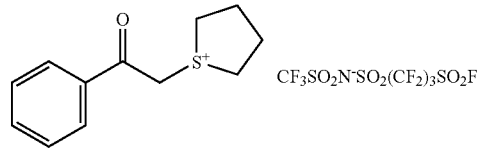
(A-29)
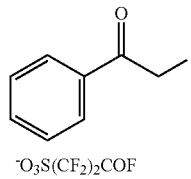
(A-30)
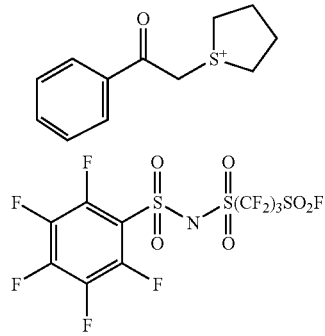
(A-31)
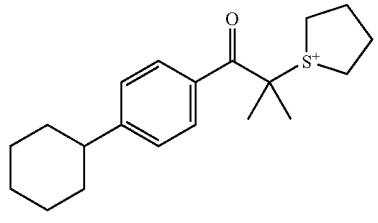
(A-32)
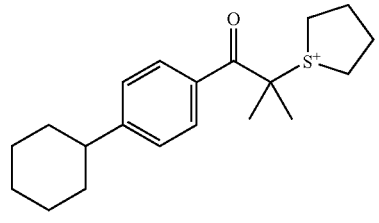
(A-33)
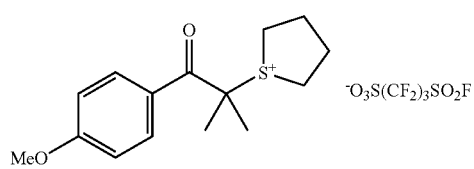
(A-34)
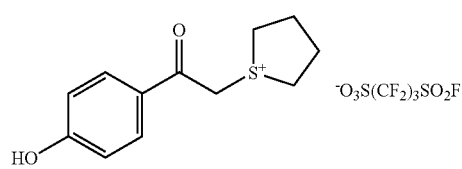
(A-35)
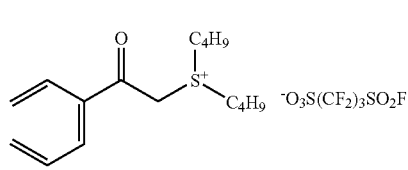
(A-36)
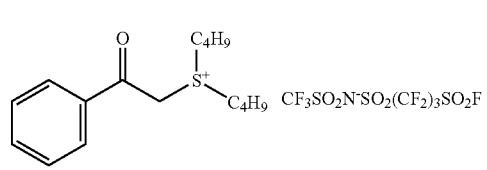

-continued (A-37) 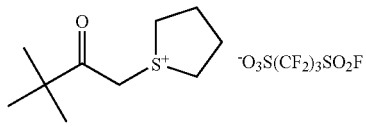

(A-38) 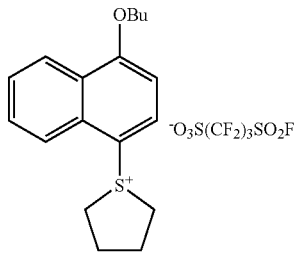

(A-39) 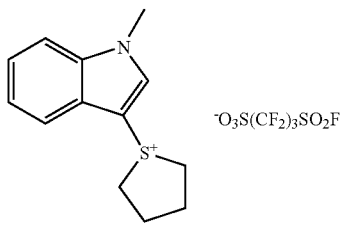

(A-40) 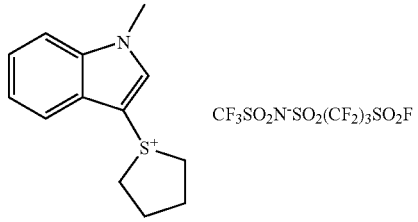

(A-41) 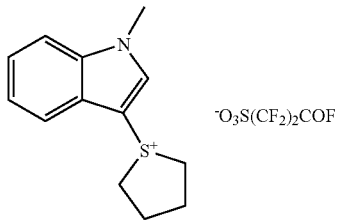

(A-42) 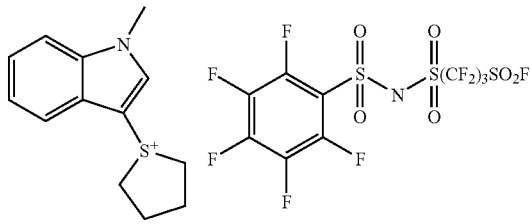

(A-43) 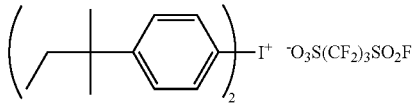

(A-44) 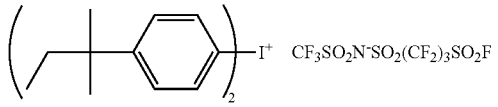

The content of the compound (A) in the photosensitive composition of the present invention is preferably from 0.1 to 20 mass %, more preferably from 0.1 to 10 mass %, based on the solid content of the composition. (In this specification, mass ratio is equal to weight ratio.)

[2] (B) Compound Capable of Generating an Acid Upon Irradiation with Actinic Rays or Radiation The photosensitive composition of the present invention preferably comprises, in addition to the compound (A), a compound capable of generating an acid upon irradiation with actinic rays or radiation (hereinafter sometimes referred to as an "acid generator").

The acid generator which can be used may be appropriately selected from a photoinitiator for photocationic polymerization, a photoinitiator for photoradical polymerization, a photo-decoloring agent for coloring matters, a photo-discoloring agent, a known compound capable of generating an acid upon irradiation with actinic rays or radiation, which is used for microresist and the like, and a mixture thereof.

Examples thereof include diazonium salt, phosphonium salt, sulfonium salt, iodonium salt, imidosulfonate, oxime sulfonate, diazodisulfone, disulfone and o-nitrobenzyl sulfonate.

Also, a compound where the above-described group or compound capable of generating an acid upon irradiation with actinic rays or radiation is introduced into the polymer main or side chain, such as compounds described in U.S. Pat. No. 3,849,137, German Patent 3,914,407, JP-A-63-26653, JP-A-55-164824, JP-A-62-69263, JP-A-63-146038, JP-A-63-163452, JP-A-62-153853 and JP-A-63-146029, may be used.

Furthermore, a compound capable of generating an acid by the effect of light described, for example, in U.S. Pat. No. 3,779,778 and European Patent 126,712 may also be used.

Among the compounds capable of generating an acid upon irradiation with actinic rays or radiation, preferred are the compounds represented by the following formulae (ZI), (ZII) and (ZIII):

ZI

ZII

ZIII

In formula (ZI), $R_{201}$, $R_{202}$ and $R_{203}$ each independently represents an organic group.

The number of carbons in the organic group as $R_{201}$, $R_{202}$ and $R_{203}$ is generally from 1 to 30, preferably from 1 to 20.

Two members out of $R_{201}$ to $R_{203}$ may combine to form a ring structure, and the ring may contain an oxygen atom, a sulfur atom, an ester bond, an amide bond or a carbonyl group. Examples of the group formed by combining two members out of $R_{201}$ to $R_{203}$ include an alkylene group (e.g., butylene, pentylene).

$Z^-$ represents a non-nucleophilic anion.

Examples of the non-nucleophilic anion as $Z^-$ include sulfonate anion, carboxylate anion, sulfonylimide anion, bis(alkylsulfonyl)imide anion and tris(alkylsulfonyl)methyl anion.

The non-nucleophilic anion is an anion having an extremely low ability of causing a nucleophilic reaction and this anion can suppress the decomposition in aging due to intramolecular nucleophilic reaction. By virtue of this anion, the aging stability of the resist is enhanced.

Examples of the sulfonate anion include aliphatic sulfonate anion, aromatic sulfonate anion and camphorsulfonate anion.

Examples of the carboxylate anion include aliphatic carboxylate anion, aromatic carboxylate anion and aralkylcarboxylate anion.

The aliphatic moiety in the aliphatic sulfonate anion may be an alkyl group or a cycloalkyl group but is preferably an alkyl group having a carbon number of 1 to 30 or a cycloalkyl group having a carbon number of 3 to 30, and examples thereof include a methyl group, an ethyl group, a propyl group, an isopropyl group, an n-butyl group, an isobutyl group, a sec-butyl group, a pentyl group, a neopentyl group, a hexyl group, a heptyl group, an octyl group, a nonyl group, a decyl group, an undecyl group, a dodecyl group, a tridecyl group, a tetradecyl group, a pentadecyl group, a hexadecyl group, a heptadecyl group, an octadecyl group, a nonadecyl group, an eicosyl group, a cyclopropyl group, a cyclopentyl group, a cyclohexyl group, an adamantyl group, a norbornyl group and a boronyl group.

The aromatic group in the aromatic sulfonate anion is preferably an aryl group having a carbon number of 6 to 14, and examples thereof include a phenyl group, a tolyl group and a naphthyl group.

The alkyl group, cycloalkyl group and aryl group in the aliphatic sulfonate anion and aromatic sulfonate anion each may have a substituent. Examples of the substituent for the alkyl group, cycloalkyl group and aryl group in the aliphatic sulfonate anion and aromatic sulfonate anion include a nitro group, a halogen atom (e.g., fluorine, chlorine, bromine, iodine), a carboxyl group, a hydroxyl group, an amino group, a cyano group, an alkoxy group (preferably having a carbon number of 1 to 5), a cycloalkyl group (preferably having a carbon number of 3 to 15), an aryl group (preferably having a carbon number of 6 to 14), an alkoxycarbonyl group (preferably having a carbon number of 2 to 7), an acyl group (preferably having a carbon number of 2 to 12) and an alkoxycarbonyloxy group (preferably having a carbon number of 2 to 7). As for the aryl group or ring structure in each group, examples of the substituent further include an alkyl group (preferably having a carbon number of 1 to 15).

Examples of the aliphatic moiety in the aliphatic carboxylate anion include the same alkyl groups and cycloalkyl groups as in the aliphatic sulfonate anion.

Examples of the aromatic group in the aromatic carboxylate anion include the same aryl group as in the aromatic sulfonate anion.

The aralkyl group in the aralkylcarboxylate anion is preferably an aralkyl group having a carbon number of 6 to 12, and examples thereof include a benzyl group, a phenethyl group, a naphthylmethyl group, a naphthylethyl group and a naphthylmethyl group.

The alkyl group, cycloalkyl group, aryl group and aralkyl group in the aliphatic carboxylate anion, aromatic carboxylate anion and aralkylcarboxylate anion each may have a substituent. Examples of the substituent for the alkyl group, cycloalkyl group, aryl group and aralkyl group in the aliphatic carboxylate anion, aromatic carboxylate anion and aralkylcarboxylate anion include the same halogen atom, alkyl group, cycloalkyl group, alkoxy group and alkylthio group as in the aromatic sulfonate anion.

Examples of the sulfonylimide anion include saccharin anion.

The alkyl group in the bis(alkylsulfonyl)imide anion and tris(alkylsulfonyl)methyl anion is preferably an alkyl group having a carbon number of 1 to 5, and examples thereof include a methyl group, an ethyl group, a propyl group, an isopropyl group, an n-butyl group, an isobutyl group, a sec-butyl group, a pentyl group and a neopentyl group. Examples of the substituent for such an alkyl group include a halogen atom, a halogen atom-substituted alkyl group, an alkoxy group and an alkylthio group. Among these, an alkyl group substituted by a fluorine atom is preferred.

Other examples of the non-nucleophilic anion include fluorinated phosphorus, fluorinated boron and fluorinated antimony.

The non-nucleophilic anion of $Z^-$ is preferably an aliphatic sulfonate anion with the sulfonic acid being substituted by a fluorine atom at the ax-position, an aromatic sulfonate anion substituted by a fluorine atom or a fluorine atom-containing group, a bis(alkylsulfonyl)imide anion with the alkyl group being substituted by a fluorine atom, or a tris(alkylsulfonyl)methide anion with the alkyl group being substituted by a fluorine atom, more preferably a perfluoroaliphatic sulfonate anion having a carbon number of 4 to 8, or a benzenesulfonate anion having a fluorine atom, still more preferably nonafluorobutanesulfonate anion, perfluorooctanesulfonate anion, pentafluorobenzenesulfonate anion, or 3,5-bis(trifluoromethyl)benzenesulfonate anion.

Examples of the organic group as $R_{201}$, $R_{202}$ and $R_{203}$ include the corresponding groups in the compounds (ZI-1), (ZI-2) and (ZI-3) described later.

The compound may be a compound having a plurality of structures represented by formula (Z1), for example, may be a compound having a structure that at least one of $R_{201}$ to $R_{203}$ in the compound represented by formula (Z1) is bonded to at least one of $R_{201}$ to $R_{203}$ in another compound represented by formula (Z1).

The component (Z1) is more preferably a compound (ZI-1), (ZI-2) or (ZI-3) described below.

The compound (ZI-1) is an arylsulfonium compound where at least one of $R_{201}$ to $R_{203}$ in formula (Z1) is an aryl group, that is, a compound having arylsulfonium as the cation.

In the arylsulfonium compound, $R_{201}$ to $R_{203}$ all may be an aryl group or a pail of $R_{201}$ to $R_{203}$ may be an aryl group with the remaining being an alkyl group or a cycloalkyl group.

Examples of the arylsulfonium compound include a triarylsulfonium compound, a diarylalkylsulfonium compound, an aryldialkylsulfonium compound, a diarylcycloalkyl-sulfonium compound and an aryldicycloalkylsulfonium compound.

The aryl group in the arylsulfonium compound is preferably a phenyl group or a naphthyl group, more preferably a phenyl group. The aryl group may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene). In the case where the arylsulfonium compound has two or more aryl groups, these two or more aryl groups may be the same of different.

The alkyl group or cycloalkyl group which is present, if desired, in the arylsulfonium compound is preferably a linear or branched alkyl group having a carbon number of 1 to 15 or a cycloalkyl group having a carbon number of 3 to 15, and examples thereof include a methyl group, an ethyl group, a propyl group, an n-butyl group, a sec-butyl group, a tert-butyl group, a cyclopropyl group, a cyclobutyl group and a cyclohexyl group.

The aryl group, alkyl group and cycloalkyl group of $R_{201}$ to $R_{203}$ each may have, as the substituent, an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 14), an alkoxy group (for example, an alkoxy group having a carbon number of 1 to 15), a halogen atom, a hydroxyl group or a phenylthio group. The substituent is preferably a linear or branched alkyl group having a carbon number of 1 to 12, a cycloalkyl group having a carbon number of 3 to 12, or a linear, branched or cyclic alkoxy group having a carbon number of 1 to 12, more preferably an alkyl group having a carbon number of 1 to 4, or an alkoxy group having a carbon number of 1 to 4. The substituent may be substituted to any one of three members $R_{201}$ to $R_{203}$ or may be substituted to all of these three members. In the case where $R_{201}$ to $R_{203}$ are an aryl group, the substituent is preferably substituted at the p-position of the aryl group.

The compound (ZI-2) is described below.

The compound (ZI-2) is a compound where $R_{201}$ to $R_{203}$ in formula (ZI) each independently represents an organic group having no aromatic ring. The aromatic ring as used herein includes an aromatic ring containing a heteroatom.

The organic group having no aromatic ring as $R_{201}$ to $R_{203}$ has a carbon number of generally from 1 to 30, preferably from 1 to 20.

$R_{201}$ to $R_{203}$ each independently represents preferably an alkyl group, a cycloalkyl group, an allyl group or a vinyl group, more preferably a linear or branched 2-oxoalkyl group, a 2-oxocycloalkyl group or an alkoxycarbonylmethyl group, still more preferably a linear or branched 2-oxoalkyl group.

The alkyl group or cycloalkyl group of $R_{201}$ to $R_{203}$ is preferably a linear or branched alkyl group having a carbon number of 1 to 10 (e.g., methyl, ethyl, propyl, butyl, pentyl) or a cycloalkyl group having a carbon number of 3 to 10 (e.g., cyclopentyl, cyclohexyl, norbornyl). The alkyl group is more preferably a 2-oxoalkyl group or an alkoxycarbonylmethyl group. The cycloalkyl group is more preferably a 2-oxocycloalkyl group.

The 2-oxoalkyl group may be either linear or branched and is preferably a group having >C=O at the 2-position of the above-described alkyl group.

The 2-oxocycloalkyl group is preferably a group having >C=O at the 2-position of the above-described cycloalkyl group.

The alkoxy group in the alkoxycarbonylmethyl group is preferably an alkoxy group having a carbon number of 1 to 5 (e.g., methoxy, ethoxy, propoxy, butoxy, pentoxy).

$R_{201}$ to $R_{203}$ each may be further substituted by a halogen atom, an alkoxy group (for example, an alkoxy group having a carbon number of 1 to 5), a hydroxyl group, a cyano group or a nitro group.

The compound (ZI-3) is a compound represented by the following formula (ZI-3), and this is a compound having a phenacylsulfonium salt structure.

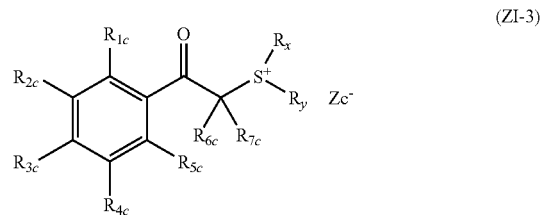

In formula (ZI-3), $R_{1c}$ to $R_{5c}$ each independently represents a hydrogen atom, an alkyl group, a cycloalkyl group, an alkoxy group or a halogen atom.

$R_{6c}$ and $R_{7c}$ each independently represents a hydrogen atom, an alkyl group or a cycloalkyl group.

$R_x$ and $R_y$ each independently represents an alkyl group, a cycloalkyl group, an allyl group or a vinyl group.

Any two or more members out of $R_{1c}$ to $R_{5c}$, the pair of $R_{6c}$ and $R_{7c}$ or the pair of $R_x$ and $R_y$ may combine with each other to form a ring structure, and the ring structure may contain an oxygen atom, a sulfur atom, an ester bond or an amide bond. Examples of the group formed by combining any two or more members out of $R_{1c}$ to $R_{5c}$ or combining the pair of $R_{6c}$ and $R_{7c}$ or the pair of $R_x$ and $R_y$ include a butylene group and a pentylene group.

Zc$^-$ represents a non-nucleophilic anion, and examples thereof are the same as those of the non-nucleophilic anion of $Z^-$ in formula (ZI).

The alkyl group as $R_{1c}$ to $R_{7c}$ may be either linear or branched and is, for example, an alkyl group having a carbon number of 1 to 20, preferably a linear or branched alkyl group having a carbon number of 1 to 12 (e.g., methyl, ethyl, linear or branched propyl, linear or branched butyl, linear or branched pentyl). The cycloalkyl group is, for example, a cycloalkyl group having a carbon number of 3 to 8 (e.g., cyclopentyl, cyclohexyl).

The alkoxy group as $R_{1c}$ to $R_{5c}$ may be linear, branched or cyclic and is, for example, an alkoxy group having a carbon number of 1 to 10, preferably a linear or branched alkoxy group having a carbon number of 1 to 5 (e.g., methoxy, ethoxy, linear or branched propoxy, linear or branched butoxy, linear or branched pentoxy), or a cyclic alkoxy group having a carbon number of 3 to 8 (e.g., cyclopentyloxy, cyclohexyloxy).

A compound where any one of $R_{1c}$ to $R_{5c}$ is a linear or branched alkyl group, a cycloalkyl group, or a linear, branched or cyclic alkoxy group, is preferred, and a compound where the sum of carbon numbers of $R_{1c}$ to $R_{5c}$ is from 2 to 15, is more preferred. In this case, the solubility in a solvent is more enhanced, and the generation of particles during storage can be suppressed.

Examples of the alkyl group and cycloalkyl group as $R_x$ and $R_y$ are the same as those of the alkyl group and cycloalkyl group in $R_{1c}$ to $R_{7c}$. Among these, a 2-oxoalkyl group, a 2-oxocycloalkyl group and an alkoxycarbonylmethyl group are preferred.

Examples of the 2-oxoalkyl group and 2-oxocycloalkyl group include a group having >C=O at the 2-position of the alkyl group or cycloalkyl group as $R_{1c}$ to $R_{7c}$.

Examples of the alkoxy group in the alkoxycarbonylmethyl group are the same as those of the alkoxy group in $R_{1c}$ to $R_{5c}$.

$R_x$ and $R_y$ each is preferably an alkyl or cycloalkyl group having a carbon number of 4 or more, more preferably 6 or more, still more preferably 8 or more.

In formulae (ZII) and (ZIII), $R_{204}$ to $R_{207}$ each independently represents an aryl group, an alkyl group or a cycloalkyl group.

The aryl group of $R_{204}$ to $R_{207}$ is preferably a phenyl group or a naphthyl group, more preferably a phenyl group. The aryl group of $R_{204}$ and $R_{207}$ may be an aryl group having a heterocyclic structure containing an oxygen atom, a nitrogen atom, a sulfur atom or the like. Examples of the aryl group having a heterocyclic structure include a pyrrole residue (a group formed by removing one hydrogen atom from a pyrrole), a furan residue (a group formed by removing one hydrogen atom from a furan), a thiophene residue (a group formed by removing one hydrogen atom from a thiophene), an indole residue (a group formed by removing one hydrogen atom from an indole), a benzofuran residue (a group formed by removing one hydrogen atom from a benzofuran) and a benzothiophene residue (a group formed by removing one hydrogen atom from a benzothiophene).

The alkyl group or cycloalkyl group in $R_{204}$ to $R_{207}$ is preferably a linear or branched alkyl group having a carbon number of 1 to 10 (e.g., methyl, ethyl, propyl, butyl, pentyl) or a cycloalkyl group having a carbon number of 3 to 10 (e.g., cyclopentyl, cyclohexyl, norbornyl).

The aryl group, alkyl group and cycloalkyl group of $R_{204}$ to $R_{207}$ each may have a substituent. Examples of the substituent which the aryl group, alkyl group and cycloalkyl group of $R_{204}$ to $R_{207}$ each may have include an alkyl group (for example, an alkyl group having a carbon number of 1 to 15), a cycloalkyl group (for example, a cycloalkyl group having a carbon number of 3 to 15), an aryl group (for example, an aryl group having a carbon number of 6 to 15), an alkoxy group (for example, an alkoxy group having a carbon number of 1 to 15), a halogen atom, a hydroxyl group and a phenylthio group.

$Z^-$ represents a non-nucleophilic anion, and examples thereof are the same as those of the non-nucleophilic anion of $Z^-$ in formula (ZI).

Other examples of the compound capable of generating an acid upon irradiation with actinic rays or radiation, which can be used, include the compounds represented by the following formulae (ZIV), (ZV) and (ZVI):

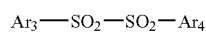

ZIV

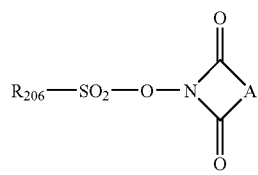

ZV

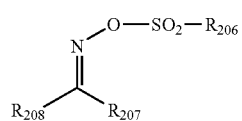

ZVI

In formulae (ZIV) to (ZVI), $Ar_3$ and $Ar_4$ each independently represents an aryl group.

$R_{206}$, $R_{207}$ and $R_{208}$ each independently represents an alkyl group, a cycloalkyl group or an aryl group.

A represents an alkylene group, an alkenylene group or an arylene group.

Among the compounds capable of generating an acid upon irradiation with actinic rays or radiation, more preferred are the compounds represented by formulae (ZI) to (ZIII).

The compound capable of generating an acid upon irradiation with actinic rays or radiation is preferably a compound capable of generating an acid having one sulfonic acid group or imide group, more preferably a compound capable of generating a monovalent perfluoroalkanesulfonic acid, a compound capable of generating a monovalent aromatic sulfonic acid substituted by a fluorine atom or a fluorine atom-containing group, or a compound capable of generating a monovalent imide acid substituted by a fluorine atom or a fluorine atom-containing group, still more preferably a sulfonium salt of fluoro-substituted alkanesulfonic acid, fluorine-substituted benzenesulfonic acid or fluorine-substituted imide acid. In particular, the acid generator which can be used preferably generates a fluoro-substituted alkanesulfonic acid, a fluoro-substituted benzenesulfonic acid or a fluoro-substituted imide acid, the acid having a pKa of −1 or less, and in this case, the sensitivity can be enhanced.

Among the compounds capable of generating an acid upon irradiation with actinic rays or radiation, particularly preferred compounds are set forth below.

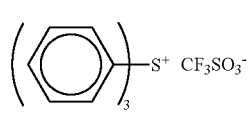

(z1)

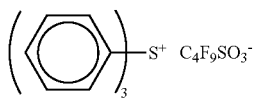

(z2)

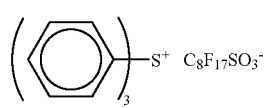

(z3)

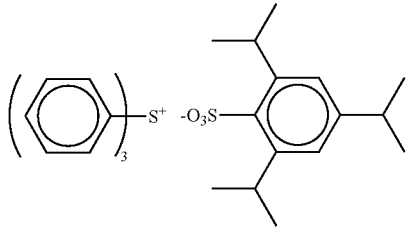

(z4)

-continued
(z5) 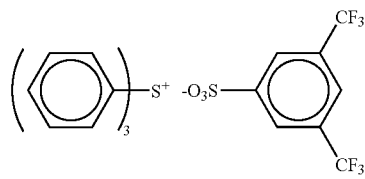
(z6) 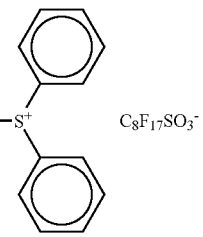
(z7) 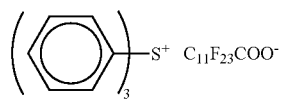
(z8) 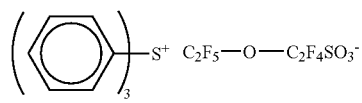
(z9) 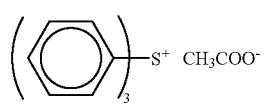
(z10) 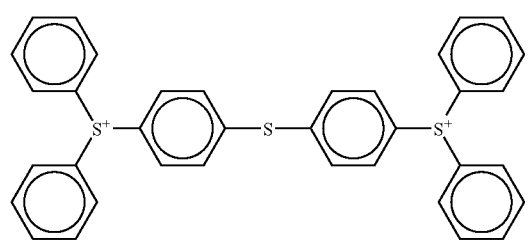 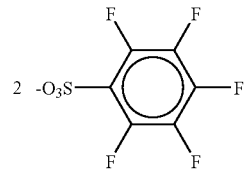
(z11) 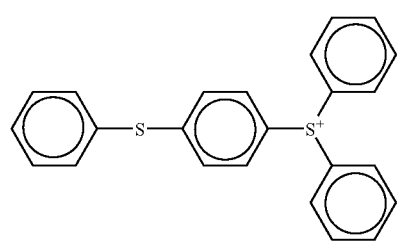 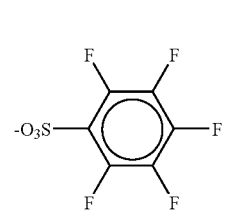
(z12) 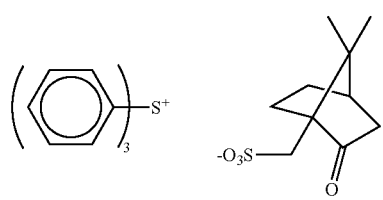
(z13) 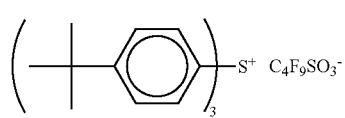
(z14) 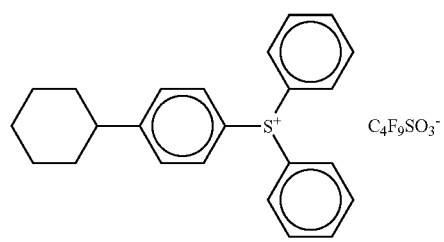
(z15) 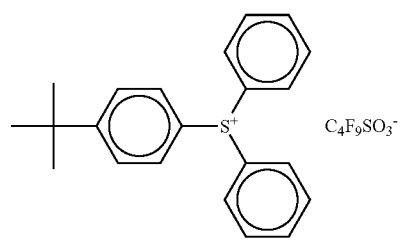
(z16) 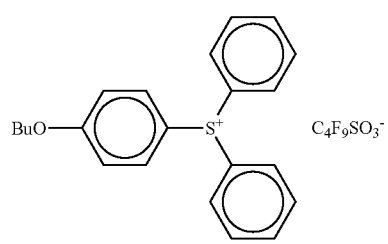
(Z17) 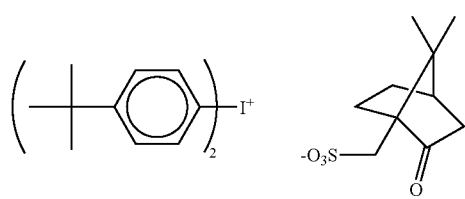

-continued

-continued
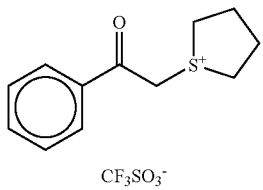 (z35)
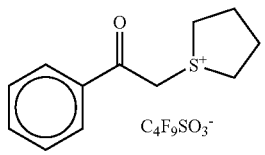 (z36)
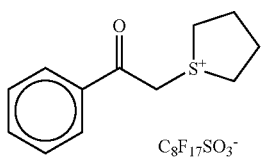 (z37)
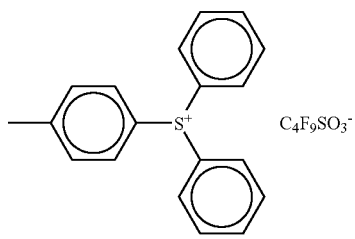 (z38)
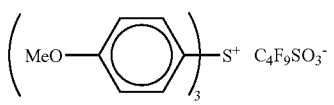 (z39)
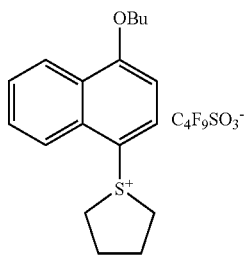 (z40)
 (z41)
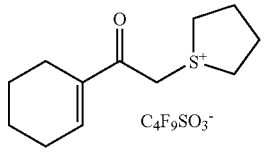 (z42)
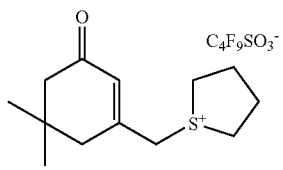 (z43)
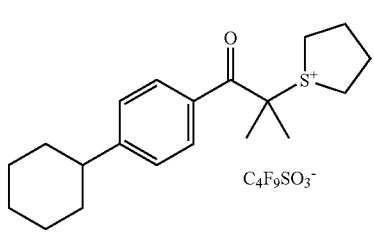 (z44)
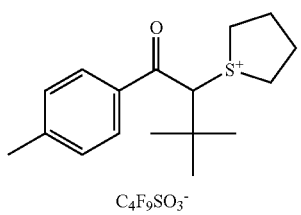 (z45)
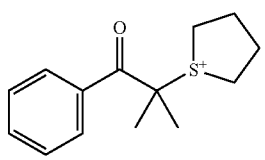 (z46)
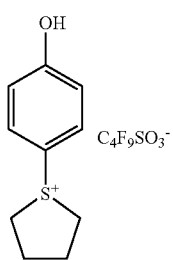 (z47)
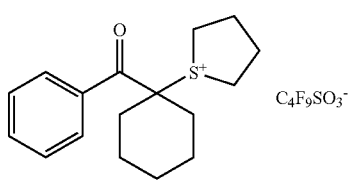 (z48)

-continued
(z49) 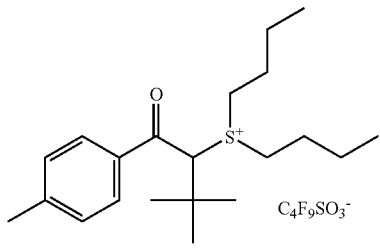
(z50) 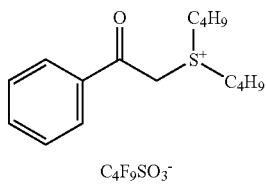
(z51) 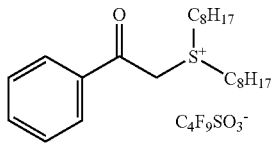
(z52) 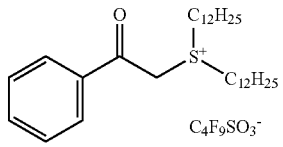
(z53) 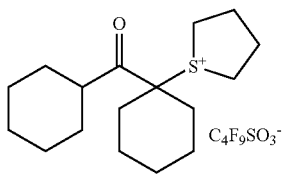
(z54) 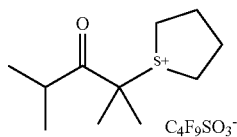
(z55) 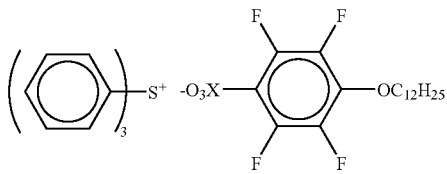
(z56) 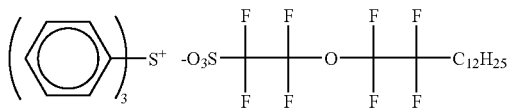
(z57) 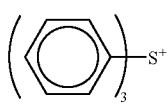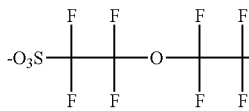
(z58) 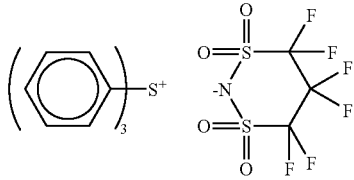
(z59) 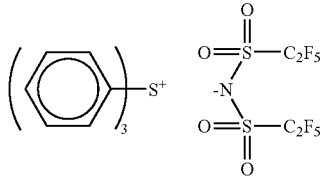
(Z60) 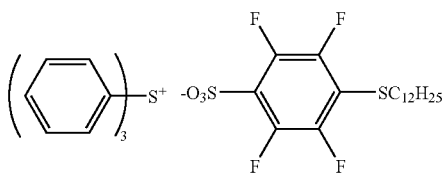
(Z61) 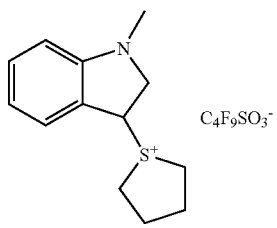
(Z62) 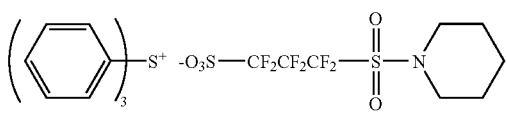
(Z63) 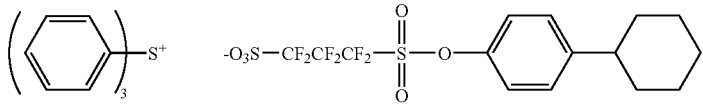

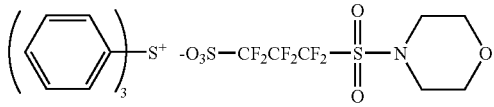

(Z64)

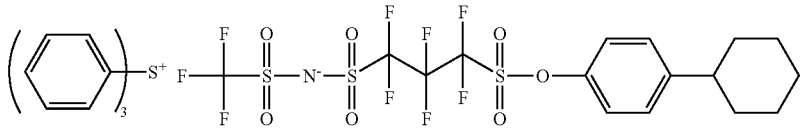

(Z65)

One acid generator may be used alone or two or more kinds of acid generators may be used in combination.

The content of the acid generator in the photosensitive composition is preferably from 0.1 to 20 mass %, more preferably from 0.5 to 10 mass %, still more-preferably from 1 to 7 mass %, based on the entire solid content of the photosensitive composition.

[3] (C) Resin Capable of Decomposing Under the Action of an Acid to Increase the Solubility in an Alkali Developer (Hereinafter Sometimes Referred to as a "Component (C)")

The resin capable of decomposing under the action of an acid to increase the solubility in an alkali developer, which is used in the positive photosensitive composition of the present invention, is a resin having a group capable of decomposing under the action of an acid (hereinafter sometimes referred to as an "acid-decomposable group"), in ether one or both of the main chain and the side chain of the resin. Of these, a resin having an acid-decomposable group in the side chain is preferred.

The group capable of decomposing under the action of an acid is preferably a group resulting from replacement of the hydrogen atom of a —COOH or —OH group by a group which splits off by the effect of an acid.

In the present invention, the acid-decomposable group is preferably an acetal group or a tertiary ester group.

In the case where the group capable of decomposing under the action of an acid is bonded as a side chain, the mother resin is an alkali-soluble resin having an —OH or —COOH group in the side chain. Examples thereof include an alkali-soluble resin described later.

The alkali dissolution rate of such an alkali-soluble resin is preferably 170 A/sec or more, more preferably 330 A/sec or more (A is angstrom), as measured (at 23° C.) in 0.261N tetramethylammonium hydroxide (TMAH).

From this standpoint, the alkali-soluble resin is preferably an alkali-soluble resin having a hydroxystyrene structural unit, such as o-, m- or p-poly(hydroxystyrene) or copolymer thereof, hydrogenated poly(hydroxystyrene), halogen- or alkyl-substituted poly(hydroxystyrene), partially O-alkylated or O-acylated poly(hydroxystyrene), styrene-hydroxystyrene copolymer, α-methylstyrene-hydroxystyrene copolymer and hydrogenated novolak resin; or an alkali-soluble resin containing a repeating unit having a carboxyl group, such as (meth)acrylic acid and norbornene carboxylic acid.

Preferred examples of the repeating unit having an acid-decomposable group for use in the present invention include tert-butoxycarbonyloxystyrene, 1-alkoxyethoxystyrene and tertiary alkyl (meth)acrylate. Among these, 2-alkyl-2-adamantyl (meth)acrylate and dialkyl(1-adamantyl)methyl (meth)acrylate are more preferred.

The component (C) for use in the present invention can be obtained by reacting an acid-decomposable group precursor with an alkali-soluble resin or copolymerizing an acid-decomposable group-bonded alkali-soluble resin monomer with various monomers, and this is disclosed in European Patent 254853, JP-A-2-25850, JP-A-3-223860 and JP-A-4-251259.

In the case of irradiating the positive photosensitive composition of the present invention with KrF excimer laser light, electron beam, X-ray or high-energy beam at a wavelength of 50 nm or less (e.g., EUV), the resin as the component (C) preferably has a hydroxystyrene repeating unit, and the resin is more preferably a copolymer of hydroxystyrene/hydroxystyrene protected by an acid-decomposable group, or hydroxystyrene/tertiary alkyl methacrylate.

Specific examples of the component (C) for use in the present invention are set forth below, but the present invention is not limited thereto.

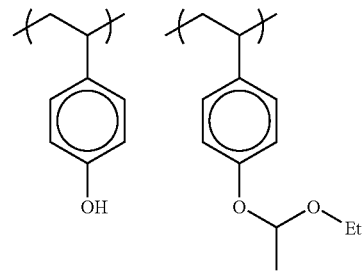

(R-1)

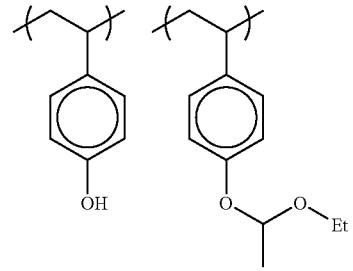

(R-2)

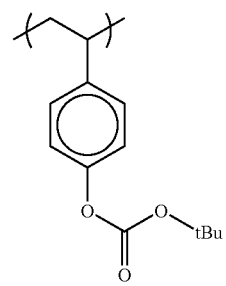

(R-3)
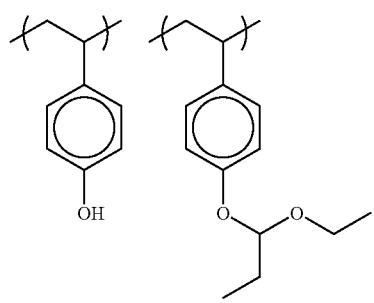
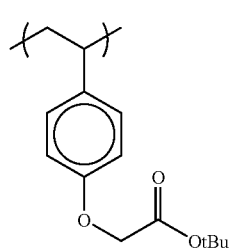
(R-4)
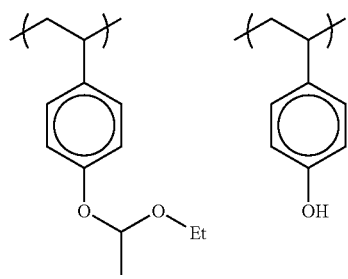
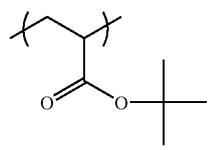
(R-5)
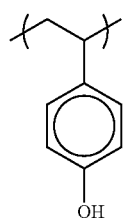
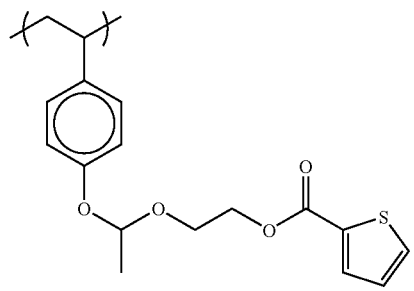
(R-6)
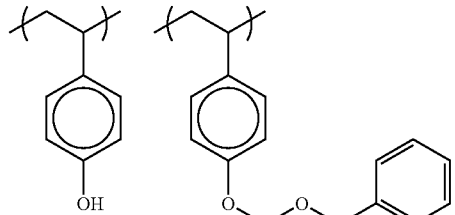
(R-7)
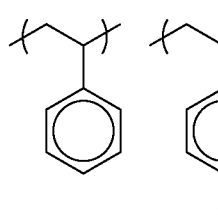
(R-8)
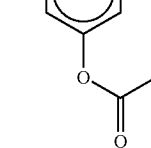
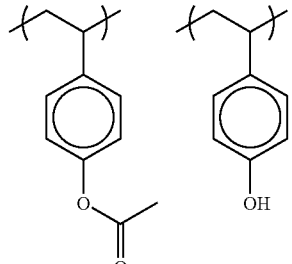
(R-9)
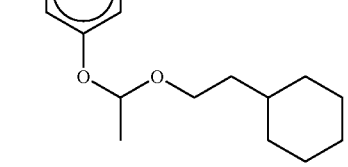
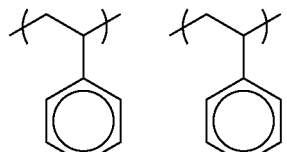
(R-10)
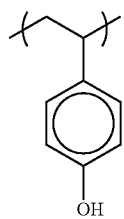

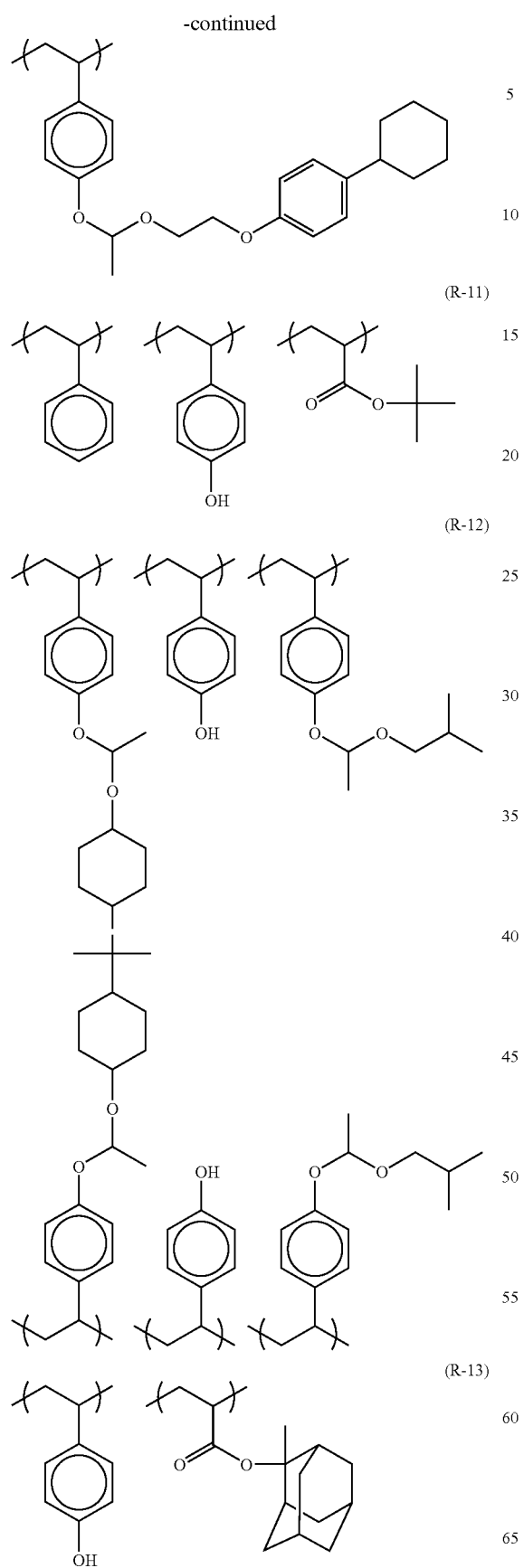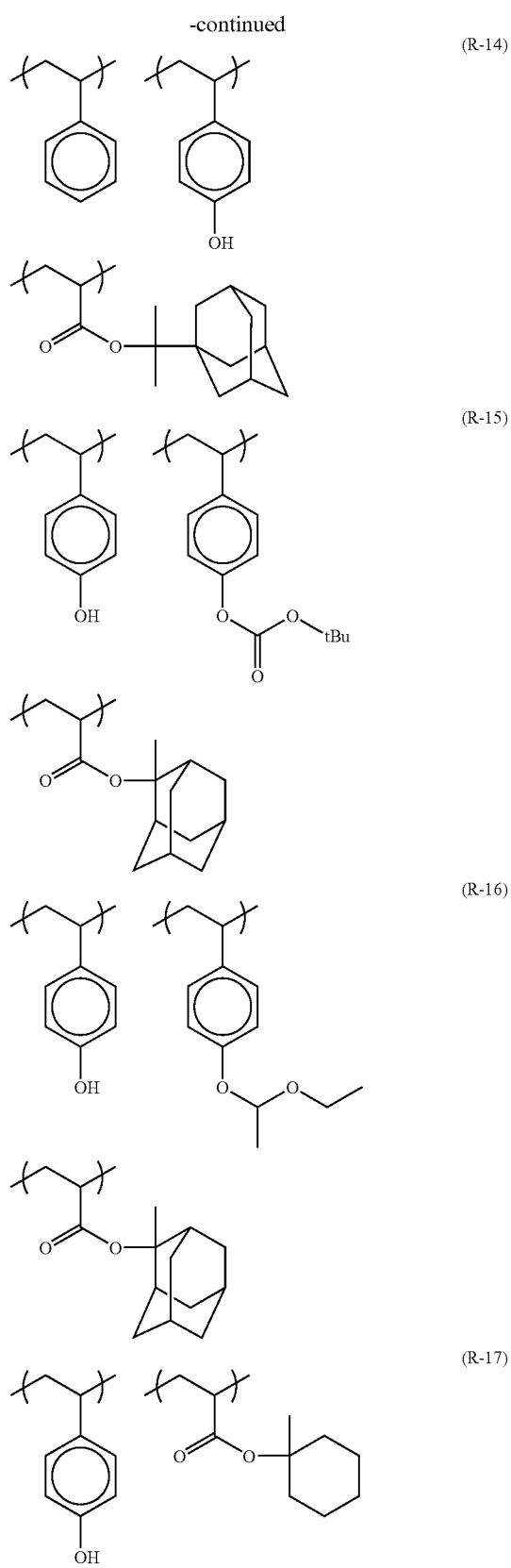
In these specific examples, "tBu" indicates a tert-butyl group.

The content of the group capable of decomposing under the action of an acid is expressed by B/(B+S) using the number (B) of acid-decomposable groups in the resin and the number (S) of alkali-soluble groups not protected by a group which splits off by the effect of an acid. The content is preferably from 0.01 to 0.7, more preferably from 0.05 to 0.50, still more preferably from 0.05 to 0.40.

In the case of irradiating the positive photosensitive composition of the present invention with ArF excimer laser light, the resin as the component (C) is preferably a resin having a monocyclic or polycyclic alicyclic hydrocarbon structure and undergoing decomposition under the action of an acid to increase the solubility in an alkali developer.

The resin having a monocyclic or polycyclic alicyclic hydrocarbon structure and undergoing decomposition under the action of an acid to increase the solubility in an alkali developer (hereinafter sometimes referred to as an "alicyclic hydrocarbon-based acid-decomposable resin") is preferably a resin containing at least one repeating unit selected from the group consisting of a repeating unit having an alicyclic hydrocarbon-containing partial structure represented by any one of the following formulae (pI) to (pV), and a repeating unit represented by the following formula (II-AB):

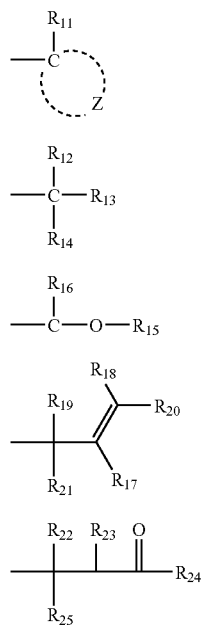

In formulae (pI) to (pV), $R_{11}$ represents a methyl group, an ethyl group, an n-propyl group, an isopropyl group, an n-butyl group, an isobutyl group or a sec-butyl group. Z represents an atomic group necessary for forming a cycloalkyl group together with the carbon atom.

$R_{12}$ to $R_{16}$ each independently represents a linear or branched alkyl group having a carbon number of 1 to 4 or a cycloalkyl group, provided that at least one of $R_{12}$ to $R_{14}$ or either one of $R_{15}$ and $R_{16}$ represents a cycloalkyl group.

$R_{17}$ to $R_{21}$ each independently represents a hydrogen atom, a linear or branched alkyl group having a carbon number of 1 to 4 or a cycloalkyl group, provided that at least one of $R_{17}$ to $R_{21}$ represents a cycloalkyl group and that either one of $R_{19}$ and $R_{21}$ represents a linear or branched alkyl group having a carbon number of 1 to 4 or a cycloalkyl group.

$R_{22}$ to $R_{25}$ each independently represents a hydrogen atom, a linear or branched alkyl group having a carbon number of 1 to 4 or a cycloalkyl group, provided that at least one of $R_{22}$ to $R_{25}$ represents a cycloalkyl group. $R_{23}$ and $R_{24}$ may combine with each other to form a ring.

(II-AB)

In formula (II-AB), $R_{11}'$ and $R_{12}'$ each independently represents a hydrogen atom, a cyano group, a halogen atom or an alkyl group.

Z' represents an atomic group for forming an alicyclic structure including two bonded carbon atoms (C—C).

Formula (I-AB) is preferably the following formula (II-AB1) or (II-AB2).

(II-AB1)

(II-AB2)

In formulae (II-AB1) and (II-AB2), $R_{13}'$ to $R_{16}'$ each independently represents a hydrogen atom, a halogen atom, a cyano group, a hydroxyl group, —COOH, —COOR$_5$, a group capable of decomposing under the action of an acid, —C(=O)—X-A'-R$_{17}'$, an alkyl group or a cycloalkyl group, and at least two members out of $R_{13}'$ to $R_{16}'$ may combine to form a ring.

$R_5$ represents an alkyl group, a cycloalkyl group or a group having a lactone structure.

X represents an oxygen atom, a sulfur atom, —NH—, —NHSO$_2$— or —NHSO$_2$NH—.

A' represents a single bond or a divalent linking group.

$R_{17}'$ represents —COOH, —COOR$_5$, —CN, a hydroxyl group, an alkoxy group, —CO—NH—R$_6$, —CO—NH—SO$_2$—R$_6$ or a group having a lactone structure.

$R_6$ represents an alkyl group or a cycloalkyl group.

n represents 0 or 1.

In formulae (pI) to (pV), the alkyl group of $R_{12}$ to $R_{25}$ is a linear or branched alkyl group having from 1 to 4 carbon atoms, and examples thereof include a methyl group, an ethyl group, a propyl group, an n-butyl group, a sec-butyl group and a tert-butyl group.

The cycloalkyl group of $R_{11}$ to $R_{25}$ and the cycloalkyl group formed by Z together with the carbon atom may be monocyclic or polycyclic. Specific examples thereof include a group having a monocyclo, bicyclo, tricyclo or tetracyclo structure or the like with a carbon number of 5 or more. The carbon number thereof is preferably from 6 to 30, more preferably from 7 to 25. These cycloalkyl groups each may have a substituent.

Preferred examples of the cycloalkyl group include an adamantyl group, a noradamantyl group, a decalin residue, a tricyclodecanyl group, a tetracyclododecanyl group, a norbornyl group, a cedrol group, a cyclopentyl group, a cyclohexyl group, a cycloheptyl group, a cyclooctyl group, a cyclodecanyl group and a cyclododecanyl group. Among these, more preferred are an adamantyl group, a norbornyl group, a cyclohexyl group, a cyclopentyl group, a tetracyclododecanyl group and a tricyclodecanyl group.

These alkyl group and cycloalkyl group each may further have a substituent. Examples of the substituent which the alkyl group and cycloalkyl group may further have include an alkyl group (having a carbon number of 1 to 4), a halogen atom, a hydroxyl group, an alkoxy group (having a carbon number of 1 to 4), a carboxyl group and an alkoxycarbonyl group (having a carbon number of 2 to 6). These alkyl group, alkoxy group, alkoxycarbonyl group and the like each may further have a substituent. Examples of the substituent which the alkyl group, alkoxy group, alkoxycarbonyl group and the like may further have include a hydroxyl group, a halogen atom and an alkoxy group.

The structures represented by formulae (pI) to (pV) each can be used for the protection of an alkali-soluble group in the resin. Examples of the alkali-soluble group include various groups known in this technical field.

Specific examples thereof include a structure where the hydrogen atom of a carboxylic acid group, a sulfonic acid group, a phenol group or a thiol group is replaced by the structure represented by any one of formulae (pI) to (pV). Among these, preferred is a structure where the hydrogen atom of a carboxylic acid group or a sulfonic acid group is replaced by the structure represented by any one of formulae (pI) to (pV).

The repeating unit having an alkali-soluble group protected by the structure represented by any one of formulae (pI) to (pV) is preferably a repeating unit represented by the following formula (pA):

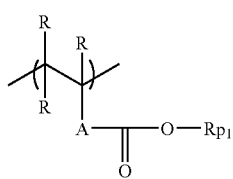

(PA)

In formula (pA), R represents a hydrogen atom, a halogen atom or a linear or branched alkyl group having a carbon number of 1 to 4, and the plurality of R's may be the same or different.

A represents a single bond, or a sole group or a combination of two or more groups, selected from the group consisting of an alkylene group, an ether group, a thioether group, a carbonyl group, an ester group, an amido group, a sulfonamido group, a urethane group and a urea group. A is preferably a single bond.

$Rp_1$ represents any one group of formulae (pI) to (pV).

The repeating unit represented by formula (pA) is most preferably a repeating unit comprising a 2-alkyl-2-adamantyl (meth)acrylate or a dialkyl(1-adamantyl)methyl (meth)acrylate.

Specific examples of the repeating unit represented by formula (pA) are set forth below.

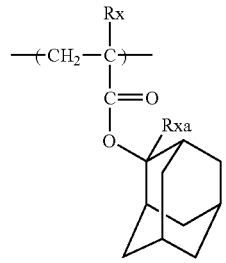

1

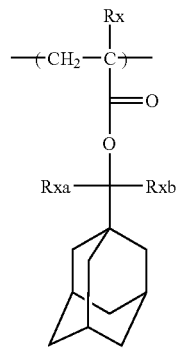

2

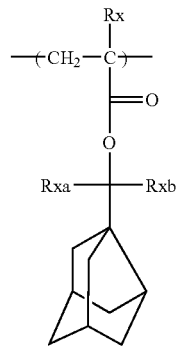

3

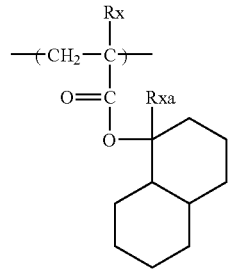

4

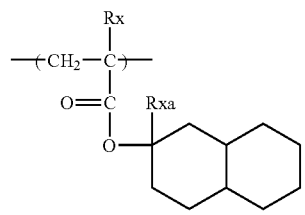

5

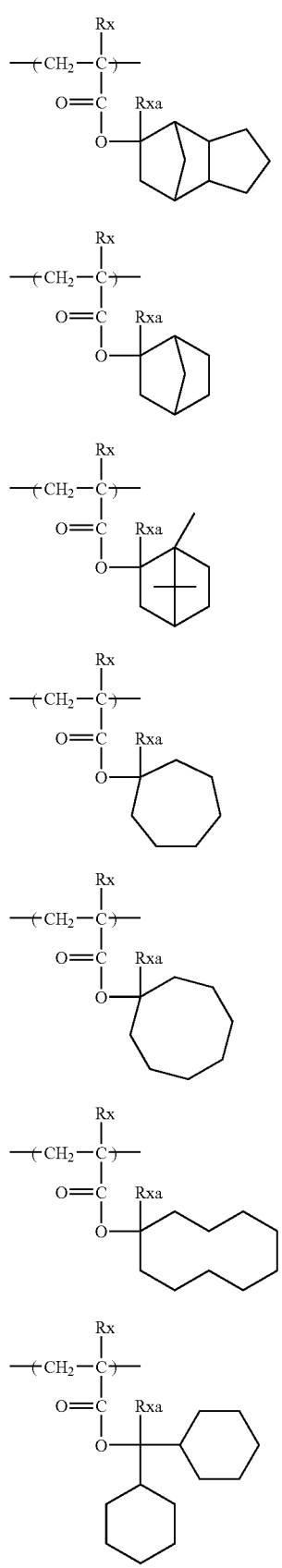
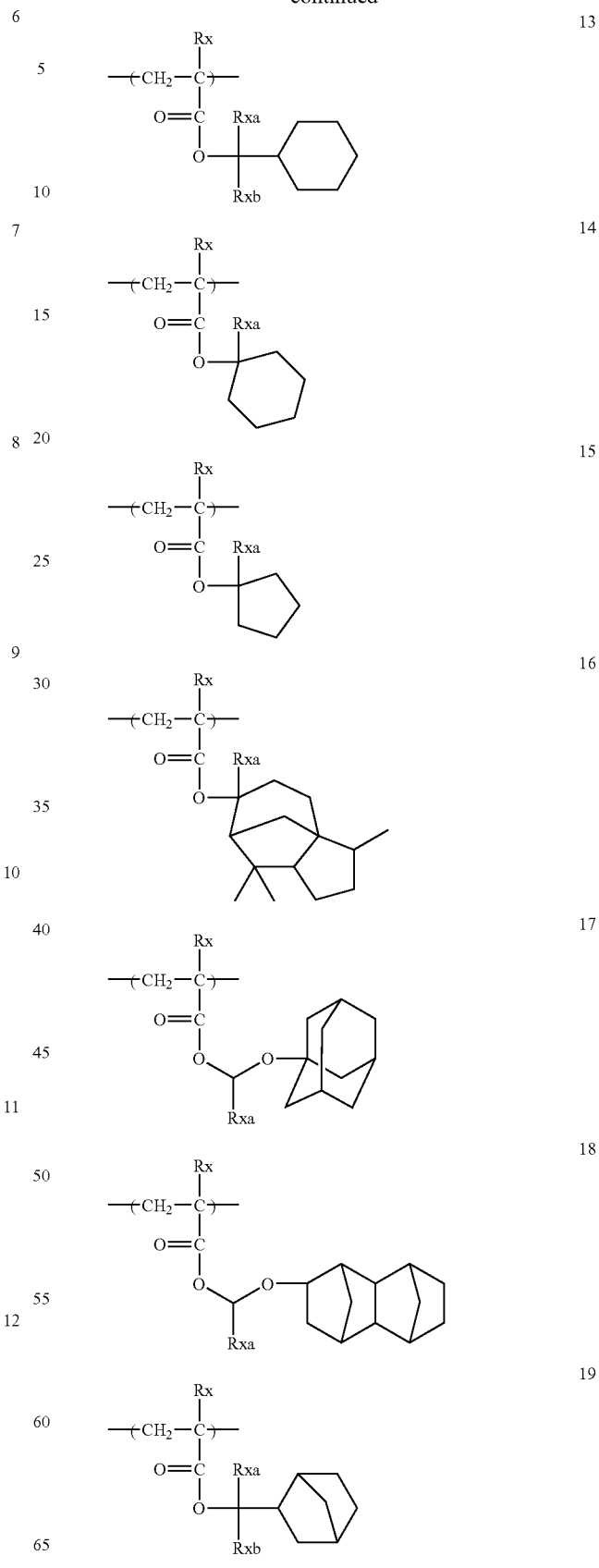

In the formulae above, Rx represents H, CH$_3$, CF$_3$ or CH$_2$OH, and Rxa and Rxb each independently represents an alkyl group having a carbon number of 1 to 4.

Examples of the halogen atom of R$_{11}$' and R$_{12}$' in formula (II-AB) include a chlorine atom, a bromine atom, a fluorine atom and an iodine atom.

The alkyl group of R$_{11}$' and R$_{12}$' is preferably a linear or branched alkyl group having a carbon number of 1 to 10, and examples thereof include a methyl group, an ethyl group, an n-propyl group, an isopropyl group and a linear or branched butyl, pentyl, hexyl or heptyl group.

The atomic group for forming an alicyclic structure of Z' is an atomic group of forming, in the resin, an alicyclic hydrocarbon repeating unit which may have a substituent, and in particular, an atomic group for forming a crosslinked alicyclic structure of giving a crosslinked alicyclic hydrocarbon repeating unit is preferred.

Examples of the skeleton of the alicyclic hydrocarbon formed are the same as those of the cycloalkyl group of R$_{12}$ to R$_{25}$ in formulae (pI) to (pVI).

The alicyclic hydrocarbon skeleton may have a substituent, and examples of the substituent include R$_{13}$' to R$_{16}$' in formulae (II-AB1) and (II-AB2).

In the alicyclic hydrocarbon-based acid-decomposable resin for use in the present invention, the group capable of decomposing under the action of an acid may be contained in at least one repeating unit out of the repeating unit having an alicyclic hydrocarbon-containing partial structure represented by any one of formulae (pI) to (pV), the repeating unit represented by formula (II-AB), and the repeating unit comprising a copolymerization component described later.

Various substituents R$_{13}$' to R$_{16}$' in formulae (II-AB1) and (II-AB2) may work out to a substituent of an atomic group for forming an alicyclic structure in formula (II-AB) or an atomic group Z for forming a crosslinked alicyclic structure.

Specific examples of the repeating units represented by formulae (II-AB 1) and (II-AB2) are set forth below, but the present invention is not limited thereto.

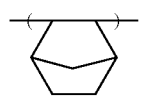
[II-1]

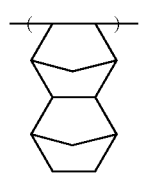
[II-2]

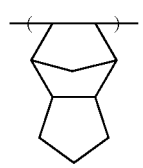
[II-3]

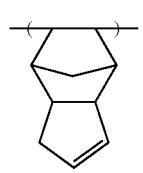
[II-4]

-continued

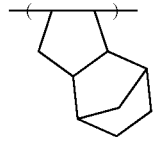
[II-5]

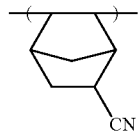
[II-6]

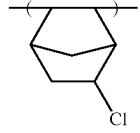
[II-7]

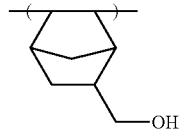
[II-8]

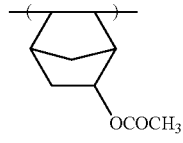
[II-9]

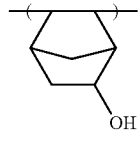
[II-10]

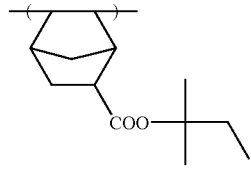
[II-11]

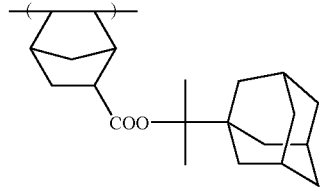
[II-12]

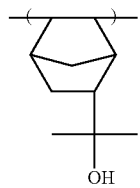
[II-13]

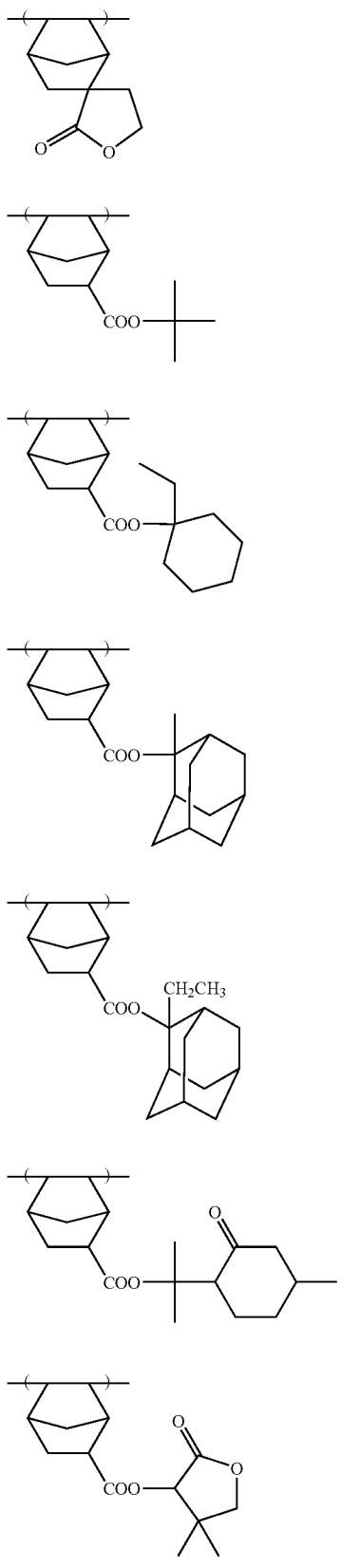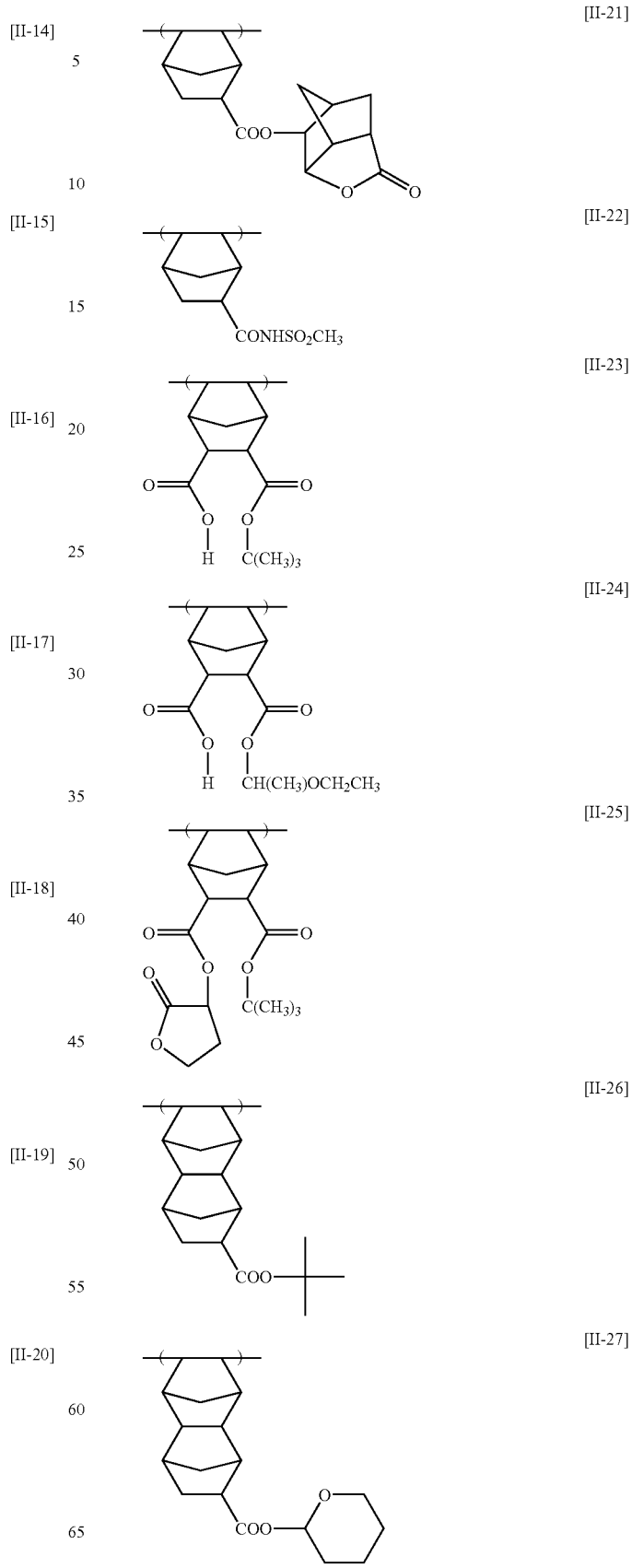

-continued

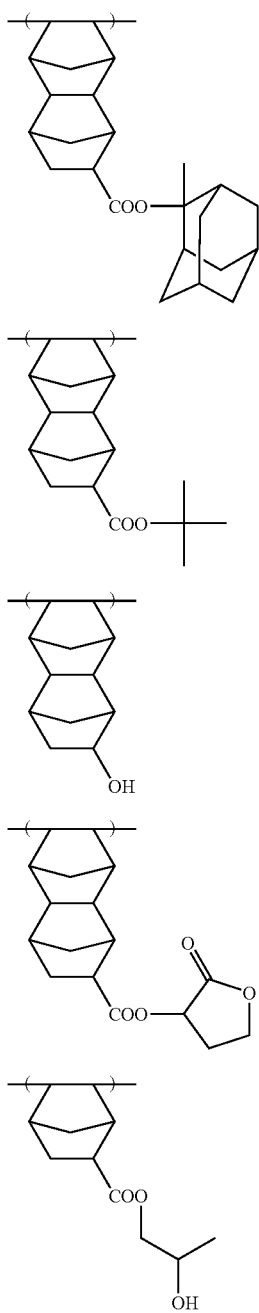

The alicyclic hydrocarbon-based acid-decomposable resin for use in the present invention preferably contains a repeating unit having a lactone group. As for the lactone group, any group may be used as long as it has a lactone structure, but a group having a 5-, 6- or 7-membered ring lactone structure is preferred. The 5-, 6- or 7-membered ring lactone structure is preferably condensed with another ring structure in the form of forming a bicyclo or spiro structure. The alicyclic hydrocarbon-based acid-decomposable resin for use in the present invention more preferably has a repeating unit containing a group having a lactone structure represented by any one of the following formulae (LC1-1) to (LC1-16). The group having a lactone structure may be bonded directly to the main chain.

Among these lactone structures, (LC1-1), (LC1-4), (LC1-5), (LC1-6), (LC1-13) and (LC1-14) are preferred. By virtue of using a specific lactone structure, the line edge roughness and the development defect are improved.

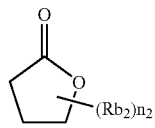
LC1-1

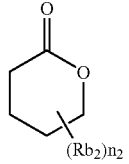
LC1-2

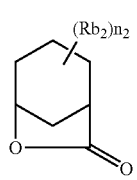
LC1-3

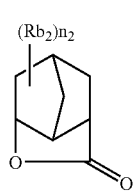
LC1-4

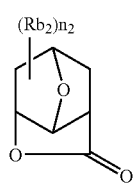
LC1-5

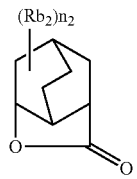
LC1-6

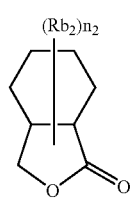
LC1-7

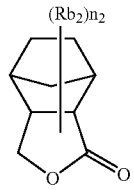
LC1-8

-continued

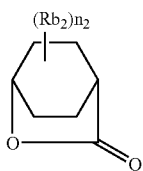
LC1-9

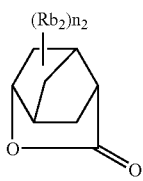
LC1-10

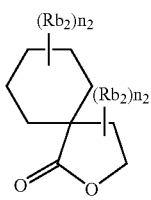
LC1-11

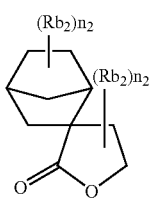
LC1-12

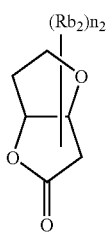
LC1-13

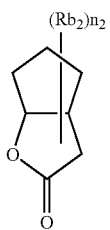
LC1-14

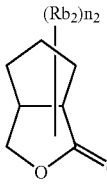
LC1-15

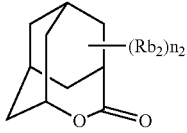
LC1-16

The lactone structure moiety may or may not have a substituent ($Rb_2$). Preferred examples of the substituent ($Rb_2$) include an alkyl group having a carbon number of 1 to 8, a cycloalkyl group having a carbon number of 3 to 7, an alkoxy group having a carbon number of 1 to 8, an alkoxycarbonyl group having a carbon number of 1 to 8, a carboxyl group, a halogen atom, a hydroxyl group, a cyano group and an acid-decomposable group. n2 represents an integer of 0 to 4. When $n_2$ is an integer of 2 or more, the plurality of $Rb_2$'s may be the same or different and also, the plurality of $Rb_2$'s may combine with each other to form a ring.

Examples of the repeating unit containing a group having a lactone structure represented by any one of formulae (LC1-1) to (LC1-16) include a repeating unit where at least one of $R_{13}'$ to $R_{16}'$ in formula (II-AB1) or (II-AB2) has a group represented by any one of formulae (LC1-1) to (LC1-16) (for example, $R_5$ of —$COOR_5$ is a group represented by any one of formulae (LC1-1) to (LC1-16)), and a repeating unit represented by the following formula (AI):

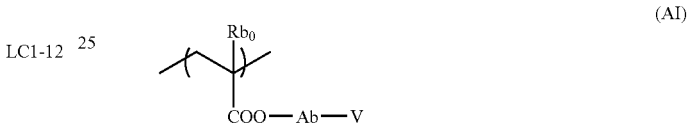

(AI)

In formula (AI), $Rb_0$ represents a hydrogen atom, a halogen atom or an alkyl group having a carbon number of 1 to 4.

Examples of the alkyl group of $Rb_0$ include a methyl group, an ethyl group, a propyl group, an n-butyl group, a sec-butyl group and a tert-butyl group. The alkyl group of $Rb_0$ may have a substituent. Preferred examples of the substituent which the alkyl group of $Rb_0$ may have include a hydroxyl group and a halogen atom.

Examples of the halogen atom of $Rb_0$ include a fluorine atom, a chlorine atom, a bromine atom and an iodine atom. $Rb_0$ is preferably a hydrogen atom or a methyl group.

Ab represents an alkylene group, a divalent linking group having a monocyclic or polycyclic alicyclic hydrocarbon structure, a single bond, an ether group, an ester group, a carbonyl group, a carboxyl group, or a divalent group comprising a combination thereof, preferably a single bond or a linking group represented by -$Ab_1$-$CO_2$—.

$Ab_1$ is a linear or branched alkylene group or a monocyclic or polycyclic cycloalkylene group, preferably a methylene group, an ethylene group, a cyclohexyl residue, an adamantyl residue or a norbornyl residue.

V represents a group represented by any one of formulae (LC1-1) to (LC1-16).

The repeating unit having a lactone structure usually has an optical isomer, but any optical isomer may be used. One optical isomer may be used alone or a mixture of a plurality of optical isomers may be used. In the case of mainly using one optical isomer, the optical purity (ee) thereof is preferably 90 or more, more preferably 95 or more.

Specific examples of the repeating unit containing a group having a lactone structure are set forth below, but the present invention is not limited thereto.

(In the formulae, Rx is H, $CH_3$, $CH_2OH$ or $CF_3$.)

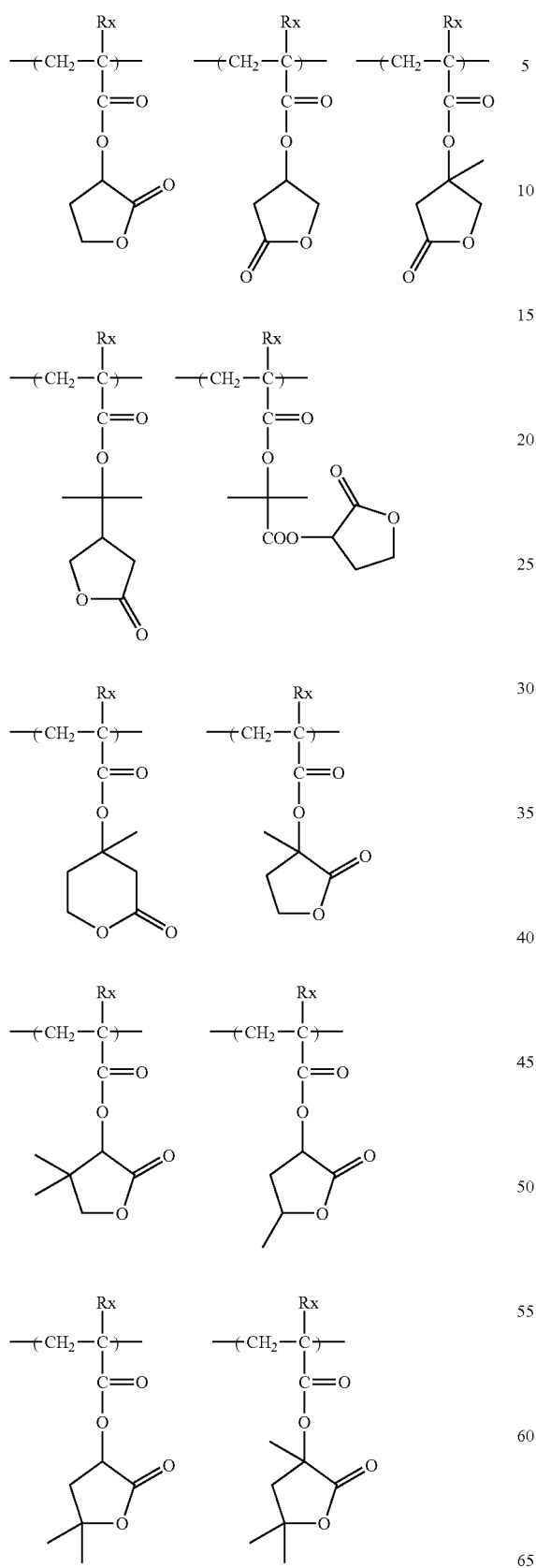
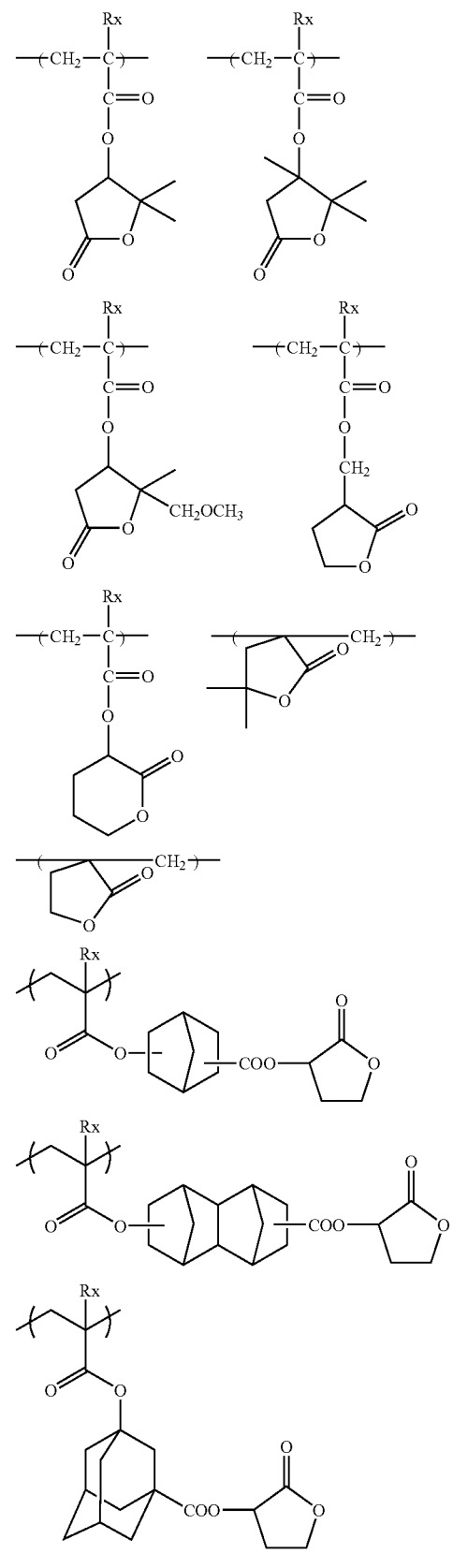
(In the formulae, Rx is H, CH$_3$, CH$_2$OH or CF$_3$.)

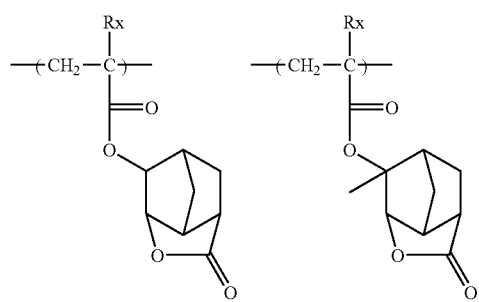
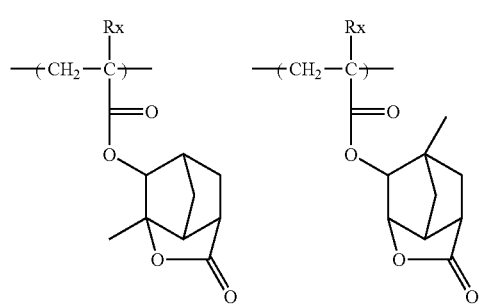
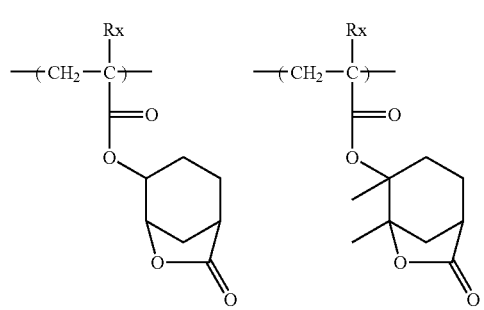
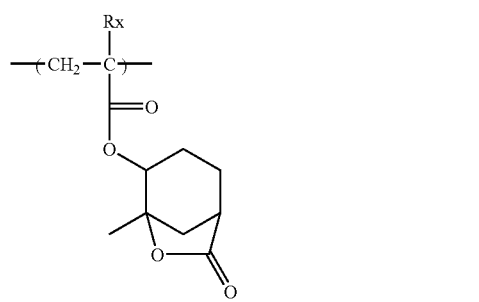
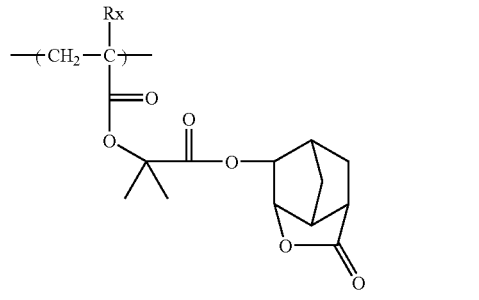
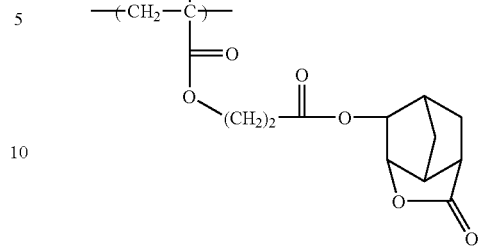
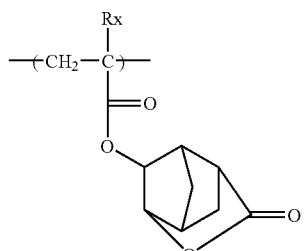
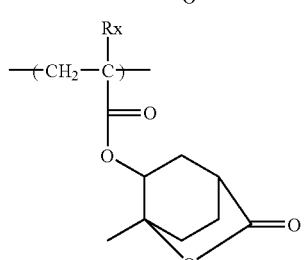
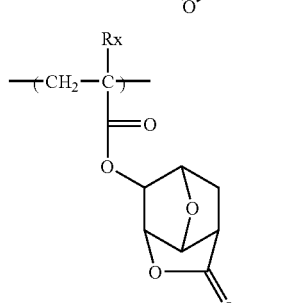
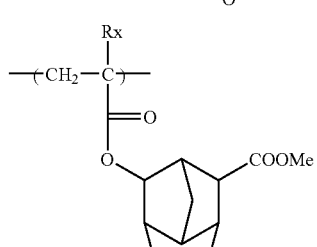
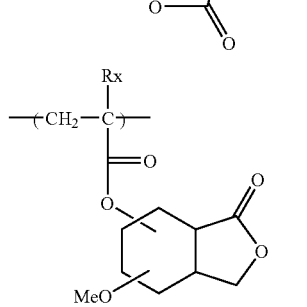

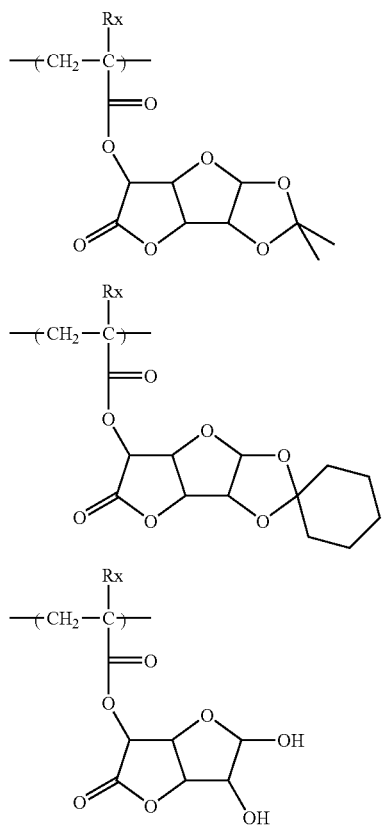

(In the formulae, Rx is H, CH₃, CH₂OH or CF₃.)

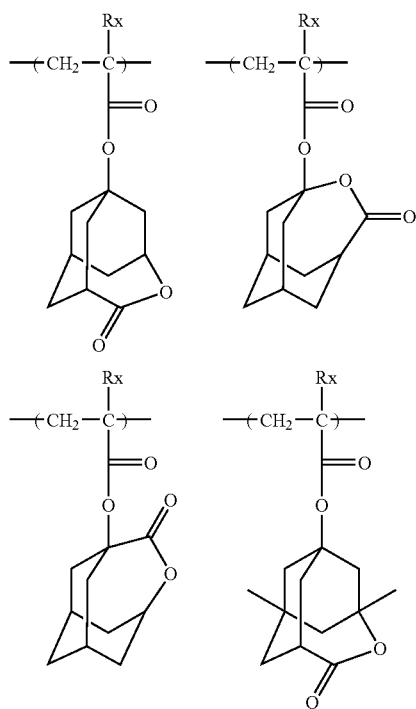

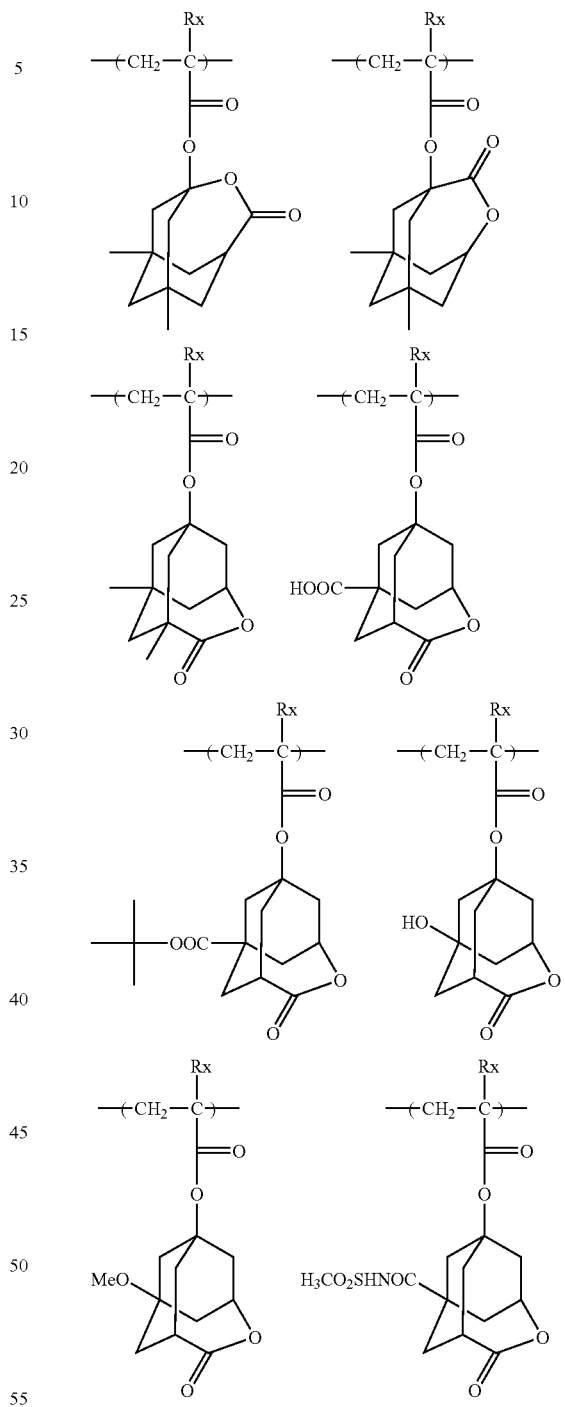

The alicyclic hydrocarbon-based acid-decomposable resin for use in the present invention preferably contains a repeating unit having an alicyclic hydrocarbon structure substituted by a polar group. By virtue of this repeating unit, the adhesion to substrate and the affinity for developer are enhanced. The polar group is preferably a hydroxyl group or a cyano group.

Examples of the alicyclic hydrocarbon structure substituted by a polar group include a structure represented by the following formula (VIIa) or (VIIb):

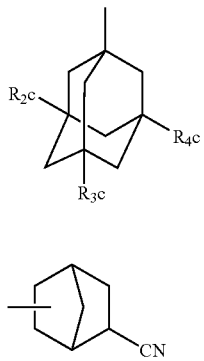

(VIIa)

(VIIb)

In formula (VIIa), $R_{2c}$ to $R_{4c}$ each independently represents a hydrogen atom, a hydroxyl group or a cyano group, provided that at least one of $R_{2c}$ to $R_{4c}$ represents a hydroxyl group or a cyano group. A structure where one or two member out of $R_{2c}$ to $R_{4c}$ is a hydroxyl group with the remaining being a hydrogen atom is preferred, and a structure where two members out of $R_{2c}$ to $R_{4c}$ are a hydroxyl group with the remaining being a hydrogen atom is more preferred.

The group represented by formula (VIIa) is preferably a dihydroxy form or a monohydroxy form, more preferably a dihydroxy form.

Examples of the repeating unit having a group represented by formula (VIIa) or (VIIb) include a repeating unit where at least one of $R_{13}'$ to $R_{16}'$ in formula (II-AB1) or (II-AB2) has a group represented by formula (VIIa) or (VIIb) (for example, $R_5$ of —COOR$_5$ is a group represented by formula (VIIa) or (VIIb)), and a repeating unit represented by the following formula (AIIa) or (AIIb):

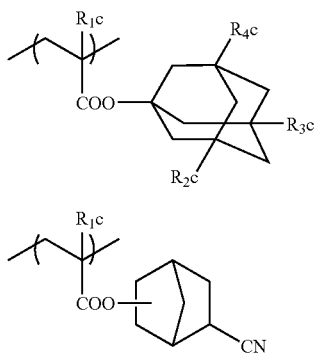

(AIIa)

(AIIb)

In formulae (AIIa) and (AIIb), $R_{1c}$ represents a hydrogen atom, a methyl group, a trifluoromethyl group or a hydroxymethyl group.

$R_{2c}$ to $R_{4c}$ have the same meanings as $R_{2c}$ to $R_{4c}$ in formula (VIIa).

Specific examples of the repeating unit having an alicyclic hydrocarbon structure substituted by a polar group, represented by formula (AIIa) or (AIIb), are set forth below, but the present invention is not limited thereto.

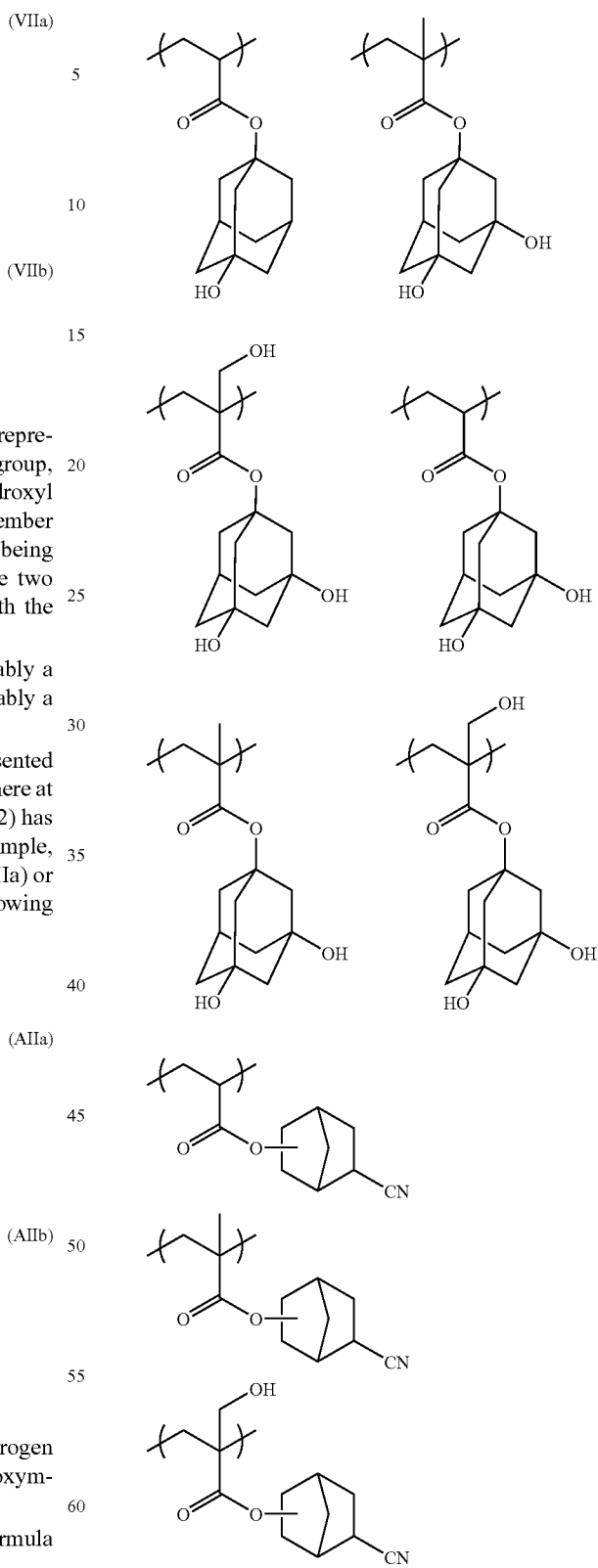

The alicyclic hydrocarbon-based acid-decomposable resin for use in the present invention may contain a repeating unit represented by the following formula (VIII):

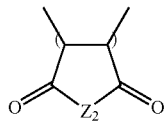

(VIII)

In formula (VIII), $Z_2$ represents —O— or —N($R_{41}$)—. $R_{41}$ represents a hydrogen atom, a hydroxyl group, an alkyl group or —OSO$_2$—R$_{42}$. $R_{42}$ represents an alkyl group, a cycloalkyl group or a camphor residue. The alkyl group of $R_{41}$ and $R_{42}$ may be substituted by a halogen atom (preferably fluorine atom) or the like.

Specific examples of the repeating unit represented by formula (VIII) are set forth below, but the present invention is not limited thereto.

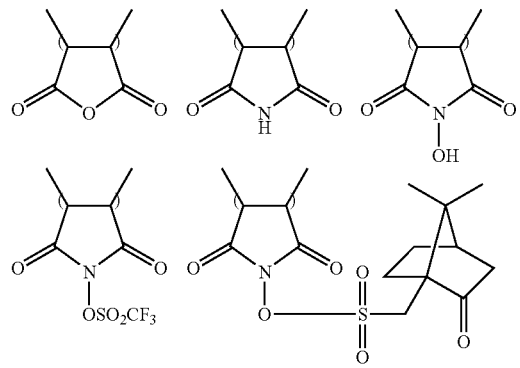

The alicyclic hydrocarbon-based acid-decomposable resin for use in the present invention preferably contains a repeating unit having an alkali-soluble group, more preferably a repeating unit having a carboxyl group. By virtue of containing such a repeating unit, the resolution increases in usage of forming contact holes. As for the repeating unit having a carboxyl group, a repeating unit where a carboxyl group is directly bonded to the resin main chain, such as repeating unit by an acrylic acid or a methacrylic acid, and a repeating unit where a carboxyl group is bonded to the resin main chain through a linking group, both are preferred. The linking group may have a monocyclic or polycyclic hydrocarbon structure. An acrylic acid and a methacrylic acid are most preferred.

The alicyclic hydrocarbon-based acid-decomposable resin for use in the present invention may contain a repeating unit having from 1 to 3 groups represented by the following formula (F1). By virtue of this repeating unit, the line edge roughness performance is enhanced.

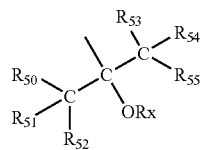

(F1)

In formula (F1), $R_{50}$ to $R_{55}$ each independently represents a hydrogen atom, a fluorine atom or an alkyl group, provided that at least one of $R_{50}$ to $R_{55}$ is a fluorine atom or an alkyl group with at least one hydrogen atom being substituted by a fluorine atom.

Rx represents a hydrogen atom or an organic group (preferably an acid-decomposable protective group, an alkyl group, a cycloalkyl group, an acyl group or an alkoxycarbonyl group).

The alkyl group of $R_{50}$ to $R_{55}$ may be substituted by a halogen atom (e.g., fluorine), a cyano group or the like and is preferably an alkyl group having a carbon number of 1 to 3, such as methyl group and trifluoromethyl group.

A group where $R_{50}$ to $R_{55}$ all are a fluorine atom is preferred.

The organic group represented by Rx is preferably an acid-decomposable group or an alkyl, cycloalkyl, acyl, alkylcarbonyl, alkoxycarbonyl, alkoxycarbonylmethyl, alkoxymethyl or 1-alkoxyethyl group which may have a substituent.

The repeating unit having a group represented by formula (F1) is preferably a repeating unit represented by the following formula (F2):

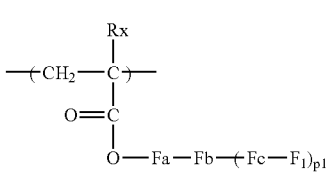

(F2)

In formula (F2), Rx represents a hydrogen atom, a halogen atom or an alkyl group having a carbon number of 1 to 4. Preferred examples of the substituent which the alkyl group of Rx may have include a hydroxyl group and a halogen atom.

Fa represents a single bond or a linear or branched alkylene group, preferably a single bond.

Fb represents a monocyclic or polycyclic hydrocarbon group.

Fc represents a single bond or a linear or branched alkylene group, preferably a single bond or a methylene group.

$F_1$ represents a group represented by formula (F1).

$p_1$ represents a number of 1 to 3.

The cyclic hydrocarbon group in Fb is preferably a cyclopentyl group, a cyclohexyl group or a norbornyl group.

Specific examples of the repeating unit having a structure of formula (F1) are set forth below.

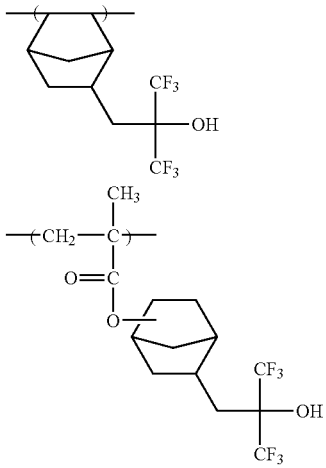

-continued

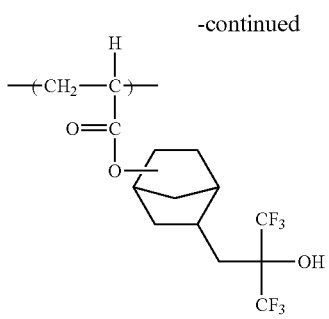

The alicyclic hydrocarbon-based acid-decomposable resin for use in the present invention may contain, in addition to the above-described repeating units, various repeating structural units for the purpose of controlling the dry etching resistance, suitability for standard developer, adhesion to substrate, resist profile and properties generally required of the resist, such as resolving power, heat resistance and sensitivity.

Examples of such a repeating structural unit include, but are not limited to, repeating structural units corresponding to the monomers described below.

By virtue of such a repeating structural unit, the performance required of the alicyclic hydrocarbon-based acid-decomposable resin, particularly, (1) solubility in the coating solvent,
(2) film-forming property (glass transition point),
(3) alkali developability,
(4) film loss (selection of hydrophilic, hydrophobic or alkali-soluble group),
(5) adhesion of unexposed area to substrate,
(6) dry etching resistance and the like, can be subtly controlled.

Examples of such a monomer include a compound having one addition-polymerizable unsaturated bond selected from acrylic acid esters, methacrylic acid esters, acrylamides, methacrylamides, allyl compounds, vinyl ethers and vinyl esters.

Other than these, an addition-polymerizable unsaturated compound copolymerizable with the monomer corresponding to the above-described various repeating structural units may be copolymerized.

In the alicyclic hydrocarbon-based acid-decomposable resin, the molar ratio of respective repeating structural units contained is appropriately set for controlling the dry etching resistance of resist, suitability for standard developer, adhesion to substrate, resist profile and performances generally required of the resist, such as resolving power, heat resistance and sensitivity.

The preferred embodiment of the alicyclic hydrocarbon-based acid-decomposable resin for use in the present invention includes the followings:

(1) a resin containing a repeating unit having an alicyclic hydrocarbon-containing partial structure represented by any one of formulae (pI) to (pV) (side chain type), preferably containing a repeating unit by a (meth)acrylate having a structure represented by any one of formulae (pI) to (pV), and (2) a resin containing a repeating unit represented by formula (II-AB) (main chain type).

The embodiment of (2) further includes:

(3) a resin having a repeating unit represented by formula (II-AB), a maleic anhydride derivative structure and a (meth)acrylate structure (hybrid type).

In the alicyclic hydrocarbon-based acid-decomposable resin, the content of the repeating unit having an acid-decomposable group is preferably from 10 to 60 mol %, more preferably from 20 to 50 mol %, still more preferably from 25 to 40 mol %, based on all repeating structural units.

In the alicyclic hydrocarbon-based acid-decomposable resin, the content of the repeating unit having an alicyclic hydrocarbon-containing partial structure represented by any one of formulae (pI) to (pV) is preferably from 25 to 70 mol %, more preferably from 35 to 65 mol %, still more preferably from 40 to 60 mol %, based on all repeating structural units.

In the alicyclic hydrocarbon-based acid-decomposable resin, the content of the repeating unit represented by formula (II-AB) is preferably from 10 to 60 mol %, more preferably from 15 to 55 mol %, still more preferably from 20 to 50 mol %, based on all repeating structural units.

In the resin, the content of the repeating structural unit based on the monomer as the further copolymerization component can also be appropriately selected according to the desired resist performance, but the content thereof is preferably 99 mol % or less, more preferably 90 mol % or less, still more preferably 80 mol % or less, based on the total molar number of the repeating structural unit having an alicyclic hydrocarbon-containing partial structure represented by any one of formulae (pI) to (pV) and the repeating unit represented by formula (II-AB).

When the composition of the present invention is used for exposure with ArF, the resin preferably has no aromatic group in view of transparency to ArF light.

The alicyclic hydrocarbon-based acid-decomposable resin for use in the present invention is preferably a resin where all repeating units comprise a (meth)acrylate repeating unit. In this case, the repeating units may be all a methacrylate, all an acrylate, or a mixture of methacrylate/acrylate, but the content of the acrylate repeating unit is preferably 50 mol % or less based on all repeating units.

The alicyclic hydrocarbon-based acid-decomposable resin for use in the present invention is more preferably a ternary copolymerization polymer comprising from 25 to 50% of the repeating unit having an alicyclic hydrocarbon-containing partial structure represented by any one of formulae (pI) to (pV), from 25 to 50% of the repeating unit having a lactone structure and from 5 to 30% of the repeating unit having an alicyclic hydrocarbon structure substituted by a polar group, or a quaternary copolymerization polymer additionally comprising from 5 to 20% of the repeating unit having a carboxyl group or a structure represented by formula (F1).

The alicyclic hydrocarbon-based acid-decomposable resin for use in the present invention can be synthesized by an ordinary method (for example, radical polymerization). Examples of the synthesis method in general include a batch polymerization method of dissolving the monomer species and an initiator in a solvent and heating the solution, thereby effecting the polymerization, and a dropping polymerization method of adding dropwise a solution containing monomer species and an initiator to a heated solvent over 1 to 10 hours. A dropping polymerization method is preferred. Examples of the reaction solvent include tetrahydrofuran, 1,4-dioxane, ethers (e.g., diisopropyl ether), ketones (e.g., methyl ethyl ketone, methyl isobutyl ketone), an ester solvent (e.g., ethyl acetate), an amide solvent (e.g., dimethylformamide, dimethylacetamide), and a solvent capable of dissolving the composition of the present invention, such as propylene glycol monomethyl ether acetate, propylene glycol monomethyl ether and cyclohexanone which are described later. The polymerization is preferably performed by using the same solvent as the solvent used in the photosensitive composition of the present invention. By the use of this solvent, generation of particles during storage can be suppressed.

The polymerization reaction is preferably performed in an inert gas atmosphere such as nitrogen and argon. As for the polymerization initiator, the polymerization is started by using a commercially available radical initiator (e.g., azo-based initiator, peroxide). The radical initiator is preferably an azo-based initiator, and an azo-based initiator having an ester group, a cyano group or a carboxyl group is preferred. Preferred examples of the initiator include azobisisobutyronitrile, azobisdimethylvaleronitrile and dimethyl 2,2'-azobis(2-methylpropionate). The initiator is added additionally or in parts, if desired. After the completion of reaction, the reactant is charged into a solvent, and the desired polymer is recovered by a method such as powder or solid recovery. The reaction concentration is from 5 to 50 mass %, preferably from 10 to 30 mass %, and the reaction temperature is usually from 10 to 150° C., preferably from 30 to 120° C., more preferably from 50 to 100° C.

In the case of using the composition of the present invention for the upper resist of a multilayer resist, the resin of the component (C) preferably has a silicon atom.

As for the resin having a silicon atom and capable of decomposing under the action of an acid to increase the solubility in an alkali developer, a resin having a silicon atom at least in either the main chain or the side chain can be used. Examples of the resin having a siloxane structure in the side chain of the resin include a copolymer of an olefin-based monomer having a silicon atom in the side chain and a (meth) acrylic acid-based monomer having a maleic anhydride and an acid-decomposable group in the side chain.

The resin having a silicon atom is preferably a resin having a trialkylsilyl structure or a monocyclic or polycyclic siloxane structure, more preferably a resin containing a repeating unit having a structure represented by any one of the following formulae (SS-1) to (SS-4), still more preferably a resin containing a (meth)acrylic acid ester-based, vinyl-based or acryl-based repeating unit having a structure represented by any one of formulae (SS-1) to (SS-4).

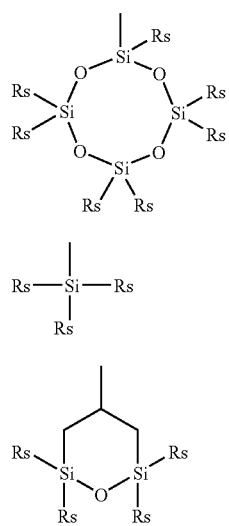

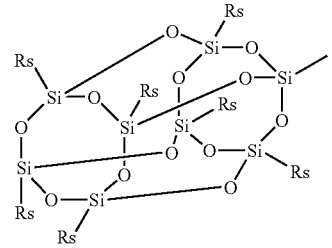

In formulae (SS-1) to (SS-4), Rs represents an alkyl group having a carbon number of 1 to 5, preferably a methyl group or an ethyl group.

The resin having a silicon atom is preferably a resin containing two or more different silicon atom-containing repeating units, more preferably a resin containing both (Sa) a repeating unit having from 1 to 4 silicon atoms and (Sb) a repeating unit having from 5 to 10 silicon atoms, still more preferably a resin containing at least one repeating unit having a structure represented by any one of formulae (SS-1) to (SS-3) and a repeating unit having a structure represented by formula (SS-4).

In the case of irradiating the positive photosensitive composition of the present invention with $F_2$ excimer laser light, the resin of the component (C) is preferably a resin having a structure that a fluorine atom is substituted to the main chain and/or the side chain of the polymer skeleton, and being capable of decomposing under the action of an acid to increase the solubility in an alkali developer (hereinafter sometimes referred to as a "fluorine-based acid-decomposable resin"), more preferably a resin-containing a hydroxyl group with the 1-position being substituted by a fluorine atom or a fluoroalkyl group or containing a group where the hydroxyl group with the 1-position being substituted by a fluorine atom or a fluoroalkyl group is protected by an acid-decomposable group, and still more preferably a resin having a hexafluoro-2-propanol structure or a structure that the hydroxyl group of hexafluoro-2-propanol is protected by an acid-decomposable group. By virtue of introducing a fluorine atom, the transparency to far ultraviolet light, particularly $F_2$ (157 nm) light, can be enhanced.

Preferred examples of the fluorine-based acid-decomposable resin include a resin having at least one repeating unit represented by the following formulae (FA) to (FG):

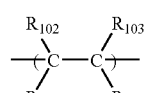

(FA)

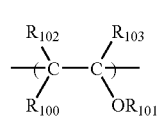

(FB)

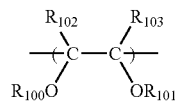

(FC)

-continued

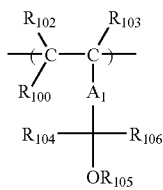
(FD)

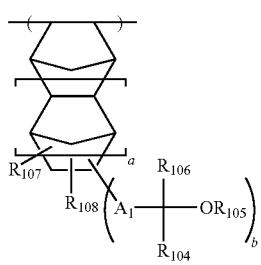
(FE)

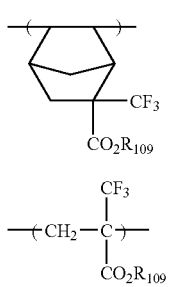
(FF)

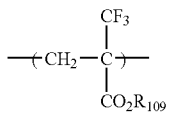
(FG)

In these formulae, $R_{100}$ to $R_{103}$ each represents a hydrogen atom, a fluorine atom, an alkyl group or an aryl group.

$R_{104}$ and $R_{106}$ each is a hydrogen atom, a fluorine atom or an alkyl group, and at least either one of $R_{104}$ and $R_{106}$ is a fluorine atom or a fluoroalkyl group. $R_{104}$ and $R_{106}$ are preferably both a trifluoromethyl group.

$R_{105}$ is a hydrogen atom, an alkyl group, a cycloalkyl group, an acyl group, an alkoxycarbonyl group or a group capable of decomposing under the action of an acid.

$A_1$ is a single bond, a divalent linking group such as alkylene group, cycloalkylene group, alkenylene group, arylene group, —OCO—, —COO— and —CON($R_{24}$)—, or a linking group comprising a plurality of members out of these groups. $R_{24}$ is a hydrogen atom or an alkyl group.

$R_{107}$ and $R_{108}$ each is a hydrogen atom, a halogen atom, an alkyl group, an alkoxy group, an alkoxycarbonyl group or a group capable of decomposing under the action of an acid.

$R_{109}$ is a hydrogen atom, an alkyl group, a cycloalkyl group or a group capable of decomposing under the action of an acid.

b is 0, 1 or 2.

In formulae (FA) and (FC), $R_{100}$ and $R_{101}$ may form a ring through an alkylene group (having a carbon number of 1 to 5) which may be substituted by fluorine.

The repeating units represented by formulae (FA) to (FG) each contains at least one fluorine atom, preferably 3 or more fluorine atoms, per one repeating unit.

In formulae (FA) to (FG), the alkyl group is, for example, an alkyl group having a carbon number of 1 to 8, and specific preferred examples thereof include a methyl group, an ethyl group, a propyl group, an n-butyl group, a sec-butyl group, a hexyl group, a 2-ethylhexyl group and an octyl group.

The cycloalkyl group may be monocyclic or polycyclic. The monocyclic type is a cycloalkyl group having a carbon number of 3 to 8, and preferred examples thereof include a cyclopropyl group, a cyclopentyl group, a cyclohexyl group, a cycloheptyl group and a cyclooctyl group. The polycyclic type is a cycloalkyl group having a carbon number of 6 to 20, and preferred examples thereof include an adamantyl group, a norbornyl group, an isoboronyl group, a camphanyl group, a dicyclopentyl group, an α-pinel group, a tricyclodecanyl group, a tetracyclododecyl group and an androstanyl group. In these monocyclic or polycyclic cycloalkyl groups, the carbon atom may be substituted by a heteroatom such as oxygen atom.

The fluoroalkyl group is, for example, a fluoroalkyl group having a carbon number of 1 to 12, and specific preferred examples thereof include a trifluoromethyl group, a perfluoroethyl group, a perfluoropropyl group, a perfluorobutyl group, a perfluorohexyl group, a perfluorooctyl group, a perfluorooctylethyl group and a perfluorododecyl group.

The aryl group is, for example, an aryl group having a carbon number of 6 to 15, and specific preferred examples thereof include a phenyl group, a tolyl group, a dimethylphenyl group, a 2,4,6-trimethylphenyl group, a naphthyl group, an anthryl group and a 9,10-dimethoxyanthryl group.

The alkoxy group is, for example, an alkoxy group having a carbon number of 1 to 8, and specific preferred examples thereof include a methoxy group, an ethoxy group, an n-propoxy group, an iso-propoxy group, a butoxy group, a pentoxy group, an allyloxy group and an octoxy group.

The acyl group is, for example, an acyl group having a carbon number of 1 to 10, and specific preferred examples thereof include a formyl group, an acetyl group, a propanoyl group, a butanoyl group, a pivaloyl group, an octanoyl group and a benzoyl group.

The alkoxycarbonyl group is preferably a secondary alkoxycarbonyl group, more preferably a tertiary alkoxycarbonyl group, such as i-propoxycarbonyl group, tert-butoxycarbonyl group, tert-amyloxycarbonyl group and 1-methyl-1-cyclohexyloxycarbonyl group.

Examples of the halogen atom include a fluorine atom, a chlorine atom, a bromine atom and an iodine atom.

The alkylene group is preferably an alkylene group having a carbon number of 1 to 8, such as methylene group, ethylene group, propylene group, butylene group, hexylene group and octylene group.

The alkenylene group is preferably an alkenylene group having a carbon number of 2 to 6, such as ethenylene group, propenylene group and butenylene group.

The cycloalkylene group is preferably a cycloalkylene group having a carbon number of 5 to 8, such as cyclopentylene group and cyclohexylene group.

The arylene group is preferably an arylene group having a carbon number of 6 to 15, such as phenylene group, tolylene group and naphthylene group.

These groups each may have a substituent, and examples of the substituent include those having an active hydrogen, such as alkyl group, cycloalkyl group, aryl group, amino group, amido group, ureido group, urethane group, hydroxyl group and carboxyl group, a halogen atom (e.g., fluorine, chlorine, bromine, iodine), an alkoxy group (e.g., methoxy, ethoxy, propoxy, butoxy), a thioether group, an acyl group (e.g., acetyl, propanoyl, benzoyl), an acyloxy group (e.g., acetoxy, propanoyloxy, benzoyloxy), an alkoxycarbonyl group (e.g., methoxycarbonyl, ethoxycarbonyl, propoxycarbonyl), a cyano group and a nitro group.

Here, the alkyl group, cycloalkyl group and aryl group include those described above, and the alkyl group may be further substituted by a fluorine atom or a cycloalkyl group.

Examples of the group capable of decomposing under the action of an acid to show alkali solubility, which is contained in the fluorine-based acid-decomposable resin of the present invention, include —O—C($R_{36}$)($R_{37}$)($R_{38}$), —O—C($R_{36}$)($R_{37}$)(O$R_{39}$), —O—COO—C($R_{36}$)($R_{37}$)($R_{38}$), —O—C($R_{01}$)($R_{02}$)COO—C($R_{36}$)($R_{37}$)($R_{38}$), —COO—C($R_{36}$)($R_{37}$)($R_{38}$) and —COO—C($R_{36}$)($R_{37}$)(O$R_{39}$).

$R_{36}$ to $R_{39}$ each represents an alkyl group, a cycloalkyl group, an aryl group, an aralkyl group or an alkenyl group, and $R_{01}$ and $R_{02}$ each represents a hydrogen atom, an alkyl group, a cycloalkyl group, an alkenyl group (e.g., vinyl, allyl, butenyl, cyclohexenyl), an aralkyl group (e.g., benzyl, phenethyl, naphthylmethyl) or an aryl group.

Specific preferred examples include an ether or ester group of a tertiary alkyl group, such as tert-butyl group, tert-amyl group, 1-alkyl-1-cyclohexyl group, 2-alkyl-2-adamantyl group, 2-adamantyl-2-propyl group and 2-(4-methylcyclohexyl)-2-propyl group; an acetal or acetal ester group such as 1-alkoxy-1-ethoxy group and tetrahydropyranyl group; a tert-alkylcarbonate group; and a tert-alkylcarbonylmethoxy group.

Specific examples of the repeating structural units represented by formulae (FA) to (FG) are set forth below, but the present invention is not limited thereto.

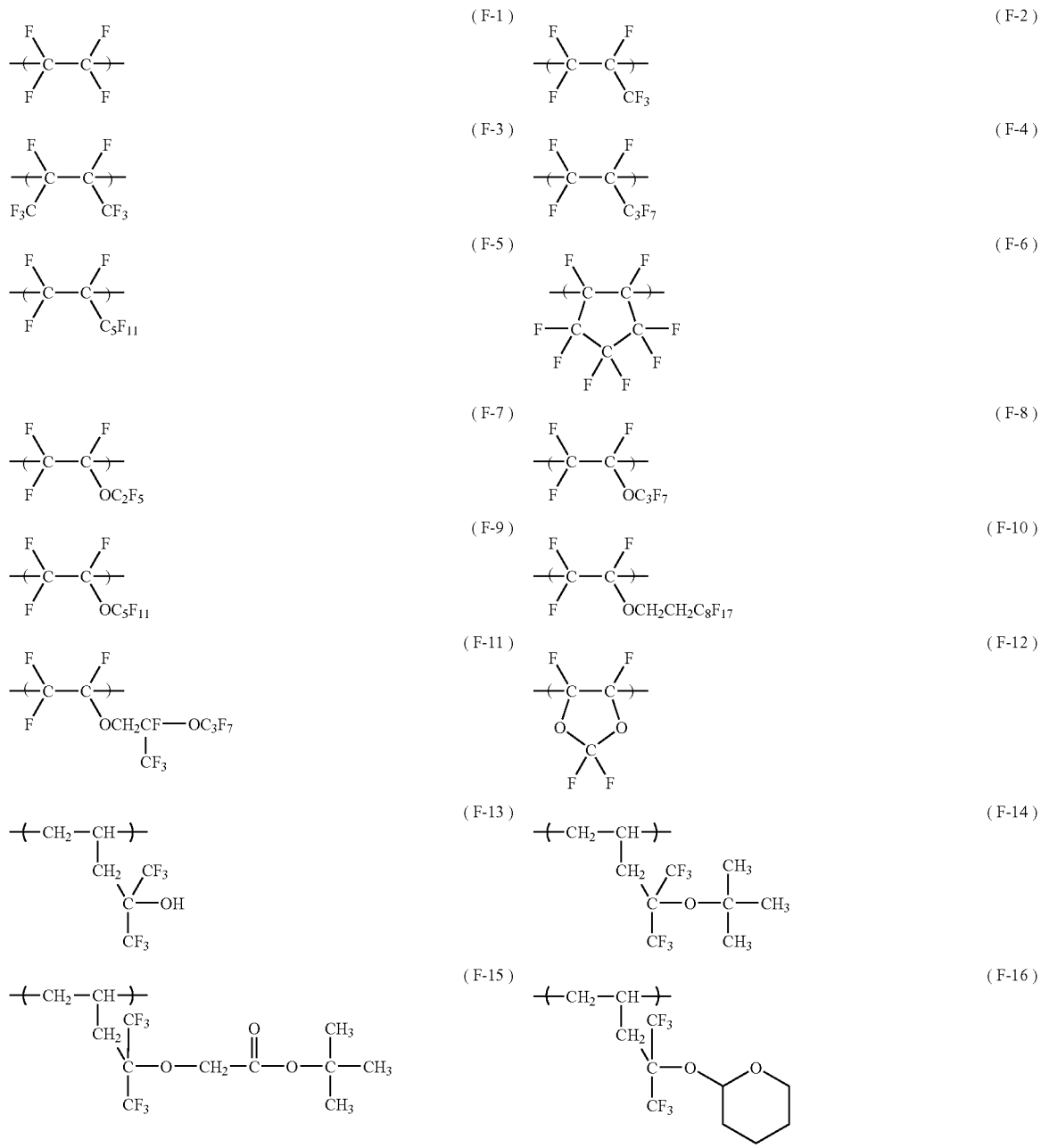

(F-17) 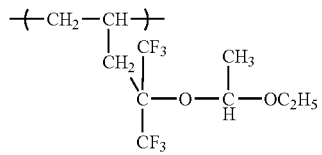
(F-18) 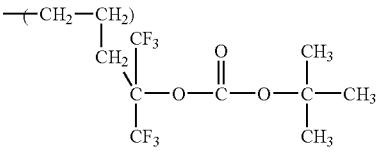
(F-19) 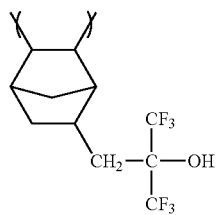
(F-20) 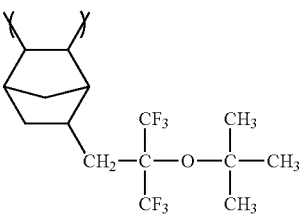
(F-21) 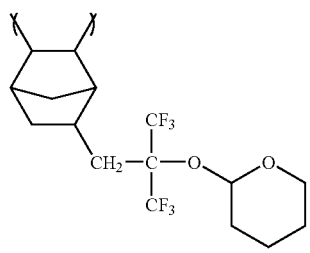
(F-22) 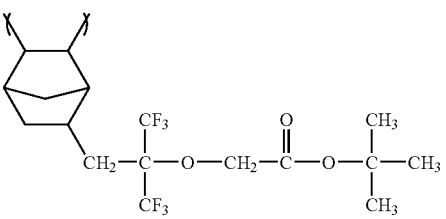
(F-23) 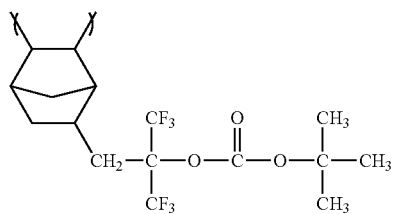
(F-24) 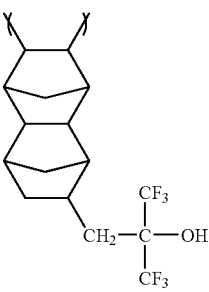
(F-25) 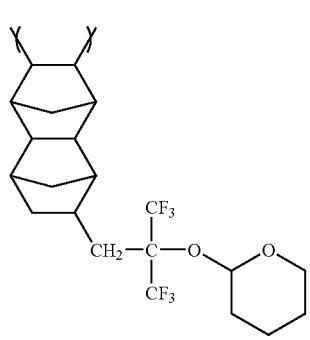
(F-26) 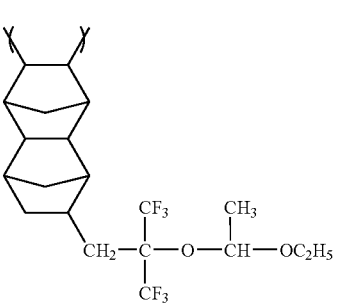
(F-27) 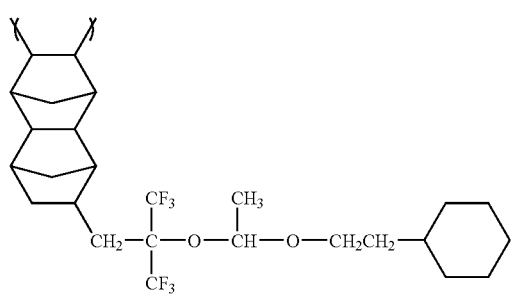
(F-28) 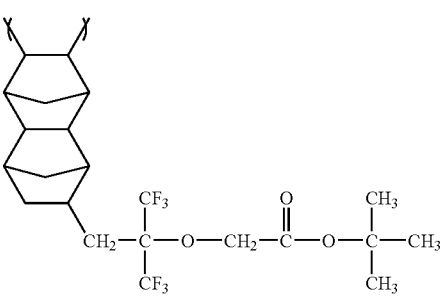

-continued
(F-29)
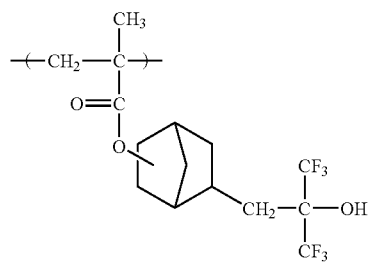
(F-30)
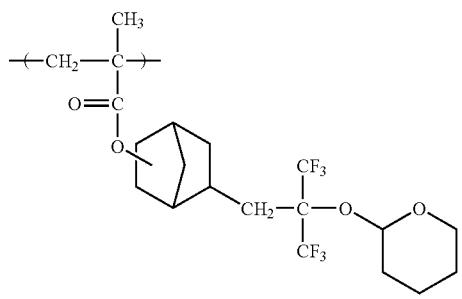
(F-31)
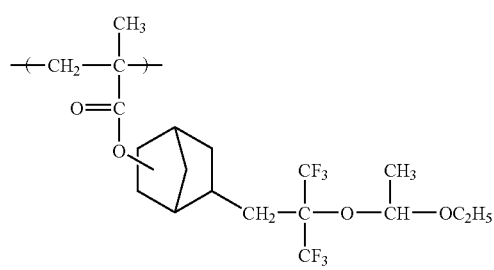
(F-32)
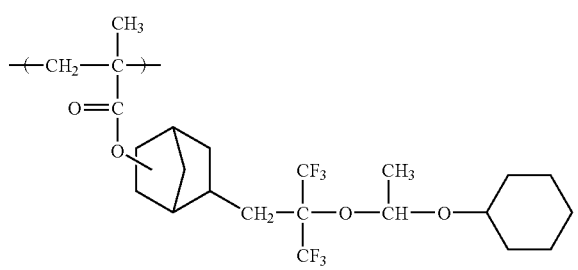
(F-33)
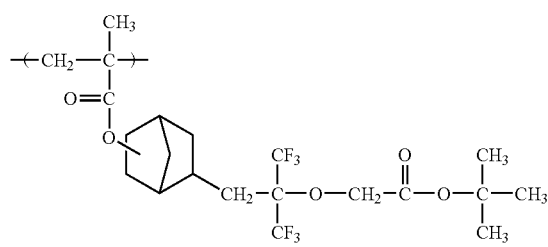
(F-34)
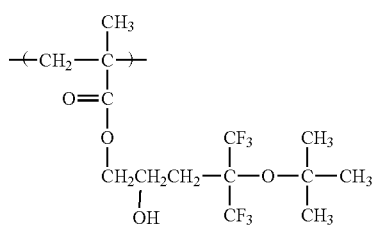
(F-35)
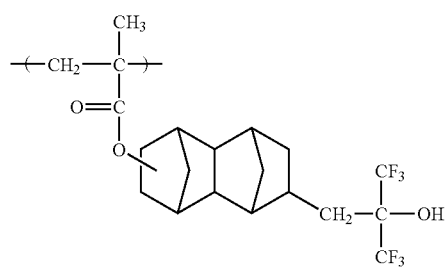
(F-36)
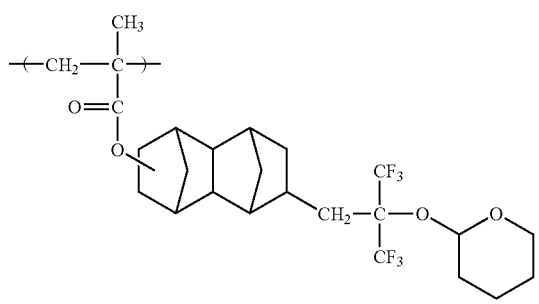
(F-37)
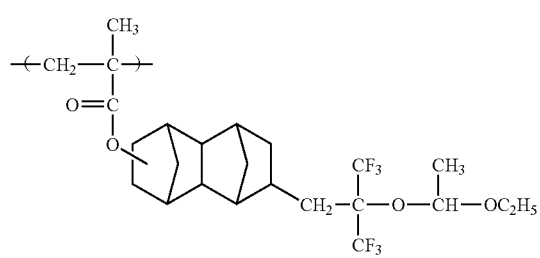
(F-38)
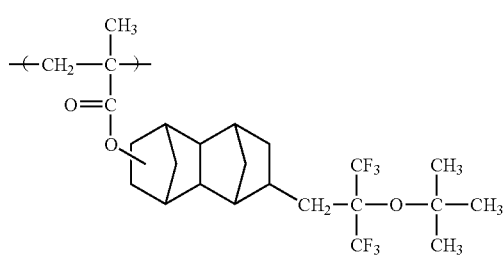

-continued
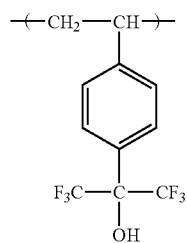 (F-39)
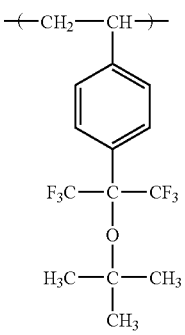 (F-40)
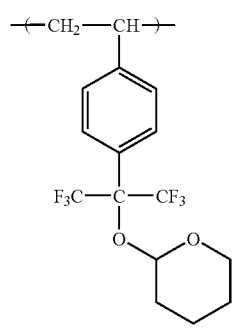 (F-41)
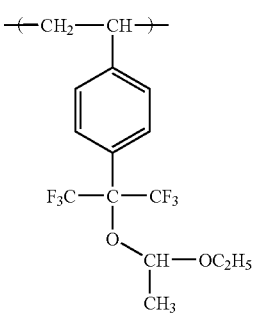 (F-42)
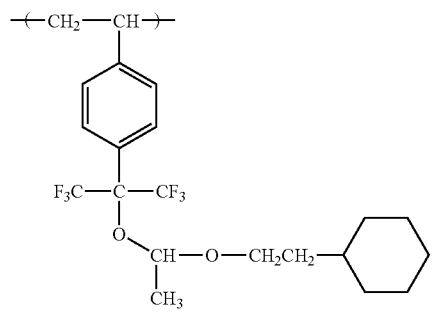 (F-43)
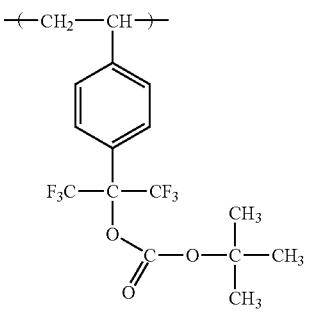 (F-44)
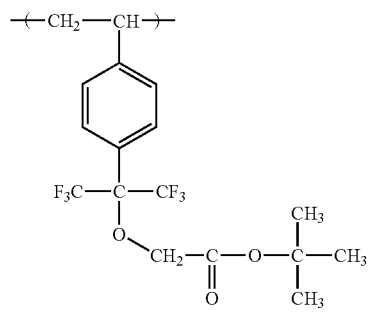 (F-45)
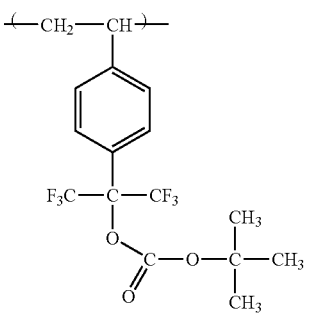 (F-46)
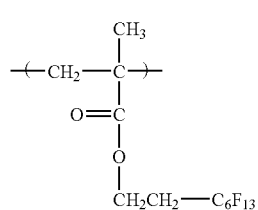 (F-47)
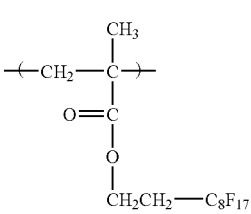 (F-48)

-continued
(F-49)
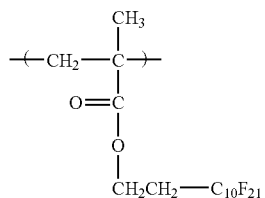
(F-50)
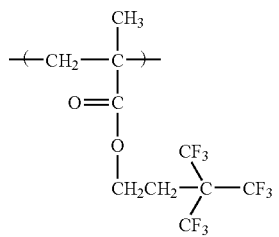
(F-51)
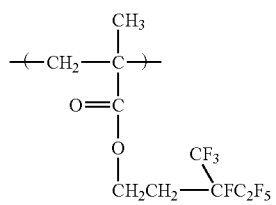
(F-52)
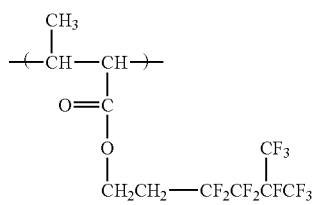
(F53)
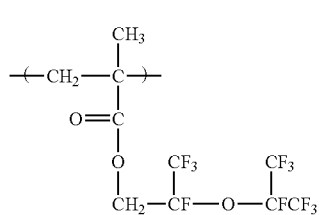
(F-54)
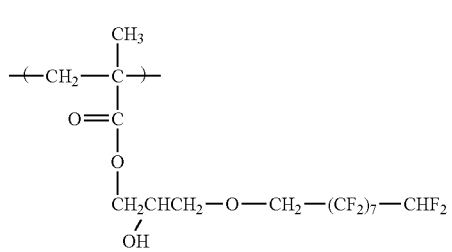
(F-55)
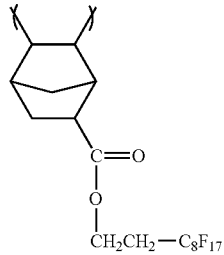
(F-56)
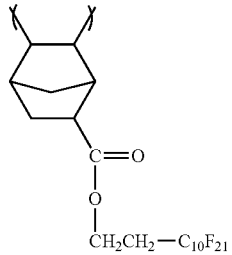
(F-57)
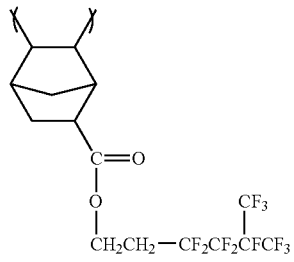
(F-58)
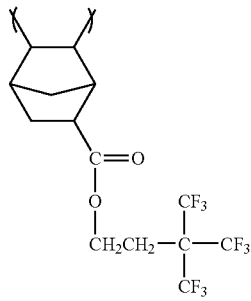
(F-59)
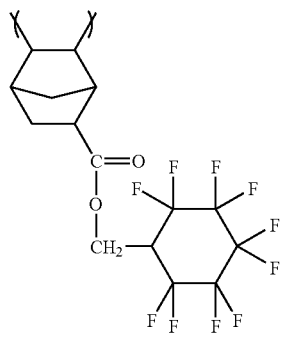
(F-60)
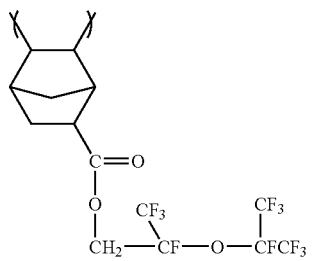

-continued

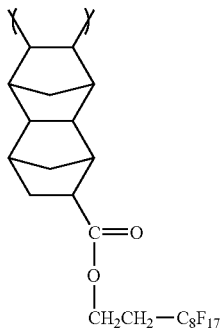
(F-61)

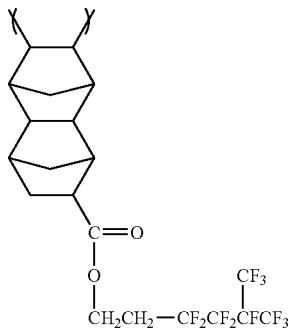
(F-62)

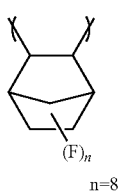
n=8
(F-63)

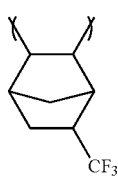
(F-64)

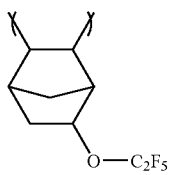
(F-65)

The total content of the repeating units represented by formulae (FA) to (FG) is generally from 10 to 80 mol %, preferably from 30 to 70 mol %, more preferably from 35 to 65 mol %, based on all repeating units constituting the resin.

In the fluorine-based acid-decomposable resin, in addition to these repeating structural units, other polymerizable monomers may be copolymerized for the purpose of enhancing the performance of the resist of the present invention.

Examples of the copolymerization monomer which can be used include a compound having one addition-polymerizable unsaturated bond selected from acrylic acid esters other than those described above, acrylamides, methacrylic acid esters, methacrylamides, allyl compounds, vinyl ethers, vinyl esters, styrenes and crotonic acid esters.

From the standpoint of enhancing the dry etching resistance, controlling the alkali solubility and increasing the adhesion to substrate, the fluorine-based acid-decomposable resin preferably contains another repeating unit as a copolymerization component in addition to the above-described fluorine atom-containing repeating unit. Preferred examples of the another repeating unit include:

1) a repeating unit having an alicyclic hydrocarbon structure represented by any one of formulae (pI) to (pVI) and formula (II-AB), specifically, repeating units 1 to 23 and repeating units [II-1] to [II-32], preferably repeating units 1 to 23 where Rx is $CF_3$;

2) a repeating unit having a lactone structure represented by formula (Lc) or by any one of formulae (V-1) to (V-5), specifically, repeating units shown above, particularly, repeating units having a group represented by any one of formulae (Lc) and (V-1) to (V-4); and 3) a repeating unit derived from a maleic anhydride, a vinyl ether or a vinyl compound having a cyano group, represented by the following formula (XV), (XVI) or (XVII), specifically, repeating units (C-1) to (C-15). These repeating units each may or may not contain a fluorine atom.

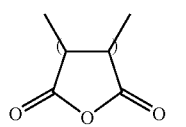
(XV)

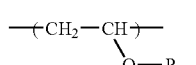
(XVI)

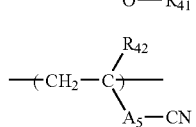
(XVII)

In these formulae, $R_{41}$ represents an alkyl group, a cycloalkyl group; an aralkyl group or an aryl group, and the alkyl group of $R_{41}$ may be substituted by an aryl group.

$R_{42}$ represents a hydrogen atom, a halogen atom, a cyano group or an alkyl group.

$A_5$ represents a single bond, a divalent alkylene, alkenylene, cycloalkylene or arylene group, —O—CO—$R_{22}$, —CO—O—$R_{23}$— or —CO—N($R_{24}$)—$R_{25}$—.

$R_{22}$, $R_{23}$ and $R_{25}$, which may be the same or different, each represents a single bond or a divalent alkylene, alkenylene, cycloalkylene or arylene group which may have an ether group, an ester group, an amide group, a urethane group or a ureido group.

$R_{24}$ represents a hydrogen atom, an alkyl group, a cycloalkyl group, an aralkyl group or an aryl group.

Examples of each substituent are the same as those described above for the substituents of formulae (FA) to (FG).

Specific examples of the repeating structural units represented by formulae (XV) to (XVII) are set forth below, but the present invention is not limited thereto.

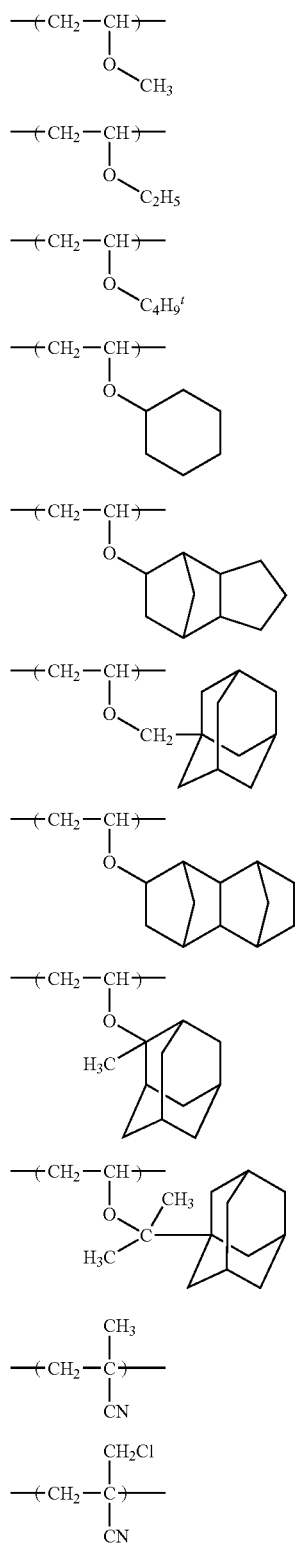

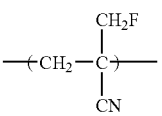

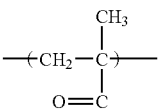

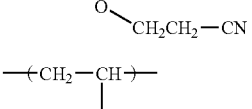

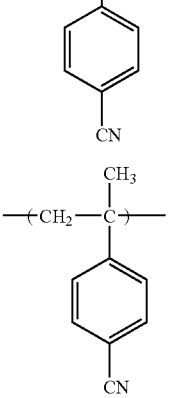

The total amount of the repeating unit represented by any one of formulae (XV) to (XVII) and the another repeating unit is generally from 0 to 70 mol %, preferably from 10 to 60 mol %, more preferably from 20 to 50 mol %, based on all repeating units constituting the resin.

The fluorine-based acid-decomposable resin may contain an acid-decomposable group in any repeating unit.

The content of the repeating unit having an acid-decomposable group is preferably from 10 to 70 mol %, more preferably from 20 to 60 mol %, still more preferably from 30 to 60 mol %, based on all repeating units.

The fluorine-based acid-decomposable resin can be synthesized by radical polymerization almost in the same manner as the alicyclic hydrocarbon-based acid-decomposable resin.

The weight average molecular weight of the resin as the component (C) is preferably from 2,000 to 200,000 in terms of polystyrene by the GPC method. When the weight average molecular weight is 2,000 or more, heat resistance and dry etching resistance can be elevated and when the weight average molecular weight is 200,000 or less, developability can be enhanced and at the same time, by virtue of reduction in the viscosity, the film-forming property can be enhanced. The molecular weight is more preferably from 5,000 to 50,000, still more preferably from 7,000 to 30,000. By adjusting the molecular weight, the composition can be satisfied with all of heat resistance, resolving power, development defect and the like. The dispersity (Mw/Mn) of the resin as the component (C) is preferably from 1.0 to 3.0, more preferably from 1.2 to 2.5, still more preferably from 1.2 to 1.6. By adjusting the dispersity to an appropriate range, the line edge roughness performance can be enhanced.

In the positive photosensitive composition of the present invention, the blending amount of the resin as the component (C) in the entire composition is preferably from 40 to 99.99 mass %, more preferably from 50 to 99 mass %, still more preferably from 80 to 96 mass %, based on the entire solid content.

[4] (D) Dissolution Inhibiting Compound Capable of Decomposing Under the Action of an Acid to Increase the Solubility in an Alkali Developer and Having a Molecular Weight of 3,000 Or Less (Hereinafter Sometimes Referred to as a "Component (D)" or "Dissolution Inhibiting Compound")

In order to prevent reduction in the transparency to light at 220 nm or less, the dissolution inhibiting compound (D) capable of decomposing under the action of an acid to increase the solubility in an alkali developer and having a molecular weight of 3,000 or less is preferably an alicyclic or aliphatic compound containing an acid-decomposable group, such as acid-decomposable group-containing cholic acid derivative described in Proceeding of SPIE, 2724, 355 (1996). Examples of the acid-decomposable group and alicyclic structure are the same as those described above for the alicyclic hydrocarbon-based acid-decomposable resin.

In the case where the photosensitive composition of the present invention is exposed with a KrF excimer laser or irradiated with electron beams, the dissolution inhibiting compound preferably contains a structure in which the phenolic hydroxyl group of a phenol compound is replaced by an acid-decomposable group. The phenol compound is preferably a phenol compound containing from 1 to 9 phenol skeletons, more preferably from 2 to 6 phenol skeletons.

The molecular weight of the dissolution inhibiting compound for use in the present invention is 3,000 or less, preferably from 300 to 3,000, more preferably from 500 to 2,500.

The amount of the dissolution inhibiting compound added is preferably from 3 to 50 mass %, more preferably from 5 to 40 mass %, based on the solid content of the photosensitive composition.

Specific examples of the dissolution inhibiting compound are set forth below, but the present invention is not limited thereto.

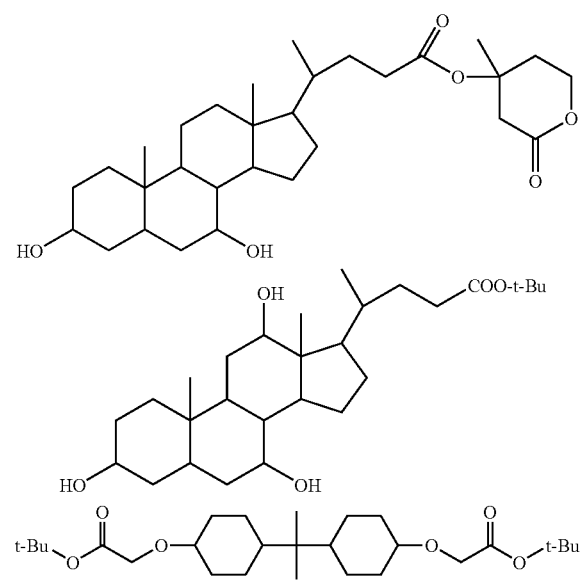

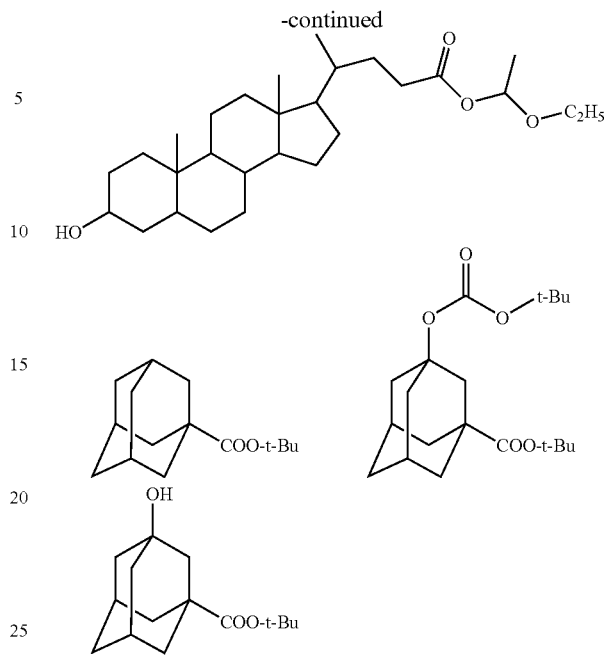

[5] (E) Resin Soluble in an Alkali Developer (Hereinafter Sometimes Referred to as a "Component (E)" or "Alkali-Soluble Resin")

The alkali dissolution rate of the alkali-soluble resin is preferably 20 Å/sec or more, more preferably 200 Å/sec or more (Å is angstrom), as measured (at 23° C.) in 0.261N tetramethylammonium hydroxide (TMAH).

Examples of the alkali-soluble resin for use in the present invention include, but are not limited to, a novolak resin, a hydrogenated novolak resin, an acetone-pyrogallol resin, an o-polyhydroxystyrene, an m-polyhydroxystyrene, a p-polyhydroxystyrene, a hydrogenated polyhydroxystyrene, a halogen- or alkyl-substituted polyhydroxystyrene, a hydroxystyrene-N-substituted maleimide copolymer, an o/p- or m/p-hydroxystyrene copolymer, a polyhydroxystyrene with the hydroxyl group being partially O-alkylated (for example, 5 to 30 mol % being O-methylated, O-(1-methoxy)ethylated, O-(1-ethoxy)ethylated, O-2-tetra-hydropyranylated or O-(tert-butoxycarbonyl)methylated) or O-acylated (for example, 5 to 30 mol % being o-acylated or O-(tert-butoxy) carbonylated), a styrene-maleic anhydride copolymer, a styrene-hydroxystyrene copolymer, an α-methylstyrene-hydroxystyrene copolymer, a carboxyl group-containing methacrylic resin including a derivative thereof, and a polyvinyl alcohol derivative.

Among these alkali-soluble resins, preferred are a novolak resin, an o-polyhydroxystyrene, an m-polyhydroxystyrene, a p-polyhydroxystyrene, a copolymer thereof, an alkyl-substituted polyhydroxystyrene, a partially O-alkylated or O-acylated polyhydroxystyrene, a styrene-hydroxystyrene copolymer, and an α-methylstyrene-hydroxy-styrene copolymer.

The novolak resin can be obtained by subjecting a predetermined monomer as the main component to addition condensation with aldehydes in the presence of an acidic catalyst.

The weight average molecular weight of the alkali-soluble resin is 2,000 or more, preferably from 5,000 to 200,000, more preferably from 5,000 to 100,000.

Here, the weight average molecular weight is defined as a polystyrene-reduced value measured by gel permeation chromatography.

In the present invention, two or more kinds of these alkali-soluble resins (E) may be used in combination.

The amount of the alkali-soluble resin used is from 40 to 97 mass %, preferably from 60 to 90 mass %, based on the entire solid content of the photosensitive composition.

[6] (F) Acid Crosslinking Agent Capable of Crosslinking with the Alkali-Soluble Resin Under the Action of an Acid (Hereinafter Sometimes Referred to as a "Component (F)" or "Crosslinking Agent")

In the negative photosensitive composition of the present invention, a crosslinking agent is used.

The crosslinking agent may be any compound as long as it causes crosslinking of the resin soluble in an alkali developer under the action of an acid, but the following compounds (1) to (3) are preferred:

(1) a hydroxymethyl, alkoxymethyl or acyloxymethyl form of a phenol derivative, (2) a compound having an N-hydroxymethyl group, an N-alkoxymethyl group or an N-acyloxymethyl group, and (3) a compound having an epoxy group.

The alkoxymethyl group is preferably an alkoxymethyl group having a carbon number of 6 or less, and the acyloxymethyl group is preferably an acyloxymethyl group having a carbon number of 6 or less.

Among these crosslinking agents, the followings are particularly preferred.

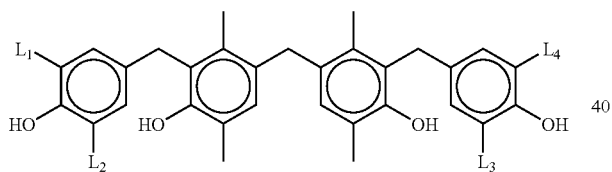

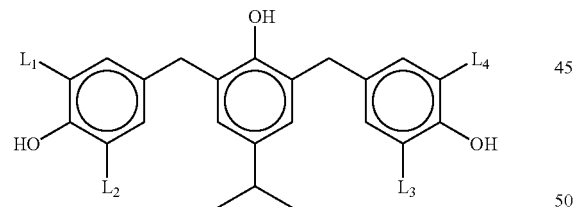

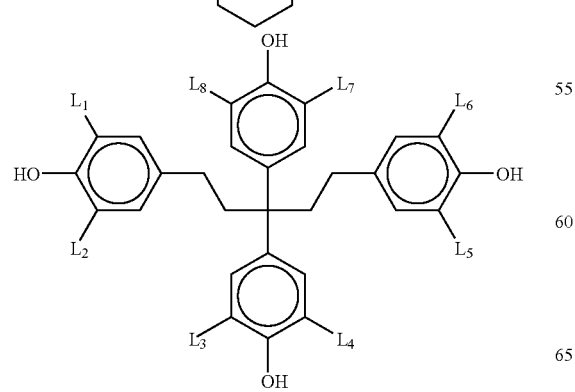

-continued

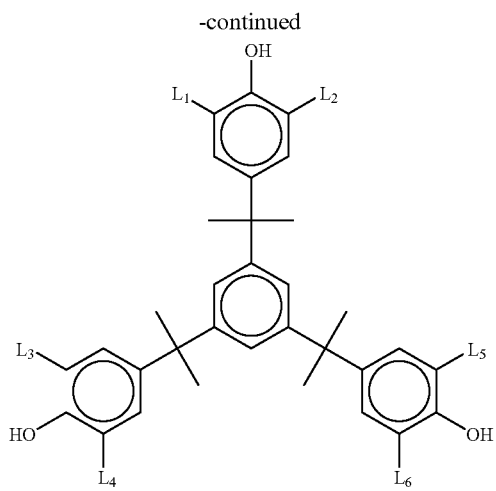

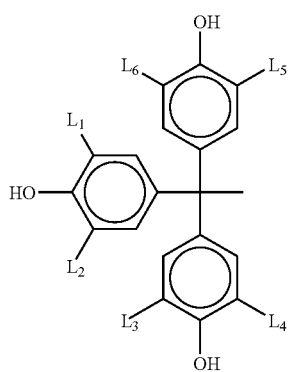

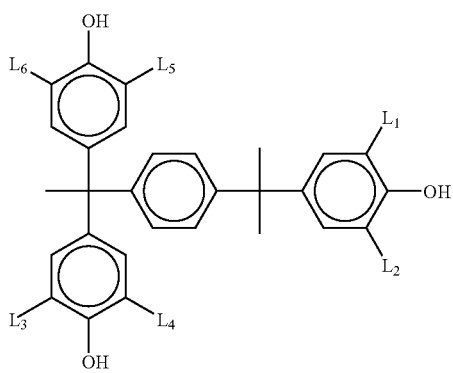

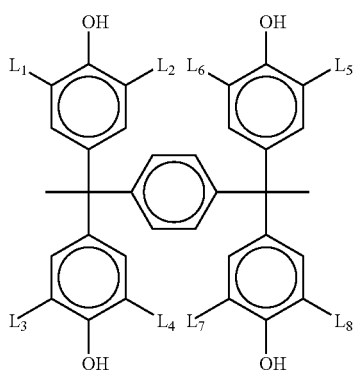

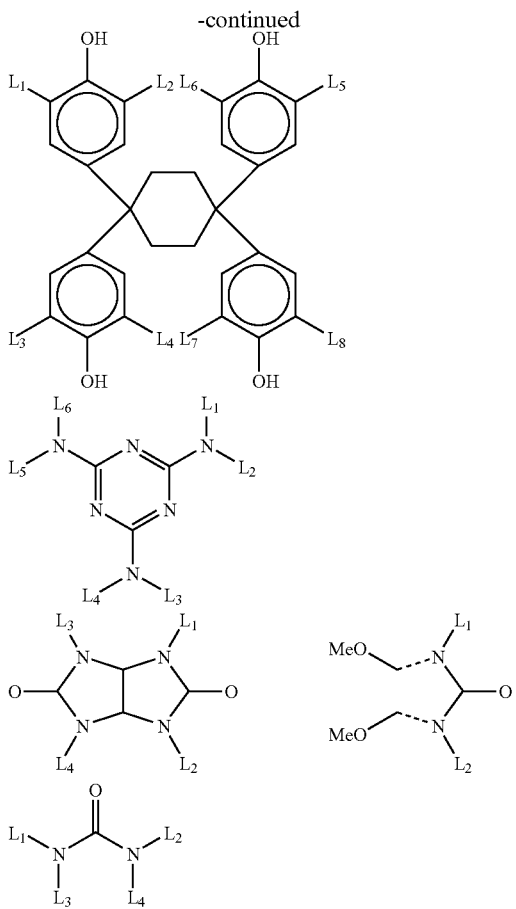

In these formulae, $L^1$ to $L^8$, which may be the same or different, each represents a hydrogen atom, a hydroxymethyl group, a methoxymethyl group, an ethoxymethyl group or an alkyl group having a carbon number of 1 to 6.

The crosslinking agent is usually added in an amount of 3 to 70 mass %, preferably from 5 to 50 mass %, based on the solid content of the photosensitive composition.

<Other Components>

[7] (G) Basic Compound

The photosensitive composition of the present invention preferably contains (G) a basic compound so as to reduce the change of performance in aging from exposure to heating.

Preferred structures of the basic compound include the structures represented by the following formulae (A) to (E).

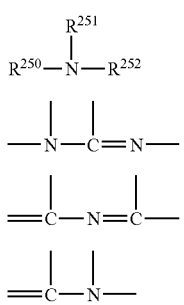

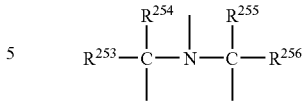

In these formulae, $R^{250}$, $R^{251}$ and $R^{252}$ each independently represents a hydrogen atom, an alkyl group having a carbon number of 1 to 20, a cycloalkyl group having a carbon number of 3 to 20, or an aryl group having a carbon number of 6 to 20, and $R^{250}$ and $R^{251}$ may combine with each other to form a ring. These groups each may have a substituent. The alkyl or cycloalkyl group having a substituent is preferably an aminoalkyl group having a carbon number of 1 to 20, an aminocycloalkyl group having a carbon number of 3 to 20, a hydroxyalkyl group having a carbon number of 1 to 20, or a hydroxycycloalkyl group having a carbon number of 3 to 20.

These groups each may contain an oxygen atom, a sulfur atom or a nitrogen atom in the alkyl chain.

$R^{253}$, $R^{254}$, $R^{255}$ and $R^{256}$ each independently represents an alkyl group having a carbon number of 1 to 6 or a cycloalkyl group having a carbon number of 3 to 6.

Preferred examples of the compound include guanidine, aminopyrrolidine, pyrazole, pyrazoline, piperazine, aminomorpholine, aminoalkylmorpholine and piperidine, and these compounds each may have a substituent. More preferred examples of the compound include a compound having an imidazole structure, a diazabicyclo structure, an onium hydroxide structure, an onium carboxylate structure, a trialkylamine structure, an aniline structure or a pyridine structure; an alkylamine derivative having a hydroxyl group and/or an ether bond; and an aniline derivative having a hydroxyl group and/or an ether bond.

Examples of the compound having an imidazole structure include imidazole, 2,4,5-triphenylimidazole and benzimidazole. Examples of the compound having a diazabicyclo structure include 1,4-diazabicyclo[2,2,2]octane, 1,5-diazabicyclo[4,3,0]non-5-ene and 1,8-diazabicyclo[5,4,0]undec-7-ene. Examples of the compound having an onium hydroxide structure include a triarylsulfonium hydroxide, a phenacylsulfonium hydroxide and a sulfonium hydroxide having a 2-oxoalkyl group, specifically, triphenylsulfonium hydroxide, tris(tert-butylphenyl)sulfonium hydroxide, bis(tert-butylphenyl)iodonium hydroxide, phenacylthiophenium hydroxide and 2-oxopropylthiophenium hydroxide. The compound having an onium carboxylate structure is a compound where the anion moiety of the compound having an onium hydroxide structure is converted into a carboxylate, and examples thereof include acetate, adamantane-1-carboxylate and perfluoroalkyl carboxylate. Examples of the compound having a trialkylamine structure include tri(n-butyl)amine and tri(n-octyl)amine. Examples of the aniline compound include 2,6-diisopropylaniline and N,N-dimethylaniline. Examples of the alkylamine derivative having a hydroxyl group and/or an ether bond include ethanolamine, diethanolamine, triethanolamine and tris-(methoxyethoxyethyl)amine. Examples of the aniline derivative having a hydroxyl group and/or an ether bond include N,N-bis(hydroxyethyl)aniline.

One of these basic compounds may be used alone, or two or more thereof may be used in combination. However, when the amount of the component (B) used is 0.05 mass % or more, the basic substance may or may not be used. In the case of using the basic compound, the amount used thereof is usually from 0.001 to 10 mass %, preferably from 0.01 to 5 mass %, based on the solid content of the photosensitive composition. The amount used is preferably 0.001 mass % or more for obtaining a sufficiently high addition effect and preferably 10 mass % or less in view of sensitivity and developability of unexposed area.

[8] (H) Fluorine- and/or Silicon-Containing Surfactant

The photosensitive composition of the present invention preferably further contains any one fluorine- and/or silicon-containing surfactant (a fluorine-containing surfactant, a silicon-containing surfactant or a surfactant containing both a fluorine atom and a silicon atom), or two or more thereof When the photosensitive composition of the present invention contains a fluorine- and/or silicon-containing surfactant, a resist pattern with good sensitivity, resolution and adhesion and less development defect can be obtained at the time of using an exposure light source of 250 nm or less, particularly 220 nm or less.

Examples of the fluorine- and/or silicon-containing surfactant include surfactants described in JP-A-62-36663, JP-A-61-226746, JP-A-61-226745, JP-A-62-170950, JP-A-63-34540, JP-A-7-230165, JP-A-8-62834, JP-A-9-54432, JP-A-9-5988, JP-A-2002-277862 and U.S. Pat. Nos. 5,405,720, 5,360,692, 5,529,881, 5,296,330, 5,436,098, 5,576,143, 5,294,511 and 5,824,451. The following commercially available surfactants each may also be used as it is.

Examples of the commercially available surfactant which can be used include a fluorine-containing surfactant and a silicon-containing surfactant, such as EFtop EF301 and EF303 (produced by Shin-Akita Kasei K.K.), Florad FC430 and 431 (produced by Sumitomo 3M Inc.), Megafac F171, F173, F176, F189 and R08 (produced by Dainippon Ink & Chemicals, Inc.), Surflon S-382, SC101, 102, 103, 104, 105 and 106 (produced by Asahi Glass Co., Ltd.), and Troysol S-366 (produced by Troy Chemical). In addition, a polysiloxane polymer KP-341 (produced by Shin-Etsu Chemical Co., Ltd.) may also be used as the silicon-containing surfactant.

Other than these known surfactants, a surfactant using a polymer having a fluoro-aliphatic group, which is derived from a fluoro-aliphatic compound produced by a telomerization process (also called a telomer process) or an oligomerization process (also called an oligomer process), may be used. The fluoro-aliphatic compound can be synthesized by the method described in JP-A-2002-90991.

The polymer having a fluoro-aliphatic group is preferably a copolymer of a fluoro-aliphatic group-containing monomer with a (poly(oxyalkylene)) acrylate and/or a (poly(oxyalkylene)) methacrylate, and the polymer may have an irregular distribution or may be a block copolymer. Examples of the poly(oxyalkylene) group include a poly(oxyethylene) group, a poly(oxypropylene) group and a poly(oxybutylene group). The poly(oxyalkylene) group may also be a unit having alkylenes differing in the chain length within the same chain, such as block-linked poly(oxyethylene, oxypropylene and oxyethylene) and block-linked poly(oxyethylene and oxypropylene). The copolymer of a fluoro-aliphatic group-containing monomer with a (poly(oxyalkylene)) acrylate (or methacrylate) may be not only a binary copolymer but also a ternary or greater copolymer obtained by simultaneously copolymerizing two or more different fluoro-aliphatic group-containing monomers or two or more different (poly(oxyalkylene)) acrylates (or methacrylates).

Examples thereof include commercially available surfactants such as Megafac F178, F-470, F-473, F-475, F-476 and F-472 (produced by Dainippon Ink & Chemicals, Inc.). Other examples include a copolymer of an acrylate (or a methacrylate) having a $C_6F_{13}$ group with a (poly(oxyalkylene)) acrylate (or methacrylate), a copolymer of an acrylate (or a methacrylate) having a $C_6F_{13}$ group with a (poly(oxyethylene)) acrylate (or methacrylate) and a (poly(oxypropylene)) acrylate (or methacrylate), a copolymer of an acrylate (or a methacrylate) having a $C_8F_{17}$ group with a (poly(oxyalkylene)) acrylate (or methacrylate), and a copolymer of an acrylate (or a methacrylate) having a $C_8F_{17}$ group with a (poly(oxyethylene)) acrylate (or methacrylate) and a (poly(oxypropylene)) acrylate (or methacrylate).

The amount of the fluorine- and/or silicon-containing surfactant used is preferably from 0.0001 to 2 mass %, more preferably from 0.001 to 1 mass %, based on the entire amount of the photosensitive composition (excluding the solvent).

[9] (I) Organic Solvent

The photosensitive composition of the present invention is used by dissolving the above-described components in a predetermined organic solvent.

Examples of the organic solvent which can be used include ethylene dichloride, cyclohexanone, cyclopentanone, 2-heptanone, γ-butyrolactone, methyl ethyl ketone, ethylene glycol monomethyl ether, ethylene glycol monoethyl ether, 2-methoxyethyl acetate, ethylene glycol monoethyl ether acetate, propylene glycol monomethyl ether, propylene glycol monomethyl ether acetate, toluene, ethyl acetate, methyl lactate, ethyl lactate, methyl methoxypropionate, ethyl ethoxypropionate, methyl pyruvate, ethyl pyruvate, propyl pyruvate, N,N-dimethylformamide, dimethylsulfoxide, N-methylpyrrolidone and tetrahydrofuran.

(Ia) Ketone-Based Solvent

The solvent for use in the present invention is preferably a solvent having at least one ketone structure.

The solvent having a ketone structure includes a chain ketone solvent and a cyclic ketone solvent. A compound having a total carbon number of 5 to 8 is preferred in view of good coatability.

Examples of the chain ketone solvent include 2-heptanone, methyl ethyl ketone and methyl isobutyl ketone, with 2-heptanone being preferred.

Examples of the cyclic ketone solvent include cyclopentanone, 3-methyl-2-cyclopentanone, cyclohexanone, 2-methylcyclohexanone, 2,6-dimethylcyclohexanone, cycloheptanone, cyclooctanone and isophorone, with cyclohexanone and cycloheptanone being preferred.

The solvent is preferably used as a sole solvent having a ketone structure or as a mixed solvent with another solvent. Examples of the solvent mixed (solvent used in combination) include a propylene glycol monoalkyl ether carboxylate, an alkyl lactate, a propylene glycol monoalkyl ether, an alkyl alkoxypropionate and a lactone compound.

Examples of the propylene glycol monoalkyl ether carboxylate include propylene glycol monomethyl ether acetate, propylene glycol monomethyl ether propionate and propylene glycol monoethyl ether acetate.

Examples of the alkyl lactate include methyl lactate and ethyl lactate.

Examples of the propylene glycol monoalkyl ether include propylene glycol monomethyl ether and propylene glycol monoethyl ether.

Examples of the alkyl alkoxypropionate include methyl methoxypropionate, ethyl methoxypropionate, methyl ethoxypropionate and ethyl ethoxypropionate.

Examples of the lactone compound include γ-butyrolactone.

The solvent used in combination is preferably a propylene glycol monoalkyl ether carboxylate, an alkyl lactate or a propylene glycol monoalkyl ether, more preferably propylene glycol monomethyl ether acetate.

By virtue of mixing the ketone-based solvent and the solvent used in combination, adhesion to substrate, developability, DOF and the like are improved.

The ratio (by mass) of the ketone-based solvent and the solvent used in combination is preferably from 10/90 to 95/5, more preferably from 20/80 to 80/20, still more preferably from 30/70 to 70/30.

From the standpoint of enhancing the film thickness uniformity or development defect performance, a high boiling point solvent having a boiling point of 200° C. or more, such as ethylene carbonate and propylene carbonate, may be mixed.

The amount of the high boiling point solvent added is usually from 0.1 to 15 mass %, preferably from 0.5 to 10 mass %, more preferably from 1 to 5 mass %, based on the entire solvent.

In the present invention, a photosensitive composition having a solid content concentration of usually from 3 to 25 mass %, preferably from 5 to 22 mass %, more preferably from 5 to 15 mass %, is prepared by using a solvent alone, preferably by using two or more kinds of solvents.

<Other Additives>

If desired, the photosensitive composition of the present invention may further contain, for example, a dye, a plasticizer, a surfactant other than the component (H), a photosensitizer, and a compound capable of accelerating the solubility in a developer.

The compound capable of accelerating the dissolution in a developer, which can be used in the present invention, is a low molecular compound containing two or more phenolic OH groups or one or more carboxy group and having a molecular weight of 1,000 or less. In the case of containing a carboxyl group, an alicyclic or aliphatic compound is preferred.

The amount of the dissolution accelerating compound added is preferably from 2 to 50 mass %, more preferably from 5 to 30 mass %, based on the resin of component (C) or the resin of component (E). The amount added is preferably 50 mass % or less from the standpoint of suppressing development residue or preventing pattern deformation at the development.

The phenol compound having a molecular weight of 1,000 or less can be easily synthesized by one skilled in the art by referring to the method described, for example, in JP-A-4-122938, JP-A-2-28531, U.S. Pat. No. 4,916,210 and European Patent 219294.

Specific examples of the alicyclic or aliphatic compound having a carboxy group include, but are not limited to, a carboxylic acid derivative having a steroid structure, such as cholic acid, deoxycholic acid and lithocholic acid, an adamantane carboxylic acid derivative, an adamantane dicarboxylic acid, a cyclohexanecarboxylic acid and a cyclohexanedicarboxylic acid.

In the present invention, a surfactant other than the fluorine- and/or silicon-containing surfactant (H) may also be added. Specific examples thereof include a nonionic surfactant such as polyoxyethylene alkyl ethers, polyoxyethylene alkylallyl ethers, polyoxyethylene-polyoxypropylene block copolymers, sorbitan fatty acid esters and polyoxyethylene sorbitan fatty acid esters.

One of these surfactants may be used alone or some of these surfactants may be used in combination.

(Pattern Forming Method)

The photosensitive composition of the present invention is used by dissolving the above-described components in a predetermined organic solvent, preferably a mixed solvent described above, and coating the obtained solution on a predetermined support as follows.

For example, the photosensitive composition is coated on a substrate (e.g., silicon/silicon dioxide-coated substrate) as used in the production of a precision integrated circuit device, by an appropriate coating method such as spinner or coater, and dried to form a photosensitive film.

This photosensitive film is irradiated with actinic rays or radiation through a predetermined mask, preferably subjected to baking (heating), and then developed, whereby a good pattern can be obtained.

At the irradiation with actinic rays or radiation, the exposure may be performed by filling a liquid having a refractive index higher than that of air between the photosensitive film and the lens (immersion exposure). By this exposure, resolution can be elevated.

Examples of the actinic ray or radiation include infrared light, visible light, ultraviolet light, far ultraviolet light, X-ray and electron beam. Among these, preferred is far ultraviolet light at a wavelength of 250 nm or less, more preferably 220 nm or less. Specifically, a KrF excimer laser (248 nm), an ArF excimer laser (193 nm), an $F_2$ excimer laser (157 nm), an X-ray, an electron beam and the like are used. An ArF excimer laser, an $F_2$ excimer laser, EUV (13 nm) and an electron beam are preferred.

(Immersion Exposure)

In the case where the photosensitive composition of the present invention is immersion-exposed, from the standpoint of enhancing the resolving power, the photosensitive composition is preferably used to give a film thickness of 30 to 250 nm, more preferably from 30 to 100 nm. Such a film thickness can be obtained by setting the solid content concentration of the photosensitive composition to an appropriate range so as to impart a proper viscosity and thereby enhance the coatability and film-forming property.

The entire solid content concentration of the photosensitive composition is generally from 1 to 10 mass %, preferably from 1 to 8 mass %, more preferably from 1.0 to 6.0 mass %.

In the case of immersion-exposing the photosensitive composition of the present invention, the photosensitive composition is used by dissolving the above-described components in a predetermined organic solvent, preferably a mixed solvent described above, and coating the obtained solution on a predetermined support as follows.

That is, the photosensitive composition is coated on a substrate (e.g., silicon/silicon dioxide-coated substrate) as used in the production of a precision integrated circuit device, to an arbitrary thickness (usually from 30 to 500 nm) by an appropriate coating method such as spinner or coater. After the coating, the resist film is washed with water for immersion, if desired. The washing time is usually from 5 seconds to 5 minutes.

Subsequently, the resist coated is dried by spinning or baking to form a resist film, and the resist film is exposed with intervention of immersion water through a mask or the like for the pattern formation (immersion exposure). For example, the exposure is performed in the state that an immersion liquid is filled between the resist film and the optical lens. The exposure amount can be appropriately selected but is usually from 1 to 100 mJ/cm$^2$. After the exposure, the resist film is washed with water for immersion, if desired. The washing time is usually from 5 seconds to 5 minutes. The resist film is preferably subjected to spinning or/and drying and then to development and rinsing, whereby a good pattern is obtained. The baking is preferably performed and the baking temperature is usually from 30 to 300° C. In view of PED described above, the time from exposure to the baking step is preferably shorter.

The exposure light used here is preferably a far ultraviolet ray at a wavelength of 250 nm or less, more preferably 220 nm or less. Specifically, a KrF excimer laser (248 nm), an ArF excimer laser (193 nm), an $F_2$ excimer laser (157 nm), an X-ray and the like are used.

Incidentally, the change in performance observed when applying the resist to immersion exposure is considered to occur because of the contact of the resist surface with the immersion liquid.

The immersion liquid used in the immersion exposure is described below.

The immersion liquid is preferably a liquid transparent to light at the exposure wavelength and having a refractive index of which temperature constant is as small as possible so as to minimize the distortion of an optical image projected on the resist. Particularly, when the exposure light source is an ArF excimer laser (wavelength: 193 nm), water is preferably used in view of easy availability and easy handleability, in addition to the above-described aspects.

Furthermore, a medium having a refractive index of 1.5 or more may also be used from the viewpoint that the refractive index can be enhanced. This medium may be an aqueous solution or an organic solvent.

In the case of using water as the immersion liquid, for the purpose of decreasing the surface tension of water and increasing the surface activity, an additive (liquid) which does not dissolve the resist layer on a wafer and at the same time, gives only a negligible effect on the optical coat on the lower surface of the lens element, may be added at a small ratio. The additive is preferably an aliphatic alcohol having a refractive index nearly equal to that of water, and specific examples thereof include methyl alcohol, ethyl alcohol and isopropyl alcohol. By virtue of adding an alcohol having a refractive index nearly equal to that of water, even when the alcohol component in water is evaporated and the content concentration is changed, the change in the refractive index of the entire liquid can be advantageously made very small. On the other hand, if a substance opaque to light at 193 nm or an impurity greatly differing in the refractive index from water is mingled, this incurs distortion of the optical image projected on the resist. Therefore, the water used is preferably distilled water. Pure water resulting from further filtration through an ion exchange filter or the like may also be used.

The electrical resistance of the water is preferably 18.3 MΩcm or more, and the TOC (organic concentration) is preferably 20 ppb or less. Furthermore, the water is preferably degassed before use.

Also, the lithographic performance can be enhanced by elevating the refractive index of the immersion liquid. From this standpoint, an additive for elevating the refractive index may be added to the water, or heavy water ($D_2O$) may be used in place of water.

In order to prevent the resist film from directly contacting with the immersion liquid, an immersion liquid sparingly soluble film (hereinafter sometimes referred to as "a topcoat") may be provided between the immersion liquid and the resist film formed from the photosensitive composition of the present invention. Preferred functions required of the topcoat are suitability for coating on the resist upper layer part, transparency to radiation particularly at 193 nm, and sparing solubility in the immersion liquid. The topcoat preferably does not intermix with the resist and can be uniformly coated on the resist upper layer.

In view of transparent to light at 193 nm, the topcoat is preferably an aromatic-free polymer, and specific examples thereof include a hydrocarbon polymer, an acrylic acid ester polymer, a polymethacrylic acid, a polyacrylic acid, a polyvinyl ether, a silicon-containing polymer and a fluorine-containing polymer.

At the time of peeling off the topcoat, a developer may be used or a releasing agent may be separately used. The releasing agent is preferably a solvent less permeating into the resist. From the standpoint that the peeling step can be performed simultaneously with the resist development step, the topcoat is preferably peelable with an alkali developer and in view of peeling with an alkali developer, the topcoat is preferably acidic, but in view of non-intermixing with the resist, the topcoat may be neutral or alkaline.

With no difference in the refractive index between the topcoat and the immersion liquid, the resolving power is enhanced. In the case where the exposure light source is an ArF excimer laser (wavelength: 193 nm), water is preferably used as the immersion liquid and therefore, the topcoat for ArF immersion exposure preferably has a refractive index close to the refractive index (1.44) of water. Also, in view of transparency and refractive index, the topcoat is preferably a thin film.

In the case of using an organic solvent as the immersion liquid, the topcoat is preferably water-soluble.

In the development step, an alkali developer is used as follows. The alkali developer usable for the resist composition is an alkaline aqueous solution containing an alkali such as inorganic alkalis (e.g., sodium hydroxide, potassium hydroxide, sodium carbonate, sodium silicate, sodium metasilicate, aqueous ammonia), primary amines (e.g., ethylamine, n-propylamine), secondary amines (e.g., diethylamine, di-n-butylamine), tertiary amines (e.g., triethylamine, methyldiethylamine), alcohol amines (e.g., dimethylethanolamine, triethanolamine), quaternary ammonium salt (e.g., tetramethylammonium hydroxide, tetraethylammonium hydroxide) and cyclic amines (e.g., pyrrole, piperidine).

In the alkali developer, alcohols and a surfactant may also be added in an appropriate amount.

The alkali concentration of the alkali developer is usually from 0.1 to 20 mass %.

The pH of the alkali developer is usually from 10.0 to 15.0.

EXAMPLES

The present invention is described in greater detail below by referring to Examples, but the present invention should not be construed as being limited thereto.

Synthesis Example of Compound (A)

Synthesis Example 1

Synthesis of Compound (A-1)

In a nitrogen stream, a mixture containing 5.0 g (15.8 mmol) of 1,1,2,2,3,3-hexafluoropropane-1,3-disulfonyl difluoride and 50 mL of THF was ice-cooled and thereto, 16.6 mL (16.6 mmol) of a THF solution of 1.0 M-$CH_3MgBr$ was added dropwise over 10 minutes. The resulting solution was stirred under ice cooling for 1 hour and further stirred at room temperature for 1 hour. Thereafter, 50 mL of water and 50 mL of ethyl acetate were added, and the organic layer was washed with water, an aqueous saturated ammonium chloride solution and water in this order and then dried over sodium sulfate. After concentrating the solvent, the residue was washed with ether to obtain 2.0 g of $MO_3S(CF_2)_3SO_2F$ (M=Mg or Na) as a white solid.

Subsequently, 1.85 g of the obtained solid was dissolved in 100 mL of methanol and after adding thereto 1.81 g (5.38 mmol) of triphenylsulfonium bromide, the resulting solution was stirred at room temperature for 3 hours. Furthermore, 200 mL of chloroform was added, the organic layer was washed with water, and the solvent was removed to obtain 3.0 g of the objective Compound (A-1) as a colorless oil.

$^1$H-NMR (400 MHz, CDCl$_3$): δ 7.84-7.93 (m, 15H).
$^{19}$F-NMR (400 MHz, CDCl$_3$): δ −119 (m, 2F), −115 (m, 2F), −107 (m, 2F), 44 (s, 1F).

Synthesis Example 2

Synthesis of Compound (A-1)

The synthesis was performed in the same manner as in Synthesis Example 1 except for changing the THF solution of 1.0 M-CH$_3$MgBr to an aqueous 1.0 M-NaOH solution, whereby 2.5 g of NaO$_3$S(CF$_2$)$_3$SO$_2$F was obtained as a white solid.

From 1.85 g of this solid, 3.0 g of the objective Compound (A-1) was obtained as a colorless oil by performing the subsequent synthesis in the same manner.

Synthesis Example 3

Synthesis of Compound (A-7)

In a nitrogen stream, a mixture containing 5.0 g (15.8 mmol) of 1,1,2,2,3,3-hexafluoropropane-1,3-disulfonyl difluoride and 20 mL of triethylamine was ice-cooled and after adding thereto 2.36 g (15.8 mmol) of trifluoromethanesulfonamide, the resulting mixture was refluxed for 10 hours. Subsequently, 100 ml of ethyl acetate was added, and the organic layer was washed with water several times and then dried over sodium sulfate to obtain 6.3 g of triethylammonium salt of CF$_3$SO$_2$N—SO$_2$(CF$_2$)$_3$SO$_2$F as a brown oil.

Subsequently, 100 mL of chloroform, 100 mL of water and 1.89 g (5.51 mmol) of triphenylsulfonium bromide were added to 3.0 g of the solid obtained above, and the resulting mixture was stirred at room temperature for 3 hours. Thereafter, the organic layer was separated and washed with water, and the solvent was removed to obtain 2.9 g of the objective Compound (A-7) as a brown oil.

$^1$H-NMR (400 MHz, CDCl$_3$): δ 7.84-7.93 (m, 15H).
$^{19}$F-NMR (400 MHz, CDCl$_3$): δ −119 (m, 2F), −113 (m, 2F), −108 (m, 2F), −80 (s, 3F), 44 (s, 1F).

MALDI TOF-MS:
calcd. for C$_4$F$_{10}$NO$_6$S$_3$$^-$ (M−): 443.8734, found: 443.8006
Other compounds (A) were synthesized in the same manner.

<Resin (C)>
The structure, molecular weight and dispersity of the resin (C) used in Examples are shown below. The numeral on the right side of the repeating unit indicates the molar ratio (hereinafter the same).

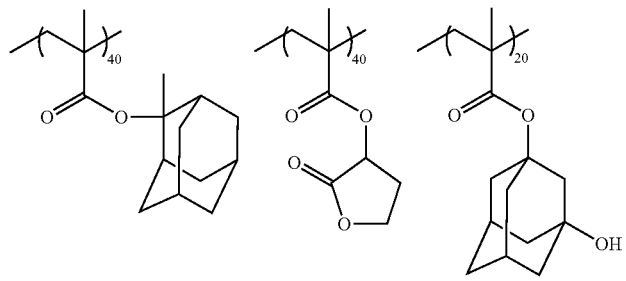

(RA-1)

Mw = 10700
Mw/Mn = 1.81

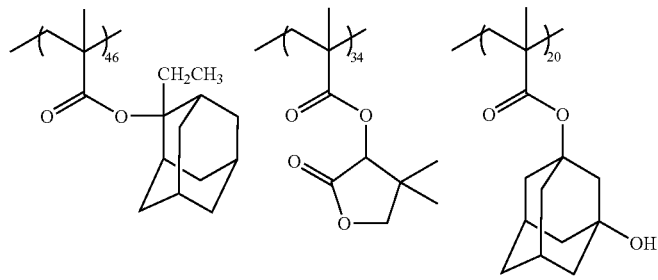

(RA-2)

Mw = 9400
Mw/Mn = 1.78

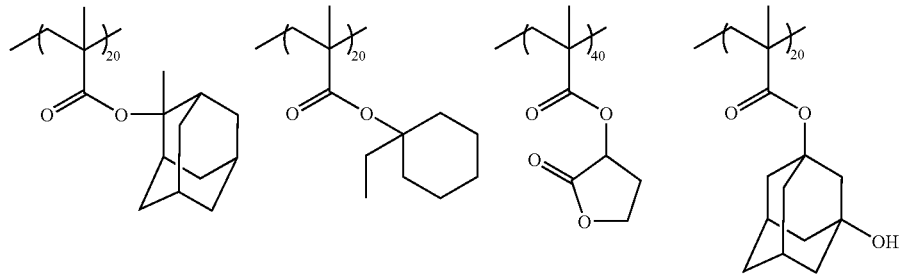

(RA-3)

Mw = 13700
Mw/Mn = 1.89

-continued
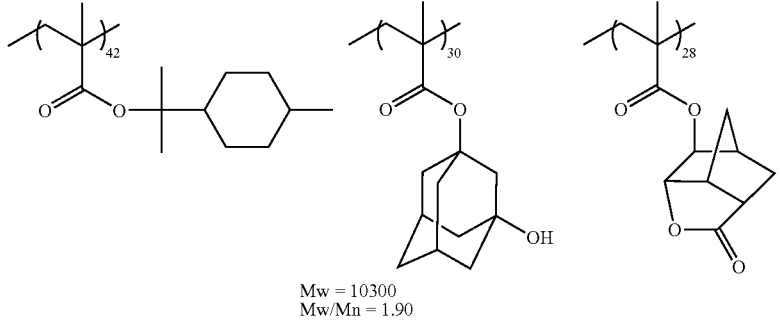
(RA-4)
Mw = 10300
Mw/Mn = 1.90
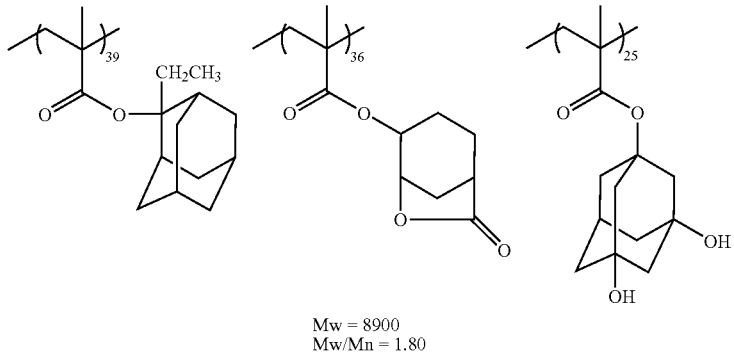
(RA-5)
Mw = 8900
Mw/Mn = 1.80
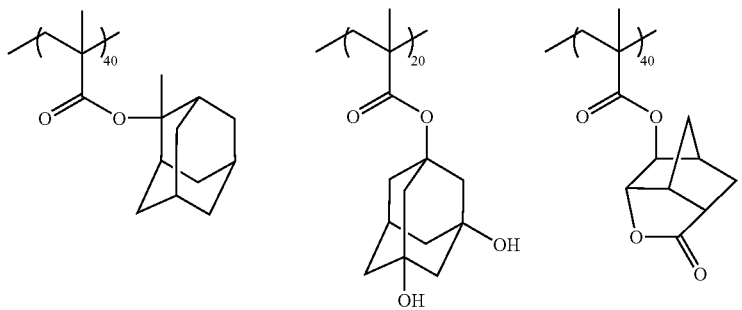
(RA-6)
Mw = 7900
Mw/Mn = 1.73
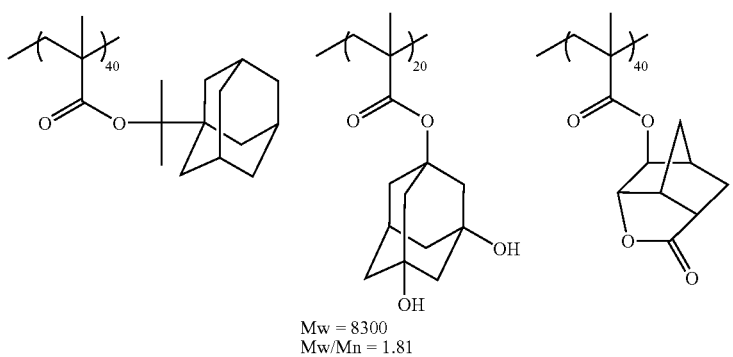
(RA-7)
Mw = 8300
Mw/Mn = 1.81

(RA-8)
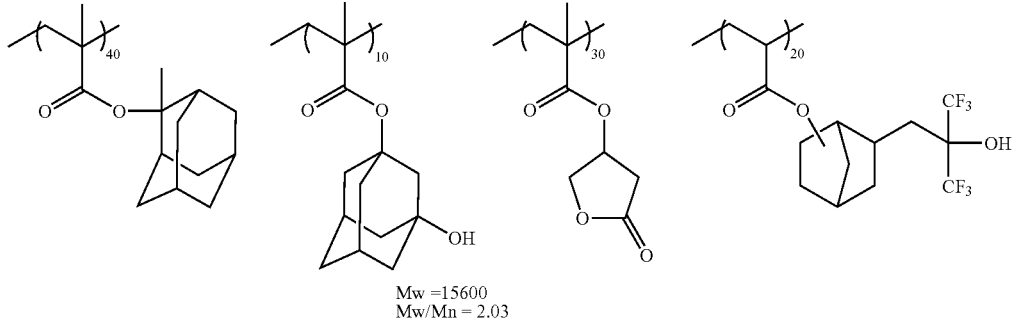
Mw =15600
Mw/Mn = 2.03
(RA-9)
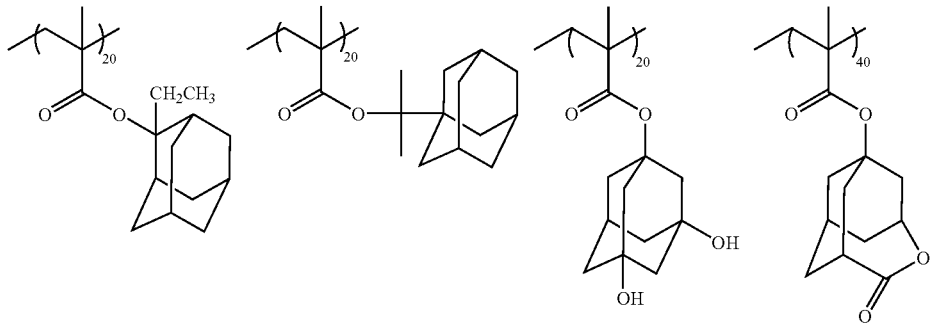
Mw = 9800
Mw/Mn = 1.86
(RA-10)
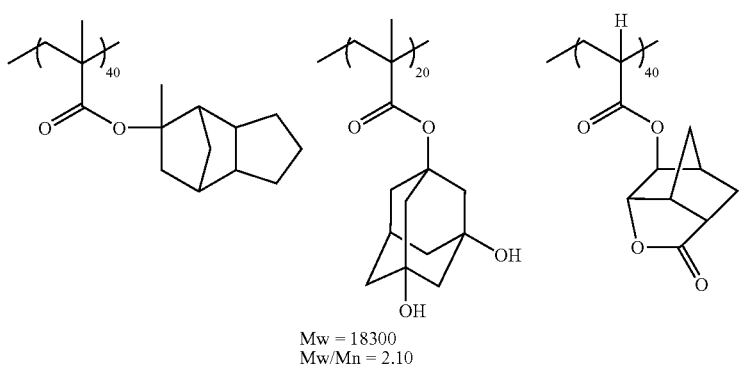
Mw = 18300
Mw/Mn = 2.10
(RA-11)
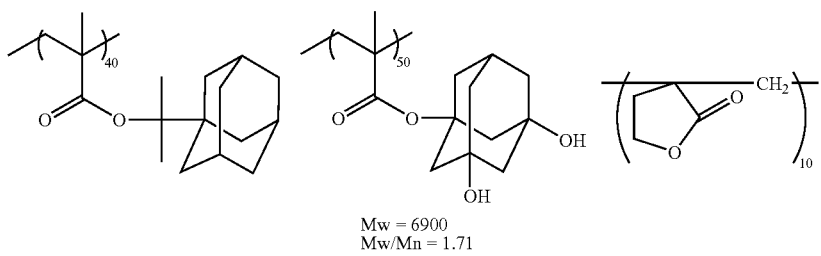
Mw = 6900
Mw/Mn = 1.71

-continued
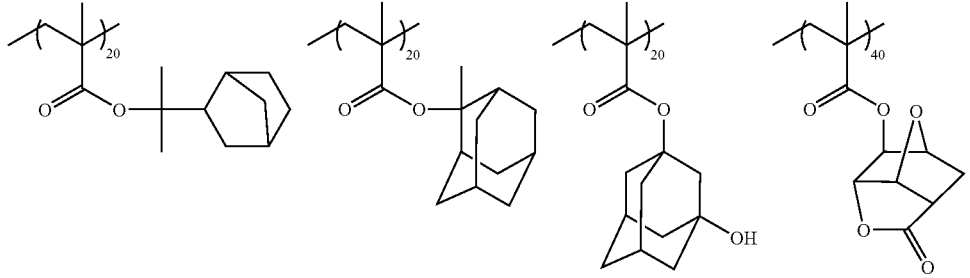
(RA-12)
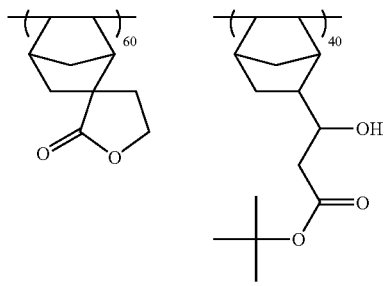
(RA-13)
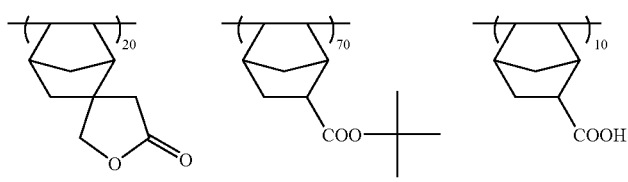
(RA-14)
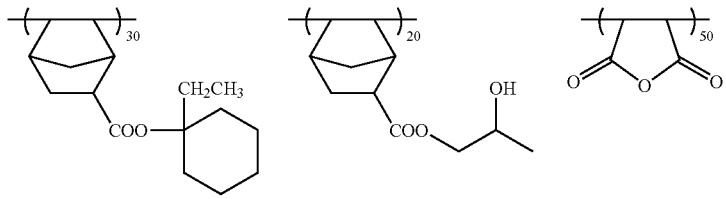
(RA-15)
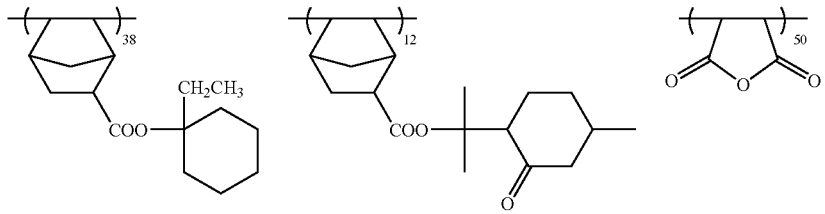
(RA-16)

-continued
(RA-17)
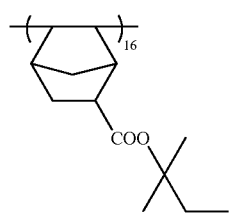 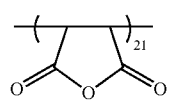 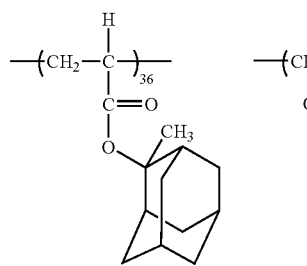 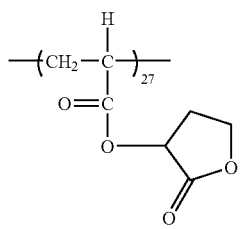
Mw = 13900
Mw/Mn = 1.98
(RA-18)
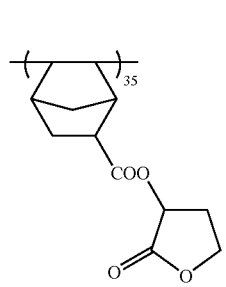 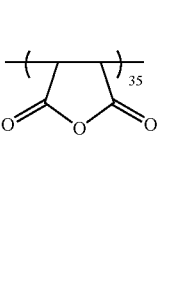 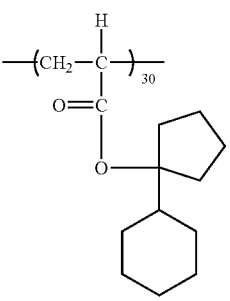
Mw = 12700
Mw/Mn = 1.99
(RA-19)
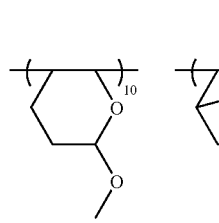 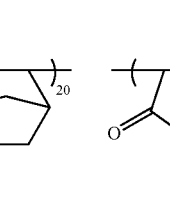 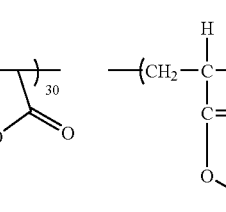 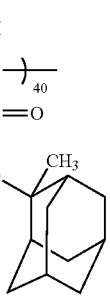
Mw = 9300
Mw/Mn = 1.81
(RA-20)
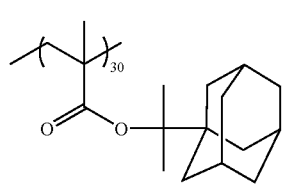 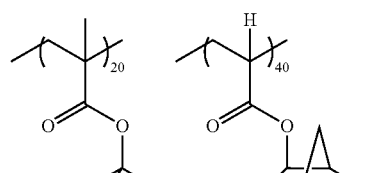 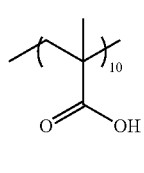
Mw = 7600
Mw/Mn = 1.76

(RA-21)
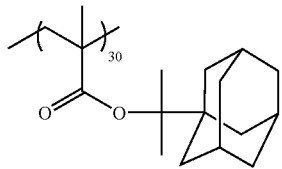 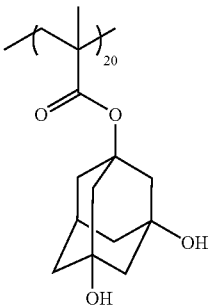 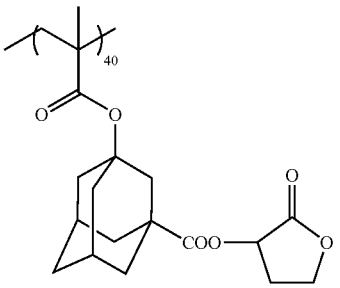 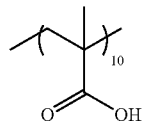
Mw = 12700
Mw/Mn = 1.86
(RA-22)
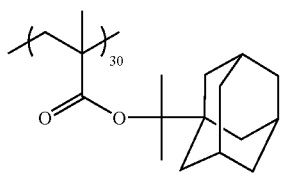 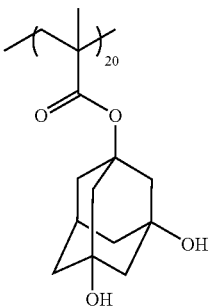 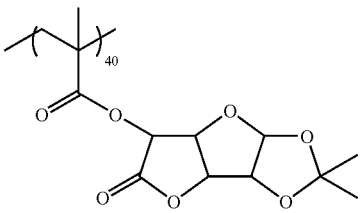 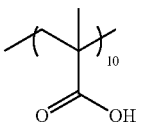
Mw = 8200
Mw/Mn = 1.75
(RA-23)
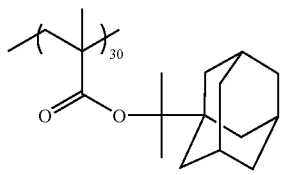 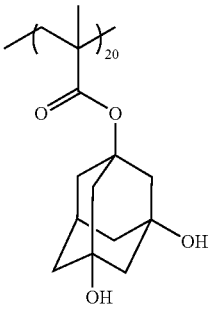 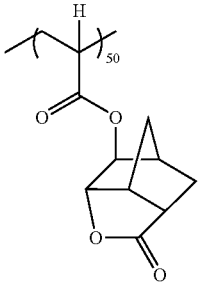
Mw = 8500
Mw/Mn = 1.77
(RA-24)
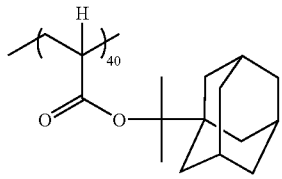 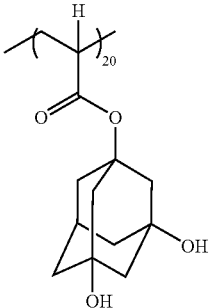 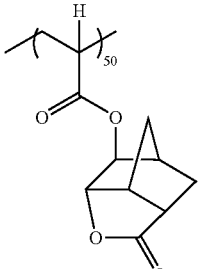
Mw = 18900
Mw/Mn = 2.13

-continued

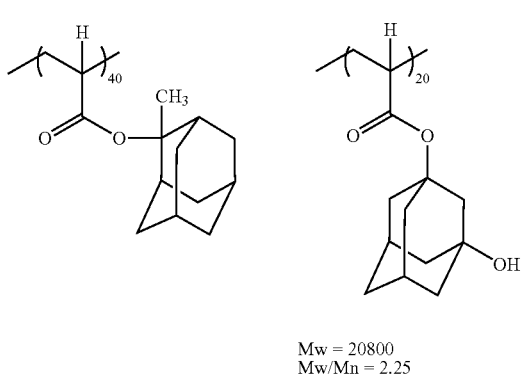

(RA-25)

Mw = 20800
Mw/Mn = 2.25

Examples 1 to 18 and Comparative Examples 1 to 3

Preparation of Resist

The components shown in Table 1 below were dissolved in a solvent to prepare a solution having a solid content concentration of 12 mass %, and this solution was filtered through a 0.1-μm polytetrafluoroethylene filter or polyethylene filter to prepare a positive resist solution. The positive resist solution prepared was evaluated by the following methods. The results obtained are shown in Table 1.

<Evaluation of Resist>

An antireflection film DUV-42 produced by Brewer Science Co., Ltd. was uniformly coated on a silicon substrate treated with hexamethyldisilazane by a spin coater to a thickness of 600 Å, dried on a hot plate at 100° C. for 90 seconds and then dried under heating at 190° C. for 240 seconds. Thereafter, each positive resist solution was coated by a spin coater and dried at 120° C. for 90 seconds to form a resist film of 0.25 μm.

The formed resist film was exposed by an ArF excimer laser stepper (manufactured by ISI, NA=0.6) through a mask and immediately after the exposure, heated on a hot plate at 120° C. for 90 seconds. Furthermore, the resist film was developed with an aqueous 2.38 mass % tetramethylammonium hydroxide solution at 23° C. for 60 seconds, rinsed with pure water for 30 seconds and dried to obtain a line pattern.

PEB Temperature Dependency:

Assuming that the exposure amount necessary for reproducing a line-and-space (1/1) pattern with a mask size of 130 nm at the time of heating at 120° C. for 90 seconds is an optimal exposure amount, the resist film was exposed with the optimal exposure amount and then post-heated at two kinds of temperatures of +2° C. and −2° C. (122° C. and 118° C.) with respect to the post-heating temperature, each line-and-space pattern obtained was length-measured, and the line widths $L_1$ and $L_2$ were determined. The PEB temperature dependency was defined as the fluctuation in the line width per 1° C. of the PEB temperature change and calculated according to the following formula:

PEB Temperature dependency (nm/° C.)=$|L_1-L_2|/4$

As the value is smaller, the performance is better and less changes due to temperature change.

Exposure Latitude:

Assuming that the exposure amount necessary for reproducing a line-and-space mask pattern with a line width of 90 nm is an optimal exposure amount, the exposure amount width allowing for a pattern size of 90 nm±10% was determined by varying the exposure amount, and this value was divided by the optimal exposure amount and expressed in percentage. As the value is larger, the performance less changes due to change of exposure amount and the exposure latitude is better.

Pattern Profile:

Assuming that the exposure amount necessary for reproducing a line-and-space mask pattern with a line width of 90 nm is an optimal exposure amount, the profile at the optimal exposure amount was observed by a scanning electron microscope (SEM).

TABLE 1

| | | | | | | | | |
|---|---|---|---|---|---|---|---|---|
| | ArF, Positive | | | | | | | |
| | Compound (A) | (g) | Acid Generator | (g) | Resin (10 g) | Basic Compound | (g) | Surfactant (0.03 g) |
| Example | | | | | | | | |
| 1 | A-2 | (0.2) | z38 | (0.3) | RA-1 | PEA/TPA | (0.01/0.02) | W-4 |
| 2 | A-1 | (0.4) | z60 z38 | (0.12) (0.3) | RA-20 | PEA/DIA | (0.01/0.02) | W-4 |
| 3 | A-4 | (0.2) | z63 | (0.4) | RA-22 | PEA/DIA | (0.02/0.02) | W-4 |
| 4 | A-5 | (0.3) | z58 | (0.3) | RA-20 | DIA | (0.02) | W-4 |
| 5 | A-6 | (0.3) | z57 | (0.32) | RA-8 | PEA | (0.02) | W-4 |
| 6 | A-7 | (0.3) | z61 | (0.3) | RA-25 | PEA | (0.03) | W-4 |
| 7 | A-9 | (0.2) | z50 | (0.4) | RA-24 | PEA/DIA | (0.01/0.01) | W-1 |
| 8 | A-1 | (0.3) | z58 | (0.4) | RA-4 | PEA | (0.02) | W-4 |

TABLE 1-continued

| | | | | | ArF, Positive | | | |
|---|---|---|---|---|---|---|---|---|
| 9 | A-8 | (0.4) | z38 | (0.3) | RA-23 | PEA | (0.02) | W-2 |
| 10 | A-31 | (0.3) | z59 | (0.4) | RA-20 | PEA | (0.02) | W-4 |
| 11 | A-7 | (0.2) | z58 z60 | (0.1) (0.3) | RA-22 | PEA | (0.02) | W-4 |
| 12 | A-7 | (0.3) | z34 | (0.4) | RA-21 | PEA | (0.03) | W-2 |
| 13 | A-16 | (0.2) | z61 | (0.3) | RA-7 | PEA | (0.02) | W-4 |
| 14 | A-18 | (0.3) | z63 | (0.5) | RA-8 | TMEA | (0.02) | W-4 |
| 15 | A-28 | (0.2) | z38 | (0.4) | RA-21 | PEA | (0.03) | W-2 |
| 16 | A-35 | (0.4) | z58 | (0.4) | RA-21 | PEA/DIA | (0.02/0.02) | W-4 |
| 17 | A-39 | (0.3) | z38 | (0.5) | RA-19 | DIA | (0.02) | W-4 |
| 18 | A-1 | (0.3) | — | (—) | RA-20 | — | (—) | — |
| Comparative Example | | | | | | | | |
| 1 | none | (—) | z38 | (0.3) | RA-4 | DIA | (0.03) | W-4 |
| 2 | TPSB | (0.3) | z38 | (0.4) | RA-20 | PEA/DIA | (0.01/0.02) | W-4 |
| 3 | TPSPB | (0.2) | z38 | (0.3) | RA-7 | TMEA | (0.03) | W-4 |

| | Solvent | (ratio by mass) | Dissolution Inhibiting Compound (g) | PEB Temperature Dependency (nm/° C.) | Exposure Latitude (%) | Pattern Profile |
|---|---|---|---|---|---|---|
| Example | | | | | | |
| 1 | A1/B1 | (60/40) | | 3.3 | 21.4 | slightly tapered |
| 2 | A1/B1 | (80/20) | | 3.8 | 18.4 | rectangular |
| 3 | A1/B1 | (60/40) | | 3.2 | 20.9 | rectangular |
| 4 | A1/B1 | (80/20) | | 3.3 | 23.5 | rectangular |
| 5 | A1/A3 | (80/20) | | 3.3 | 16.6 | rectangular |
| 6 | A1/B1 | (60/40) | | 4.2 | 19.9 | rectangular |
| 7 | A1/B2 | (80/20) | | 2.9 | 18.9 | rectangular |
| 8 | A1/A3 | (60/40) | | 3.3 | 20.4 | rectangular |
| 9 | A1/B1 | (70/30) | LCB (0.3) | 3.5 | 17.9 | rectangular |
| 10 | A1/A4 | (60/40) | | 3.2 | 19.9 | rectangular |
| 11 | A1/B1 | (60/40) | LCB (0.5) | 3.7 | 17.9 | rectangular |
| 12 | A1/A4 | (70/30) | | 3.3 | 20.4 | rectangular |
| 13 | A1/B1 | (80/20) | | 4.5 | 17.9 | rectangular |
| 14 | A1/A3 | (60/40) | | 3.4 | 15.8 | rectangular |
| 15 | A1/B1 | (60/40) | | 3.5 | 19.4 | rectangular |
| 16 | A1/B1 | (80/20) | | 3.3 | 20.9 | rectangular |
| 17 | A1/B1 | (60/40) | | 3.5 | 20.4 | rectangular |
| 18 | A1/B1 | (60/40) | | 4.7 | 15.5 | rectangular |
| Comparative Example | | | | | | |
| 1 | A1/B1 | (60/40) | — | 8.3 | 9.8 | tapered |
| 2 | A1/B1 | (60/40) | — | 7.2 | 9.6 | tapered |
| 3 | A1/B1 | (60/40) | — | 8.3 | 11.3 | tapered |

Abbreviations common in respective Tables are shown below together.

[Comparative Compound]
The abbreviations of comparative compounds used in Comparative Examples indicated the following.
TPSB: triphenylsulfonium pentafluorobenzenesulfonate

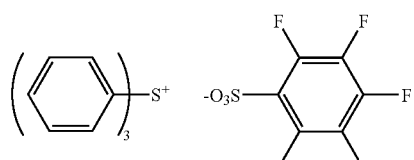

TPSPB: triphenylsulfonium perfluorobutanesulfonate

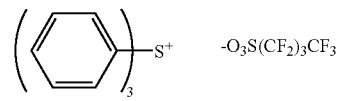

[Basic Compound]
TPI: 2,4,5-triphenylimidazole
TPSA: triphenylsulfonium acetate
HEP: N-hydroxyethylpiperidine
DIA: 2,6-diisopropylaniline
DCMA: dicyclohexylmethylamine
TPA: tripentylamine
HAP: hydroxyantipyrine TBAH: tetrabutylammonium hydroxide
TMEA: tris(methoxyethoxyethyl)amine
PEA: N-phenyldiethanolamine
TOA: trioctylamine
DBN: 1,5-diazabicyclo[4.3.0]non-5-ene

[Surfactant]
W-1: Megafac F176 (produced by Dainippon Ink & Chemicals, Inc.) (fluorine-containing)
W-2: Megafac R08 (produced by Dainippon Ink & Chemicals, Inc.) (fluorine- and silicon-containing)
W-3: polysiloxane polymer KP-341 (produced by Shin-Etsu Chemical Co., Ltd.) (silicon-containing)
W-4: Troysol S-366 (produced by Troy Chemical)

[Solvent]
A1: propylene glycol monomethyl ether acetate
A2: 2-heptanone
A3: cyclohexanone
A4: γ-butyrolactone
B1: propylene glycol monomethyl ether
B2: ethyl lactate

[Dissolution Inhibiting Compound]
LCB: tert-butyl lithocholate

As apparent from the results in Table 1, the photosensitive composition of the present invention ensures excellent property in the PEB temperature dependency, exposure latitude and pattern profile at the ArF exposure.

[Evaluation of Immersion Exposure]
<Preparation of Resist>

The components of each of Examples 1 to 18 shown in Table 1 were dissolved in a solvent to prepare a solution having a solid content concentration of 8 mass %, and this solution was filtered through a 0.1-μm polyethylene filter to prepare a positive resist solution. The prepared positive resist solutions were evaluated by the following methods.

<Evaluation of Resolution>

An organic antireflection film ARC29A (produced by Nissan Chemical Industries, Ltd.) was coated on a silicon wafer and baked at 205° C. for 60 seconds to form a 78-nm antireflection film. On this film, the resist composition prepared was coated and baked at 120° C. for 60 seconds to form a 150-nm resist film. The thus-obtained wafer was subjected to two-beam interference exposure (wet exposure) by using pure water as the immersion liquid. In the two-beam interference exposure (wet exposure), as shown in FIG. 1, the wafer 10 with an antireflection film and a resist film was exposed through a prism 8 and an immersion liquid (pure water) 9 by using a laser 1, a diaphragm 2, a shutter 3, three reflecting mirrors 4, 5 and 6, and a condenser lens 7. The wavelength of the laser 1 used was 193 nm, and a prism of forming a 65-nm line-and-space pattern 8 was used. Immediately after the exposure, the resist film was heated at 120° C. for 60 seconds, then developed with an aqueous tetramethylammonium hydroxide solution (2.38%) for 60 seconds and after rinsing with pure water, spin-dried. The obtained resist pattern was observed by a scanning electron microscope (S-9260, manufactured by Hitachi Ltd.), as a result, a 65-nm line-and-space pattern was resolved.

The compositions of Examples 1 to 18 were found to exhibit good image-forming capability also in the exposure through an immersion liquid.

Examples 19 to 24 and Comparative Examples 4 to 6

(1) Formation of Lower Resist Layer

FHi-028DD Resist (resist for i-line, produced by Fujifilm Olin Co., Ltd.) was coated on a 6-inch silicon wafer by using a spin coater, Mark 8, manufactured by Tokyo Electron Ltd. and then baked at 90° C. for 90 seconds to obtain a uniform film having a thickness of 0.55 μm.

This film was further heated at 200° C. for 3 minutes to form a lower resist layer having a thickness of 0.40 μm.

(2) Formation of Upper Resist Layer

The components shown in Table 2 below were dissolved in a solvent to prepare a solution having a solid content concentration of 11 mass %, and this solution was microfiltered through a membrane filter having a pore size of 0.1 μm to prepare an upper resist composition.

This upper resist composition was coated on the lower resist layer in the same manner and heated at 130° C. for 90 seconds to form an upper resist layer having a thickness of 0.20 μm.

Resins (SI-1) to (SI-5) in Table 2 are shown below.

(3) Evaluation of Resist

The wafer obtained above was exposed by an ArF excimer stepper 9300 (manufactured by ISI) having mounted thereon a resolving power mask, while changing the exposure amount.

Subsequently, the wafer was heated at 120° C. for 90 seconds, developed with a tetrahydroammonium hydroxide developer (2.38 mass %) for 60 seconds, rinsed with distilled water and dried to form an upper layer pattern. The PEB temperature dependency, exposure latitude and pattern profile were evaluated in the same manner as in Example 1.

The results obtained are shown in Table 2.

TABLE 2

| | Silicon-Containing, Positive | | | | | | | |
|---|---|---|---|---|---|---|---|---|
| | Compound (A) | (g) | Acid Generator | (g) | Resin (10 g) | Basic Compound | (g) | Surfactant (0.03 g) |
| Example | | | | | | | | |
| 19 | A-1 | (0.2) | z38 | (0.4) | SI-1 | PEA | (0.02) | W-4 |
| 20 | A-7 | (0.2) | z38 | (0.3) | SI-1 | PEA | (0.025) | W-4 |
| 21 | A-16 | (0.1) | z58 | (0.4) | SI-2 | DIA | (0.02) | W-3 |
| 22 | A-28 | (0.3) | z59 | (0.4) | SI-3 | DIA | (0.02) | W-4 |
| 23 | A-11 | (0.2) | z38 | (0.3) | SI-4 | TPA | (0.02) | W-4 |
| 24 | A-41 | (0.25) | z34 | (0.4) | SI-5 | TMEA | (0.03) | W-1 |

TABLE 2-continued

| | | | | Silicon-Containing, Positive | | | | |
|---|---|---|---|---|---|---|---|---|
| Comparative Example | | | | | | | | |
| 4 | none | (—) | z38 | (0.4) | SI-1 | PEA | (0.02) | W-1 |
| 5 | TPSB | (0.2) | z38 | (0.3) | SI-4 | DIA | (0.02) | W-4 |
| 6 | TPSPB | (0.2) | z58 | (0.4) | SI-4 | TPA | (0.02) | W-4 |

| | Solvent | (ratio by mass) | PEB Temperature Dependency (nm/° C.) | Exposure Latitude (%) | Pattern Profile |
|---|---|---|---|---|---|
| Example | | | | | |
| 19 | A1/A3 | (80/20) | 3.7 | 18.6 | rectangular |
| 20 | A1/A3 | (60/40) | 4.3 | 21.2 | rectangular |
| 21 | A1 | (100) | 3.8 | 19.1 | rectangular |
| 22 | A1 | (100) | 4.2 | 20.9 | rectangular |
| 23 | A1/A3 | (80/20) | 4.0 | 19.9 | rectangular |
| 24 | A1/A3 | (80/20) | 4.0 | 20.2 | rectangular |
| Comparative Example | | | | | |
| 4 | A1 | (100) | 8.3 | 9.6 | tapered |
| 5 | A1/A3 | (80/20) | 6.9 | 9.2 | tapered |
| 6 | A1/A3 | (60/40) | 7.6 | 9.6 | tapered |

As apparent from the results in Table 2, the photosensitive composition of the present invention ensures excellent property in the PEB temperature dependency, exposure latitude and pattern profile also when used as a two-layer resist.

Examples 25 to 30 and Comparative Examples 7 to 9

Preparation of Resist

The components shown in Table 3 below were dissolved in a solvent, and the resulting solution was filtered through a 0.1-μm polytetrafluoroethylene filter to prepare a positive resist solution having a solid content concentration of 14 mass %.

<Evaluation of Resist>

The prepared positive resist solution was uniformly coated by a spin coater on a silicon substrate treated with hexamethyldisilazane, and dried under heating on a hot plate at 120° C. for 90 seconds to form a resist film having a thickness of 0.4 μm.

This resist film was exposed through a mask for a line-and-space pattern by using a KrF excimer laser stepper (NA=0.63) and immediately after the exposure, heated on a hot plate at 110° C. for 90 seconds. Thereafter, the resist film was developed with an aqueous 2.38 mass % tetramethylammonium hydroxide solution at 23° C. for 60 seconds, rinsed with pure water for 30 seconds and then dried to form a line pattern. The PEB temperature dependency, exposure latitude and pattern profile were evaluated in the same manner as in Example 1.

The evaluation results are shown in Table 3.

TABLE 3

| | | | | KrF, Positive | | | | | |
|---|---|---|---|---|---|---|---|---|---|
| Example | Compound (A) | (g) | Acid Generator | (g) | Resin (10 g) | Basic Compound | (g) | Surfactant (0.03 g) | |
| 25 | A-1 | (0.2) | z38 | (0.4) | R-1 | PEA | (0.04) | W-4 | |
| 26 | A-7 | (0.5) | z38 | (0.4) | R-2 | PEA/DIA | (0.01/0.02) | W-4 | |
| 27 | A-16 | (0.2) | z58 | (0.4) | R-1 | TMEA | (0.02) | W-4 | |
| 28 | A-28 | (0.3) | z59 | (0.3) | R-3 | PEA | (0.04) | W-4 | |
| 29 | A-11 | (0.2) | z38 | (0.3) | R-5 | DIA | (0.02) | W-2 | |
| 30 | A-41 | (0.35) | z34 | (0.4) | R-2 | DIA | (0.03) | W-3 | |

| Comparative Example | Comparative Compound | (g) | Acid Generator | (g) | Resin (10 g) | Basic Compound | (g) | Surfactant (0.03 g) |
|---|---|---|---|---|---|---|---|---|
| 7 | none | (—) | z38 | (0.4) | R-2 | PEA | (0.02) | W-4 |
| 8 | TPSB | (0.2) | z38 | (0.4) | R-2 | PEA | (0.02) | W-4 |
| 9 | TPSPB | (0.2) | z58 | (0.4) | R-1 | DIA | (0.02) | W-1 |

| | Solvent | (ratio by mass) | PEB Temperature Dependency (nm/° C.) | Exposure Latitude (%) | Pattern Profile |
|---|---|---|---|---|---|
| Example | | | | | |
| 25 | A1/B1 | (60/40) | 4.6 | 22.5 | rectangular |
| 26 | A1/B1 | (60/40) | 4.7 | 23.0 | rectangular |
| 27 | A1/B1 | (60/40) | 4.8 | 23.3 | rectangular |
| 28 | A1/B1 | (60/40) | 3.7 | 18.9 | rectangular |

TABLE 3-continued

| | | | KrF, Positive | | | |
|---|---|---|---|---|---|---|
| 29 | A1/A4 | (80/20) | 4.9 | 23.7 | rectangular | |
| 30 | A1/B1 | (60/40) | 4.3 | 21.2 | rectangular | |
| Comparative Example | | | | | | |
| 7 | A1/B1 | (60/40) | 7.1 | 10.3 | tapered | |
| 8 | A1/B1 | (80/20) | 8.1 | 9.9 | tapered | |
| 9 | A1/A3 | (60/40) | 7.3 | 12.1 | tapered | |

The weight average molecular weight and dispersity of each of Resins (R-1) to (R-5) used in Table 3 are shown in Table 4 below.

TABLE 4

| Resin | Weight Average Molecular Weight | Dispersity (Mw/Mn) |
|---|---|---|
| R-1 | 13000 | 1.2 |
| R-2 | 11000 | 1.7 |
| R-3 | 13000 | 1.2 |
| R-4 | 10000 | 1.8 |
| R-5 | 11000 | 1.8 |

As apparent from the results in Table 3, the photosensitive composition of the present invention ensures excellent property in the PEB temperature dependency, exposure latitude and pattern profile also as a positive resist composition for exposure with a KrF excimer laser.

Examples 31 to 36 and Comparative Examples 10 to 12

Preparation of Resist

The components shown in Table 5 below were dissolved in a solvent, and the resulting solution was filtered through a 0.1-μm polytetrafluoroethylene filter to prepare a negative resist solution having a solid content concentration of 14 mass %.

The prepared negative resist solutions were evaluated in the same manner as in Example 25. The results obtained are shown in Table 5.

TABLE 5

| | | | KrF, Negative | | | | | |
|---|---|---|---|---|---|---|---|---|
| Example | Compound (A) | (g) | Acid Generator | (g) | Resin (10 g) | Crosslinking Agent (g) | Basic Compound | (g) |
| 31 | A-1 | (0.3) | z38 | (0.4) | P-1 | CL-1(3) | PEA | (0.02) |
| 32 | A-7 | (0.5) | z38 | (0.3) | P-1 | CL-2(2) | PEA/DIA | (0.01/0.02) |
| 33 | A-16 | (0.2) | z38 | (0.3) | P-2 | CL-3(2) | DIA | (0.04) |
| 34 | A-28 | (0.5) | z14 | (0.3) | P-2 | CL-4(3) | PEA | (0.02) |
| 35 | A-11 | (0.4) | z59 | (0.3) | P-2 | CL-5(2) | DIA | (0.03) |
| 36 | A-41 | (0.35) | z61 | (0.5) | P-3 | CL-6(2) | PEA | (0.02) |

| Comparative Example | Comparative Compound | (g) | Acid Generator | (g) | Resin (10 g) | Crosslinking Agent (g) | Basic Compound | (g) |
|---|---|---|---|---|---|---|---|---|
| 10 | none | (—) | z38 | (0.4) | P-1 | CL-1(3) | HAP | (0.02) |
| 11 | TPSB | (0.2) | z38 | (0.5) | P-2 | CL-2(2) | DIA | (0.03) |
| 12 | TPSPB | (0.2) | z58 | (0.45) | P-3 | CL-3(2) | PEA | (0.02) |

| | Surfactant (0.03 g) | Solvent | (ratio by mass) | PEB Temperature Dependency (nm/° C.) | Exposure Latitude (%) | Pattern Profile |
|---|---|---|---|---|---|---|
| Example | | | | | | |
| 31 | W-4 | A1/B1 | (60/40) | 3.9 | 19.6 | rectangular |
| 32 | W-3 | A1/B1 | (60/40) | 4.1 | 20.4 | rectangular |
| 33 | W-1 | A1/A4 | (80/20) | 4.9 | 19.1 | rectangular |
| 34 | W-4 | A1/B1 | (80/20) | 4.2 | 20.6 | rectangular |
| 35 | W-4 | A1/B1 | (60/40) | 4.6 | 18.3 | rectangular |
| 36 | W-4 | A1/B1 | (60/40) | 4.1 | 20.2 | rectangular |
| Comparative Example | | | | | | |
| 10 | W-1 | A1/B1 | (60/40) | 7.2 | 10.2 | tapered |
| 11 | W-4 | A1/B1 | (70/30) | 7.9 | 9.3 | tapered |
| 12 | W-4 | A1/A3 | (60/40) | 7.8 | 8.1 | tapered |

The structure, molecular weight and molecular weight distribution of each alkali-soluble resin and the crosslinking agents in Table 5 are shown below.

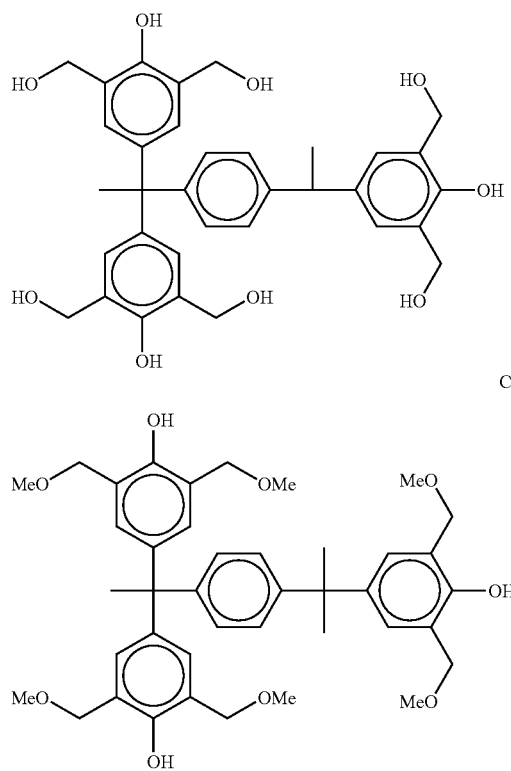

VP-5000 produced by Nippon Soda Co., Ltd.

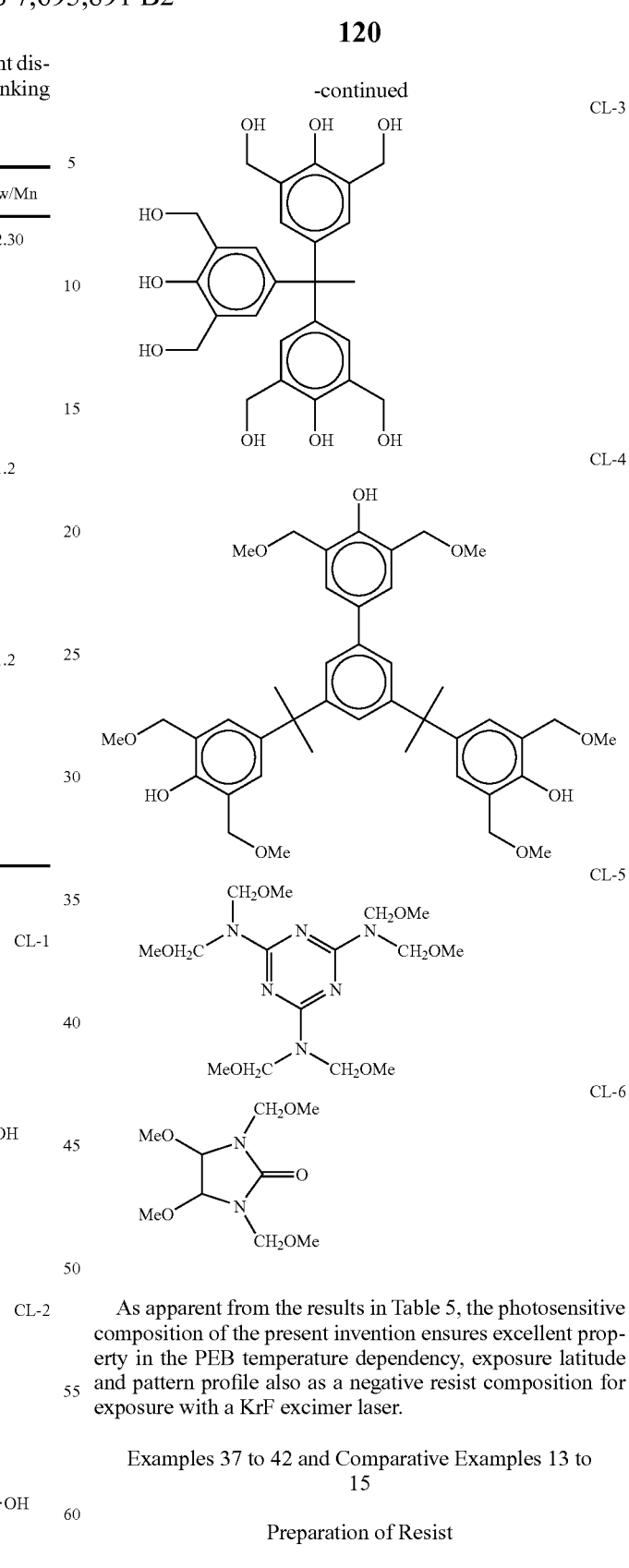

As apparent from the results in Table 5, the photosensitive composition of the present invention ensures excellent property in the PEB temperature dependency, exposure latitude and pattern profile also as a negative resist composition for exposure with a KrF excimer laser.

Examples 37 to 42 and Comparative Examples 13 to 15

Preparation of Resist

The components shown in Table 3 were dissolved in a solvent, and the resulting solution was filtered through a 0.1-μm polytetrafluoroethylene filter to prepare a positive resist solution having a solid content concentration of 12 mass %.

<Evaluation of Resist>

The prepared positive resist solution was uniformly coated by a spin coater on a silicon substrate treated with hexamethyldisilazane, and dried under heating on a hot plate at 120° C. for 60 seconds to form a resist film having a thickness of 0.3 µm.

This resist film was irradiated by an electron beam projection lithography apparatus manufactured by Nikon Corp. (accelerating voltage: 100 KeV) and immediately after the irradiation, heated on a hot plate at 110° C. for 90 seconds. Furthermore, the resist film was developed with an aqueous tetramethylammonium hydroxide solution having a concentration of 2.38 mass % at 23° C. for 60 seconds, rinsed with pure water for 30 seconds and then dried to form a line-and-space pattern. The PEB temperature dependency, exposure latitude and pattern profile were evaluated in the same manner as in Example 1.

The evaluation results are shown in Table 6.

TABLE 6

| | EB, positive | | |
|---|---|---|---|
| | PEB Temperature Dependency (nm/° C.) | Exposure Latitude (%) | Pattern Profile |
| Example | | | |
| 37 | 3.9 | 19.4 | rectangular |
| 38 | 4.1 | 15.1 | rectangular |
| 39 | 4.9 | 18.6 | rectangular |
| 40 | 4.9 | 16.8 | rectangular |
| 41 | 4.1 | 19.9 | rectangular |
| 42 | 4.4 | 16.7 | rectangular |
| Comparative Example | | | |
| 13 | 7.3 | 9.6 | tapered |
| 14 | 7.2 | 8.9 | tapered |
| 15 | 8.8 | 10.1 | tapered |

As apparent from the results in Table 6, the photosensitive composition of the present invention ensures excellent property in the PEB temperature dependency, exposure latitude and pattern profile also as a positive resist composition for electron beam irradiation.

Examples 43 to 48 and Comparative Examples 16 to 18

Preparation of Resist

The components shown in Table 5 were dissolved in a solvent, and the resulting solution was filtered through a 0.1-µm polytetrafluoroethylene filter to prepare a negative resist solution having a solid content concentration of 12 mass %.

<Evaluation of Resist>

The prepared negative resist solution was uniformly coated by a spin coater on a silicon substrate treated with hexamethyldisilazane, and dried under heating on a hot plate at 120° C. for 60 seconds to form a resist film having a thickness of 0.3 µm.

This resist film was irradiated by an electron beam projection lithography apparatus manufactured by Nikon Corp. (accelerating voltage: 100 KeV) and immediately after the irradiation, heated on a hot plate at 110° C. for 90 seconds. Furthermore, the resist film was developed with an aqueous tetramethylammonium hydroxide solution having a concentration of 2.38 mass % at 23° C. for 60 seconds, rinsed with pure water for 30 seconds and then dried to form a line-and-space pattern. The PEB temperature dependency, exposure latitude and pattern profile were evaluated in the same manner as in Example 1.

The evaluation results are shown in Table 7.

TABLE 7

| | EB, negative | | |
|---|---|---|---|
| | PEB Temperature Dependency (nm/° C.) | Exposure Latitude (%) | Pattern Profile |
| 43 | 3.7 | 18.4 | rectangular |
| 44 | 4.6 | 17.4 | rectangular |
| 45 | 4.2 | 23.0 | rectangular |
| 46 | 3.9 | 19.4 | rectangular |
| 47 | 3.9 | 21.4 | rectangular |
| 48 | 4.2 | 19.9 | rectangular |
| Comparative Example | | | |
| 16 | 8.4 | 9.6 | tapered |
| 17 | 7.9 | 9.5 | tapered |
| 18 | 8.5 | 9.1 | tapered |

As apparent from the results in Table 7, the photosensitive composition of the present invention ensures excellent property in the PEB temperature dependency, exposure latitude and pattern profile also as a negative resist composition for electron beam irradiation.

Examples 49 to 54 and Comparative Examples 19 to 21

The components shown in Table 3 were dissolved in a solvent, and the resulting solution was filtered through a 0.1-µm polytetrafluoroethylene filter to prepare a positive resist solution having a solid content concentration of 8 mass %. The evaluations were performed as follows.

<Evaluation of Resist>

The prepared positive resist solution was uniformly coated by a spin coater on a silicon substrate treated with hexamethyldisilazane, and dried under heating on a hot plate at 120° C. for 60 seconds to form a resist film having a thickness of 0.15 µm. The obtained resist film was subjected to surface exposure with EUV light (wavelength: 13 nm) while changing the exposure amount in 0.5-mJ steps in the range from 0 to 10.0 mJ and baked at 110° C. for 90 seconds. Thereafter, the dissolution rate at each exposure amount was measured by using an aqueous 2.38% tetramethylammonium hydroxide (TMAH) solution, and a sensitivity curve was obtained from the measured values. The sensitivity was defined as the exposure amount when the dissolution rate of resist was saturated on this sensitivity curve. Also, the dissolution contrast ($\gamma$ value) was calculated from the gradient in the straight line part of the sensitivity curve. As the $\gamma$ value is larger, the dissolution contrast is better.

The evaluation results are shown in Table 8 below.

TABLE 8

| | EUV | |
|---|---|---|
| | Sensitivity (mJ/cm$^2$) | $\gamma$ Value |
| Example | | |
| 49 | 2.1 | 16.2 |
| 50 | 2.2 | 16.4 |

TABLE 8-continued

| | EUV | |
|---|---|---|
| | Sensitivity (mJ/cm$^2$) | γ Value |
| 51 | 2.3 | 15.2 |
| 52 | 1.9 | 15.5 |
| 53 | 2.2 | 17.3 |
| 54 | 2 | 15.8 |
| Comparative Example | | |
| 19 | 5.1 | 7.1 |
| 20 | 5.3 | 7.6 |
| 21 | 5.2 | 6.9 |

As apparent from the results in Table 8, the resist composition of the present invention is excellent in terms of high sensitivity and high contrast in the characteristic evaluation by the irradiation of EUV light as compared with the compositions of Comparative Examples.

According to the present invention, a photosensitive composition assured of low PEB temperature dependency, large exposure latitude and good pattern profile and improved in the sensitivity and dissolution contrast at the exposure with EUV light, a pattern forming method using the photosensitive composition, and a compound for use in the photosensitive composition can be provided.

The entire disclosure of each and every foreign patent application from which the benefit of foreign priority has been claimed in the present application is incorporated herein by reference, as if fully set forth.

What is claimed is:

1. A photosensitive composition for exposure with an ArF excimer laser comprising:
   (A) a compound capable of generating a compound represented by formula (I) upon irradiation with actinic rays or radiation:

A-R—X—F     (I)

wherein X represents —CO— or —SO$_2$—;
   R represents a fluorine atom-containing divalent linking group;
   A represents an acidic group; and
   (C) a resin having a group capable of decomposing under the action of an acid to increase a solubility of resin (C) in alkali developer;
   wherein the compound (A) capable of generating a compound represented by formula (I) upon irradiation with actinic rays or radiation is a sulfonium salt compound of the compound represented by formula (I) or an iodonium salt compound of the compound represented by formula (I);
   the acidic group of A in formula (I) is —SO$_3$H, —CO$_2$H or —X—NH—X—R$_1$, wherein X represents —CO— or —SO$_2$—, and a plurality of X's may be the same or different; R$_1$ represents a monovalent organic group and the resin (C) has no aromatic group.

2. A pattern forming method comprising:
   forming a photosensitive film from a photosensitive composition according to claim 1; and
   exposing and developing the photosensitive film.

3. The photosensitive composition according to claim 1, which further comprises (B) a compound capable of generating an acid upon irradiation with actinic rays or radiation.

4. The photosensitive composition according to claim 3, wherein the compound as the component (B) is a sulfonium salt of fluoro-substituted alkanesulfonic acid, fluorine-substituted benzenesulfonic acid or fluorine-substituted imide acid.

5. The photosensitive composition according to claim 1, wherein the resin as the component (C) has a fluorine atom in a main or side chain.

6. The photosensitive composition according to claim 5, wherein the resin as the component (C) has a hexafluoroisopropanol structure.

7. The photosensitive composition according to claim 1, wherein the resin as the component (C) has at least one repeating unit selected from 2-alkyl-2-adamantyl (meth)acrylate and dialkyl(1-adamantyl)methyl (meth)acrylate.

8. The photosensitive composition according to claim 1, wherein the resin as the component (C) has a monocyclic or polycyclic alicyclic hydrocarbon structure.

9. The photosensitive composition according to claim 8, wherein the resin as the component (C) has at least one repeating unit selected from 2-alkyl-2-adamantyl (meth)acrylate and dialkyl(1-adamantyl)methyl (meth)acrylate, at least one repeating unit having a lactone structure and at least one repeating unit having a hydroxyl group.

10. The photosensitive composition according to claim 9, wherein the resin as the component (C) further has a repeating unit having a carboxyl group.

11. The photosensitive composition according to claim 1, wherein the resin as the component (C) has a silicon atom in a main or side chain.

12. The photosensitive composition according to claim 1, wherein the resin as the component (C) has a repeating unit having a lactone structure.

13. The photosensitive composition according to claim 1, which further comprises at least one of (G) a basic compound and (H) at least one of a fluorine-containing surfactant and a silicon-containing surfactant.

14. The photosensitive composition according to claim 13, wherein the basic compound (G) is a compound having a structure selected from an imidazole structure, a diazabicyclo structure, an onium hydroxide structure, an onium carboxylate structure, a trialkylamine structure, an aniline structure and a pyridine structure, an alkylamine derivative having at least one of a hydroxyl group and an ether bond or an aniline derivative having at least one of a hydroxyl group and an ether bond.

15. The photosensitive composition according to claim 1, wherein the divalent linking group represented by R in formula (I) is a fluorine atom-containing divalent linking group having a carbon number of 1 to 8.

16. The photosensitive composition according to claim 1, wherein the fluorine atom-containing divalent linking group represented by R in Formula (I) is a fluorine atom-containing alkylene group or a fluorine atom-containing phenylene group.

17. The photosensitive composition according to claim 1, wherein R$_1$ represents as alkyl group, a cycloalkyl group, an aryl group, an aralkyl group or an alkenyl group and wherein each R$_1$ group optionally has a substituent.

18. A compound represented by formula (A1) or (A2):

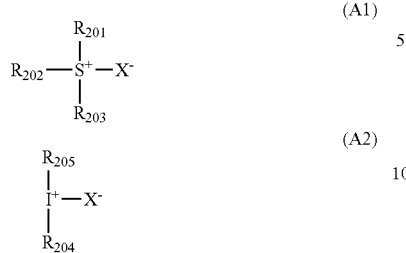

wherein $R_{201}$, $R_{202}$ and $R_{203}$ each independently represents an organic group;
$R_{204}$ and $R_{205}$ each independently represents an aryl group, an alkyl group or a cycloalkyl group; and
X represents an anion of the compound represented by formula (I)

wherein X represents —CO— or —SO$_2$—;
R represents a fluorine atom-containing divalent linking group;
A represents an acidic group;
the acidic group of A in formula (I) is —SO$_3$H, —CO$_2$H or —X—NH—X—R$_1$, wherein X represents —CO— or —SO$_2$—, and a plurality of X's may be the same or different and
R$_1$ represents a monovalent organic group.

19. The compound according to claim 18, wherein the divalent linking group represented by R in formula (I) is a fluorine atom-containing divalent linking group having a carbon number of 1 to 8.

20. The photosensitive composition according to claim 18, wherein the fluorine atom-containing divalent linking group represented by R in Formula (I) is a fluorine atom-containing alkylene group or a fluorine atom-containing phenylene group.

21. The compound according to claim 18, wherein R$_1$ represents as alkyl group, a cycloalkyl group, an aryl group, an aralkyl group or an alkenyl group and wherein each R$_1$ group optionally has a substituent.

22. A compound (A) capable of generating a compound represented by formula (I) upon irradiation with actinic rays or radiation:

wherein X represents —CO— or —SO$_2$—;
R represents a fluorine atom-containing divalent linking group;
A represents an acidic group;
wherein the compound (A) capable of generating a compound represented by formula (I) upon irradiation with actinic rays or radiation is a sulfonium salt compound of the compound represented by formula (I) or an iodonium salt compound of the compound represented by formula (I);
the acidic group of A in formula (I) is —SO$_3$H, —CO$_2$H or —X—NH—X—R$_1$, wherein X represents —CO— or —SO$_2$—, and a plurality of X's may be the same or different; and
R$_1$ represents a monovalent organic group.

23. The compound according to claim 22, wherein the divalent linking group represented by R in formula (I) is a fluorine atom-containing divalent linking group having a carbon number of 1 to 8.

24. The photosensitive composition according to claim 22, wherein the fluorine atom-containing divalent linking group represented by R in Formula (I) is a fluorine atom-containing alkylene group or a fluorine atom-containing phenylene group.

25. The compound according to claim 22, wherein R$_1$ represents as alkyl group, a cycloalkyl group, an aryl group, an aralkyl group or an alkenyl group and wherein each R$_1$ group optionally has a substituent.

26. A negative photosensitive composition comprising:
(A) a compound capable of generating a compound represented by formula (I) upon irradiation with actinic rays or radiation:

wherein X represents —CO— or —SO$_2$—;
R represents a fluorine atom-containing divalent linking group;
A represents an acidic group;
(B) a resin soluble in an alkali developer; and
(F) an acid crosslinking agent capable of crosslinking with the resin soluble in an alkali developer under an action of an acid;
wherein the compound (A) capable of generating a compound represented by formula (I) upon irradiation with actinic rays or radiation is a sulfonium salt compound of the compound represented by formula (I) or an iodonium salt compound of the compound represented by formula (I);
the acidic group of A in formula (I) is —SO$_3$H, —CO$_2$H or —X—NH—X—R$_1$, wherein X represents —CO— or —SO$_2$—, and a plurality of X's may be the same or different; and
R$_1$ represents a monovalent organic group.

27. The photosensitive composition according to claim 26, wherein the fluorine atom-containing divalent linking group represented by R in Formula (I) is a fluorine atom-containing alkylene group or a fluorine atom-containing phenylene group.

28. The negative photosensitive composition according to claim 26, wherein R$_1$ represents as alkyl group, a cycloalkyl group, an aryl group, an aralkyl group or an alkenyl group and wherein each R$_1$ group optionally has a substituent.

* * * * *